(12) United States Patent  (10) Patent No.: US 7,923,795 B2
Kobayashi et al.  (45) Date of Patent: Apr. 12, 2011

(54) ULTRASONIC TRANSDUCER DEVICE

(75) Inventors: Takashi Kobayashi, Higashimurayama (JP); Shuntaro Machida, Kokubunji (JP)

(73) Assignee: Hitachi, Ltd., Tokyo (JP)

( * ) Notice: Subject to any disclaimer, the term of this patent is extended or adjusted under 35 U.S.C. 154(b) by 369 days.

(21) Appl. No.: 12/121,736

(22) Filed: May 15, 2008

(65) Prior Publication Data

US 2008/0283945 A1  Nov. 20, 2008

(30) Foreign Application Priority Data

May 16, 2007  (JP) ................................ 2007-130980

(51) Int. Cl.
  *H01L 29/82*  (2006.01)
(52) U.S. Cl. ......... 257/416; 257/E21.532; 257/E29.324; 310/309; 310/311
(58) Field of Classification Search .................. 257/416, 257/E29.324, E21.532; 310/309, 311, 334, 310/366
  See application file for complete search history.

(56) References Cited

U.S. PATENT DOCUMENTS

| | | | | |
|---|---|---|---|---|
| 6,271,620 | B1 * | 8/2001 | Ladabaum | 310/334 |
| 6,727,170 | B2 * | 4/2004 | Takata et al. | 438/622 |
| 7,087,023 | B2 * | 8/2006 | Daft et al. | 600/459 |
| 7,342,351 | B2 * | 3/2008 | Kubo et al. | 310/344 |
| 2006/0076887 | A1 * | 4/2006 | Kang | 313/512 |
| 2007/0057603 | A1 | 3/2007 | Azuma et al. | |
| 2007/0180916 | A1 | 8/2007 | Tian et al. | |

FOREIGN PATENT DOCUMENTS

| JP | 2003-28740 A | 1/2003 |
|---|---|---|
| JP | 2004-361115 A | 12/2004 |

OTHER PUBLICATIONS

Caronti et al., "Capacitive Micromachined Ultrasonic Transducer (CMUT) Arrays for Medical Imaging," Microelectronics Journal, vol. 37, 2006, pp. 770-773.
Ergun et al., "Capacitive Micromachined Ultrasonic Transducers: Fabrication Technology," IEEE Transactions on Ultrasonics, Ferroelectronics and Frequency Control, vol. 52, No. 12, Dec. 2005, pp. 2242-2258.
Jin et al., "The Microfabrication of Capacitive Ultrasonic Ttransducers," IEEE International Conference on Solid-State Sensors and Actuators, Jun. 1997, pp. 437-438.
Knight et al., "Fabrication and Characterization of CMUTs for Forward Looking Intravascular Ultrasound Imaging," IEEE Ultrasonic Symposium, 2003, pp. 1175-1178.

* cited by examiner

*Primary Examiner* — Phuc T Dang
(74) *Attorney, Agent, or Firm* — Miles & Stockbridge P.C.

(57) ABSTRACT

A lower electrode is formed over a semiconductor substrate via an insulator film, first and second insulator films are formed to cover the lower electrode, an upper electrode is formed over the second insulator film, third to fifth insulator films are formed to cover the upper electrode and a void is formed between the first and second insulator films between the lower and upper electrodes. An ultrasonic transducer comprises the lower electrode, the first insulator film, the void, the second insulator film and the upper electrode. A portion of the first insulator film contacting with the lower electrode is made of silicon oxide, a portion of the second insulator film contacting with the upper electrode is made of silicon oxide and the first or second insulator film includes a silicon nitride film positioned between the upper and lower electrodes and not in contact with the upper and lower electrodes.

30 Claims, 30 Drawing Sheets

ULTRASONIC TRANSDUCER DEVICE

CROSS-REFERENCE TO RELATED APPLICATION

The present application claims priority from Japanese Patent Application No. JP 2007-130980 filed on May 16, 2007, the content of which is hereby incorporated by reference into this application.

TECHNICAL FIELD OF THE INVENTION

The present invention relates to a semiconductor device, in particular, to a technique effectively applied to an ultrasonic transducer.

BACKGROUND OF THE INVENTION

An ultrasonic transducer transmits and receives an ultrasonic wave and is used in a diagnosis device for a tumor in a human body, for example.

Conventionally, an ultrasonic transducer using vibration of a piezoelectric body is used. Because of advance of a MEMS technique in recent years, a capacitive micromachined ultrasonic transducer (CMUT) in which a vibrating part having a configuration interposing a void between two layer electrodes in upper and lower portions is fabricated over a silicon substrate is actively developed toward practical use.

In comparison with a conventional transducer using a piezoelectric body, the CMUT has advantages such as a wide usable ultrasonic frequency band and a high resolution. And, since the CMUT is fabricated using an LSI process technique, microfabrication is possible. In particular, in a case where ultrasonic elements are arranged in an array and each element is controlled independently, the CMUT is considered to be indispensable. This is because although wirings for respective elements are required and the number of the wirings in the array becomes huge, wirings and even a processing circuit for a signal from an ultrasonic transmission-reception unit can be embedded in one chip in the CMUT.

A technique related to such an ultrasonic transducer is disclosed, for example, in a specification of U.S. Pat. No. 6,271,620B1 (Patent Document 1).

And, a sensor in which an insulator film and the void are interposed between upper and lower electrodes is disclosed in Japanese Patent Application Laid-Open Publication No. 2003-28740 (Patent Document 2) and Japanese Patent Application Laid-Open Publication No. 2004-361115 (Patent Document 3).

SUMMARY OF THE INVENTION

According to an examination by the inventors of the present invention, the following matters are found.

A basic configuration and operation of the CMUT examined by the inventors are explained using FIG. 19. FIG. 19 is a cross-sectional view of main portions of a CMUT cell examined by the inventors. In FIG. 19, M0E denotes a lower electrode, 105a denotes a silicon oxide film, VR denotes a void, 107a denotes a silicon oxide film, M1E denotes an upper electrode, and 9, 11, and 13 denote insulator films. A configuration in which the void VR is interposed between the upper and lower electrodes (the upper electrode M1E and the lower electrode M0E) is employed. The silicon oxide film 105a, the upper electrode M1E and insulator films 9, 11, and 13 located thereabove form a membrane and the membrane vibrates.

Operation of transmitting (sending) an ultrasonic wave is described. If a DC (direct-current) voltage and an AC (alternating-current) voltage are superposed onto the upper electrode M1E and the lower electrode M0E, an electrostatic force works between the upper electrode M1E and the lower electrode M0E, (a stacked film of) the silicon oxide film 105a, the upper electrode M1E and the insulator films 9, 11, and 13 forming the membrane over the void VR vibrate at a frequency of the applied AC voltage and the ultrasonic wave is transmitted.

Conversely, when the ultrasonic wave is to be received, a pressure of the ultrasonic wave having reached a surface of a device causes vibration of the membrane over the void. Because of this vibration, a distance between the upper electrode M1E and the lower electrode M0E changes, and therefore, the ultrasonic wave can be detected as change of electric capacity between the upper electrode M1E and the lower electrode M0E. That is, because of change of the distance between the upper and lower electrodes, the electric capacity between the upper and lower electrodes changes and a current flows. By detecting this current, the ultrasonic wave can be detected.

As evident from an above-mentioned operation principle, in the CMUT, transmission and reception of the ultrasonic wave are performed using the vibration of the membrane by the electrostatic force caused by voltage application between the upper and lower electrodes and change of the electric capacity between the upper and lower electrode due to the vibration. In general, a total of DC and AC voltages applied between the upper and lower electrodes is as high as 100V or more, and therefore, improvement of a breakdown voltage between the upper and lower electrodes is an important problem.

In particular, in the lower electrode M0E, an electric field tends to be enhanced at an edge of upper surface 121 thereof. In the edge of upper surface 121 of the lower electrode M0E, an insulator film electric field increases in comparison with an upper surface and a leakage current increases in a route 122 indicated by an arrow in FIG. 19. And, in the upper electrode M1E, the electric field tends to be enhanced at a step 123 of a lower surface generated by the void VR, the insulator film electric field increases and the leakage current increases in a route 124 indicated by an arrow in FIG. 19. This tendency is particularly significant in a case where silicon oxide films 105a and 107a are used as an insulator film between the upper and lower electrodes and the breakdown voltage is decreased. This is considered to be caused by Fowler-Nordheim tunneling conduction in which a conduction mechanism of a silicon oxide film strongly depends on an electric field.

Therefore, it is desired to improve the breakdown voltage between the upper and lower electrodes and improve performance of the semiconductor device.

With respect to these matters, it can be considered that silicon nitride films may be used as the insulator film between the upper and lower electrodes in place of the silicon oxide films 105a and 107a. Since a silicon nitride film has a dielectric constant larger than that of the silicon oxide film, a physical film thickness can be increased for the same insulator film capacity and decrease of the breakdown voltage can be suppressed.

However, as a result of the examination by the present inventors, it is found that, if single-layer silicon nitride films are used in place of the silicon oxide film 105a and the silicon oxide film 107a respectively and a cell structure in which the upper and lower electrodes (the upper electrode M1E and the lower electrode M0E) and the silicon nitride films directly contact with each other is employed, a charge is trapped in the silicon nitride films because of the leakage current between the upper and lower electrodes, a capacitance-voltage characteristic is changed with increase of a operation time, and as a result, transmitting/receiving gain fluctuates.

Therefore, it is desired to suppress fluctuation of the transmitting/receiving gain caused by charge trapping of the insulator film and improve the performance of the semiconductor device.

And, Patent Document 2 and Patent Document 3 disclose a sensor using a MEMS technique, interposing the void by the upper and lower electrodes via the insulator film and detecting a pressure and acceleration from change of the capacitance between electrodes. However, objects of both of documents are detection of physical quantity such as a pressure and acceleration only, and an active function such as application of a high voltage to transmit an ultrasonic wave is not included. Therefore, charge trapping to an intermetal insulating film by the leak current between the upper and lower electrodes caused by application of a high voltage and a problem of fluctuation of detection performance caused by the charge trapping do not occur. Therefore, in Patent Document 2 and Patent Document 3, no description about a device structure for suppressing the charge trapping to the intermetal insulating film and a manufacturing method thereof is found.

An object of the present invention is to provide a technique capable of improving the performance of the semiconductor device.

And, another object of the present invention is to provide a technique capable of achieving both of improvement of the breakdown voltage of the intermetal insulating film and suppression of the charge trapping of the intermetal insulating film.

The above and other objects and novel characteristics of the present invention will be apparent from the description of this specification and the accompanying drawings.

The typical ones of the inventions disclosed in this application will be briefly described as follows.

The present invention is a semiconductor device comprising a first electrode and a second electrode arranged so as to face each other via a first insulator film and a second insulator film stacked so as to have a void therebetween, wherein at least a portion of the first insulator film on a first electrode side contacting with the first electrode is made of silicon oxide, wherein at least a portion of the second insulator film on a second electrode side contacting with the second electrode is made of silicon oxide, and wherein at least one of the first insulator film and the second insulator film comprises a silicon nitride layer portion positioned between the first electrode and the second electrode and in contact with neither the first electrode nor the second electrode.

The effects obtained by typical aspects of the present invention will be briefly described below.

The performance of the semiconductor device can be improved.

And, both of the increase of the breakdown voltage of the intermetal insulating film and the suppression of the charge trapping of the intermetal insulating films can be achieved.

BRIEF DESCRIPTIONS OF THE DRAWINGS

DESCRIPTIONS OF THE PREFERRED EMBODIMENTS

Figure 1:
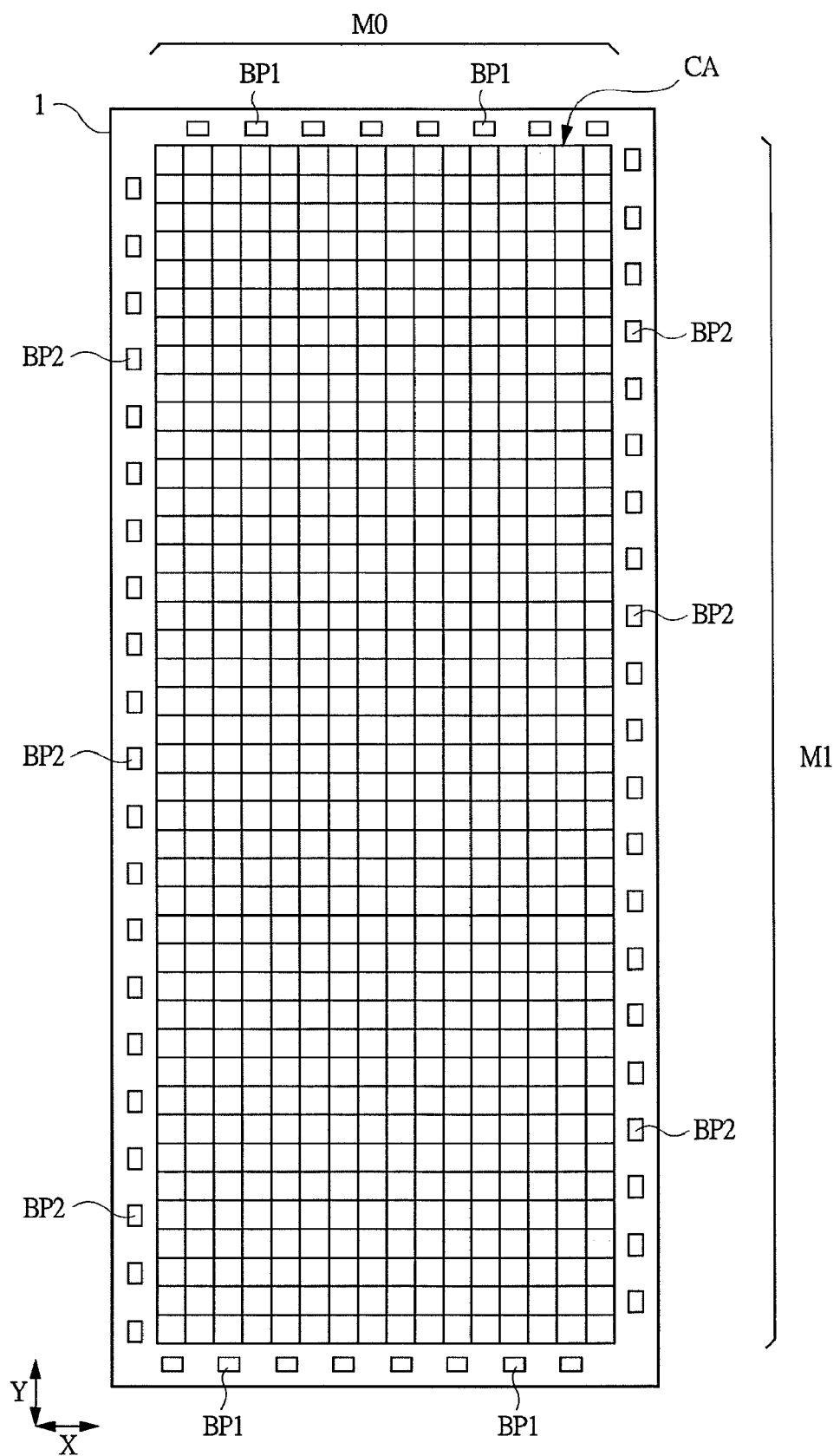
FIG. 1 is a total plan diagram of a semiconductor chip configuring a semiconductor device according to an embodiment of the present invention.

In advance of detailed description of the present invention, meanings of terms in the present application are described as follows.

1. A semiconductor substrate refers to any of a semiconductor single crystal substrate made of silicon and the like, a quartz substrate, a sapphire substrate, a glass substrate, other insulating, anti-insulating or semiconductor substrate and a combined substrate thereof and is used for manufacturing a semiconductor integrated circuit.

In the following embodiments, a description will be given by dividing into a plurality of sections or embodiments as occasion demands as a matter of convenience. However, the elements are not nothing to each other except a particularly clear description, but one is a modified example, details, a supplementary explanation or the like of a part or a whole of the other. Further, in the following embodiments, in the case of referring to a number of elements (including a number, a numerical value, an amount, a range and the like), the present invention is not limited to the defined number except the case of the particular definition and the case of apparently limited to the specific number in principle, but may be equal to or more than the defined number or equal to or less than the defined number. And, in the following embodiments, components (including elemental steps and the like) thereof are not necessarily indispensable except the case of the particular definition and the case of apparent in principle. In the same manner, in the case of referring to a shape, a positional relation and the like, ones substantially the same or similar thereto are included except the case of the particular definition and the case of not included apparently in principle. This is true for the above-mentioned number and range.

Hereinafter, embodiments of the present invention will be described in detail with reference to the accompanying drawings. Note that components having the same function are denoted by the same reference symbols throughout the drawings for describing the embodiment, and the repetitive description thereof will be omitted. And, in the embodiments, explanations of the same or similar portions are not repeated in principle except the case of necessity.

In the drawings used in the embodiments, hatching may be omitted even in a cross-sectional view for ease of understanding. And, hatching may be made even in a plane diagram for ease of understanding.

First Embodiment

A semiconductor device according to a present embodiment is an ultrasonic transducer (ultrasonic transmitting/receiving sensor) manufactured using, for example, a MEMS (Micro Electro Mechanical System) technique.

FIG. 1 is a total plan diagram of a semiconductor chip 1 configuring the semiconductor device according to the present embodiment.

The semiconductor chip 1 comprises a first main surface (upper surface, front surface) and a second main surface (lower surface, rear surface) positioned so as to be opposite to each other along a thickness direction. FIG. 1 shows a plan diagram on a first main surface side (that is, an upper surface diagram) of the semiconductor chip 1.

As shown in FIG. 1, a plane shape of the semiconductor chip 1 is formed in a rectangular shape, for example. A length of the semiconductor chip 1 in a longitudinal direction (second direction Y) is approximately 4 cm, for example, and a length of the semiconductor chip 1 in a short-side direction (first direction X) is approximately 1 cm, for example. Note that, a flat dimension of the semiconductor chip 1 is not restricted to this, but can be variously modified. There are sensors of various dimensions, for example, having a length in the longitudinal direction (the second direction Y) of approximately 8 cm and the length in the short-side direction (the first direction X) of approximately 1.5 cm.

Over the first main surface of the semiconductor chip 1, a CMUT region (CMUT cell region, sensor region, sensor cell array, transducer array) CA and a plurality of bonding pads (hereinafter referred to as pads) BP1, BP2 are arranged.

In the CMUT (Capacitive Micromachined Ultrasonic Transducer) region CA, a plurality of lower electrode wirings (lower electrodes, first electrodes) M0, a plurality of upper electrode wirings (upper electrodes, second electrodes) M1 orthogonal thereto and a plurality of transducers (CMUT cells, sensor cells, corresponding to transducers 20 described later).

The plurality of lower electrode wirings M0 are formed so as to extend along the longitudinal direction (second direction Y) of the semiconductor chip 1 respectively, and are arranged so as to be aligned in the short-side direction (first direction X) of the semiconductor chip 1, in sixteen channels (hereinafter also represented as ch), for example.

The lower electrode wirings M0 are electrically connected to the pads BP1 respectively. The pads BP1 are in periphery of the CMUT region CA and are arranged near both ends in the longitudinal direction (second direction Y) of the semiconductor chip 1 along short sides of the semiconductor chip 1 so as to correspond to the lower electrode wirings M0.

The plurality of upper electrode wirings M1 are formed so as to extend along the short-side direction (first direction X) of the semiconductor chip 1 respectively and are arranged in the longitudinal direction (second direction X) of the semiconductor chip 1, in 192 channels, for example.

The upper electrode wirings M1 are electrically connected to the pads BP2 respectively. The pads BP2 are in periphery of the CMUT region CA and are arranged near both ends in the short-side direction (first direction X) of the semiconductor chip 1 along long sides of the semiconductor chip 1 so as to correspond to the upper electrode wirings M1.

The transducers (corresponding to the transducers 20 described later) are, for example, capacitance-type transducers and are arranged at intersection points of the lower electrode wirings M0 and the upper electrode wirings M1. That is, a plurality of transducers (corresponding to the transducers 20 described later) is arranged regularly in a matrix (array) manner in the CMUT region CA. In the CMUT region CA, at intersection points of the lower electrode wirings M0 and the upper electrode wirings M1, transducers of approximately fifty pieces are arranged in parallel, for example.

Therefore, the CMUT region CA is a region in which a plurality of sensor cells or CMUT cells (corresponding to the transducers 20 described later) are formed, and the semiconductor chip 1 is a semiconductor device having the CMUT region CA over the main surface (first main surface), and the CMUT region CA has the plurality of CMUT cells formed.

Figure 2:
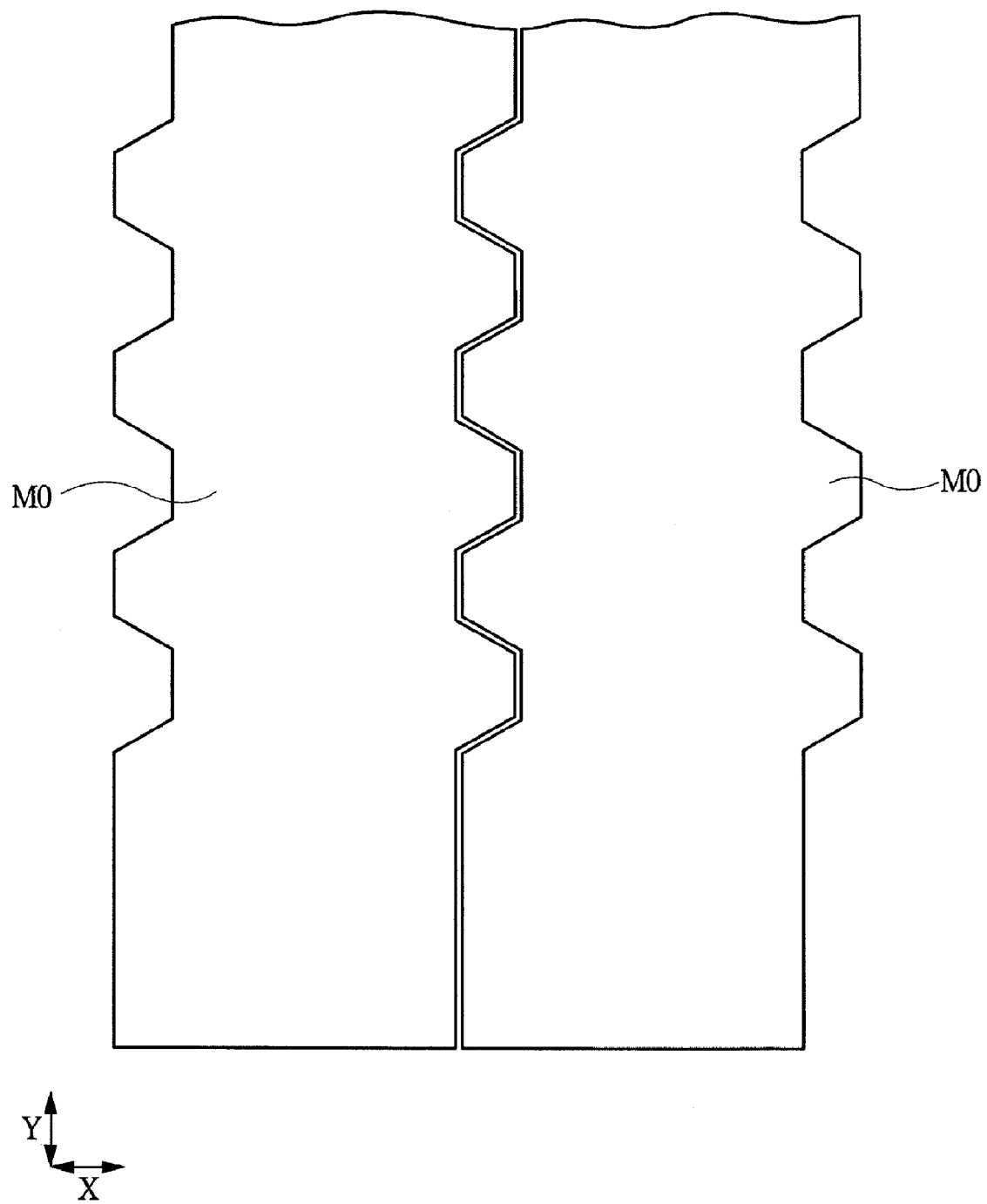
FIG. 2 is an enlarged plan diagram of a main portion of the semiconductor chip of FIG. 1.
Figure 3:
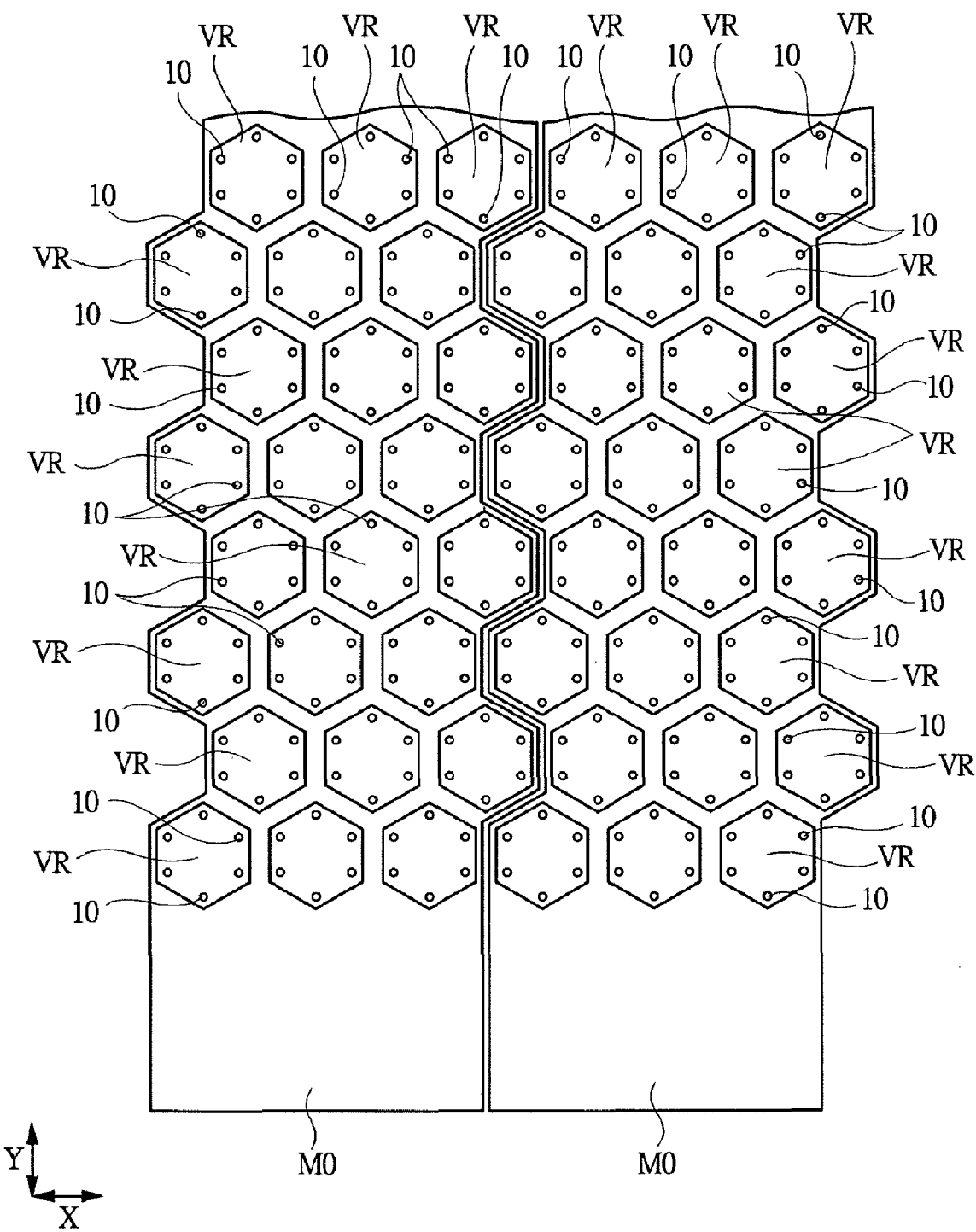
FIG. 3 is an enlarged plan diagram of the main portion of the semiconductor chip of FIG. 1.
Figure 4:
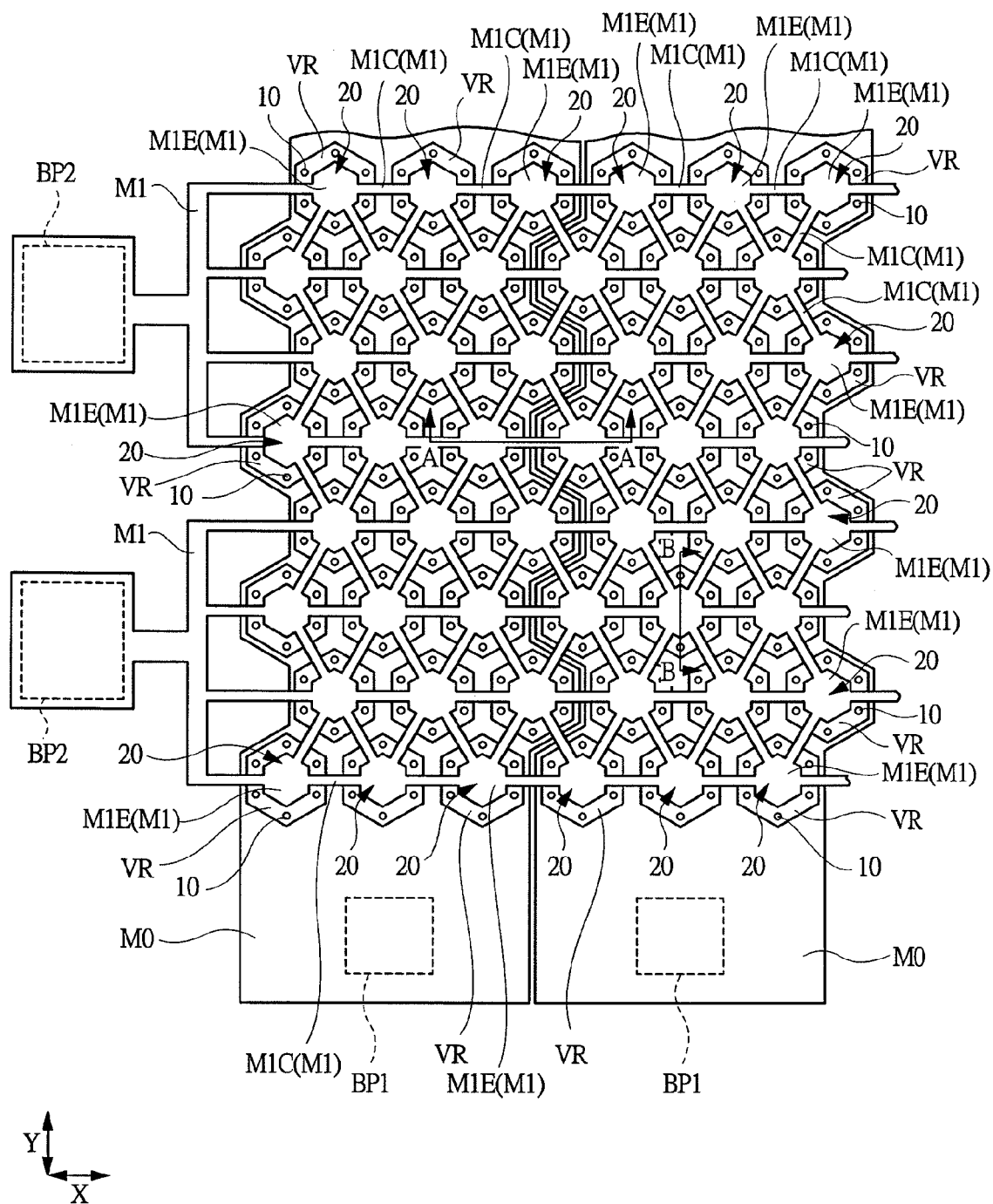
FIG. 4 is an enlarged plan diagram of the main portion of the semiconductor chip of FIG. 1.
Figure 5:
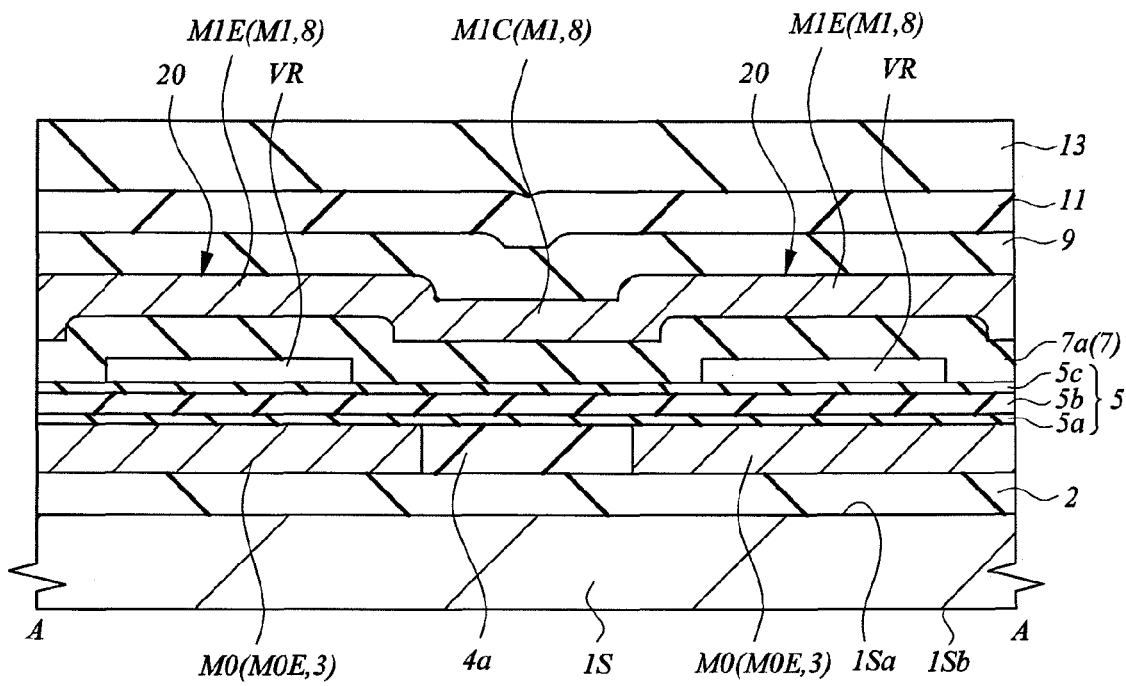
FIG. 5 is a cross-sectional view of the main portion of the semiconductor chip of FIG. 1.
Figure 6:
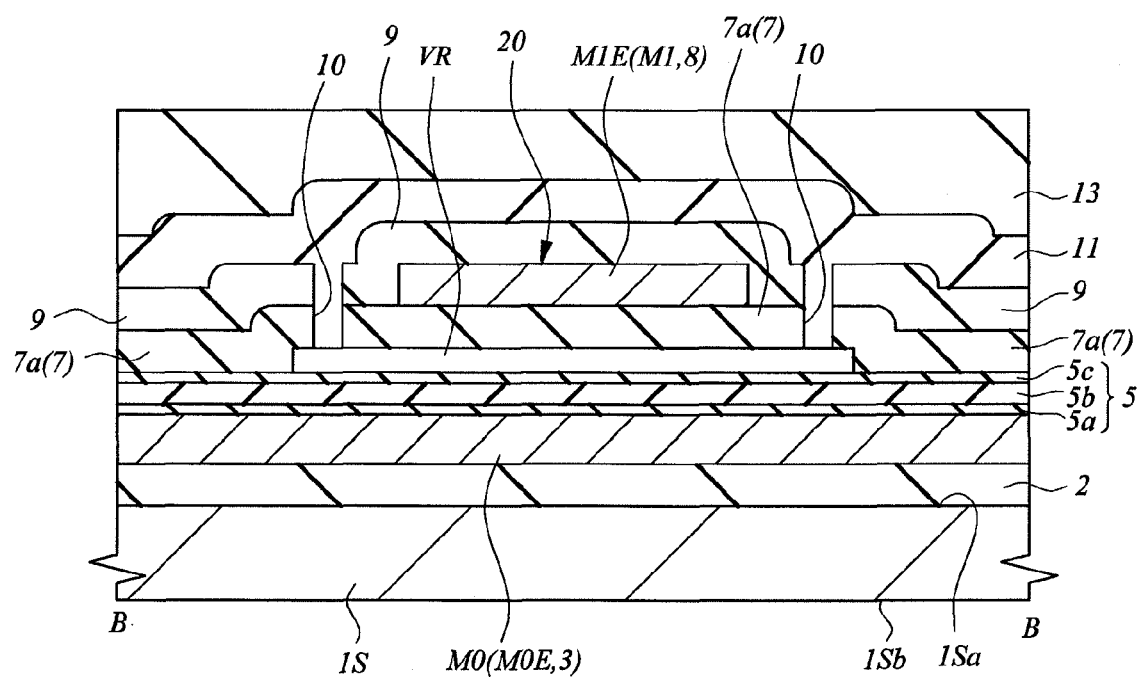
FIG. 6 is a cross-sectional view of the main portion of the semiconductor chip of FIG. 1.

Next, FIGS. 2 to 4 are main portion plan diagrams (enlarged main portion plan diagrams) of the semiconductor chip 1, and FIGS. 5 and 6 are main portion cross-sectional views of the semiconductor chip 1. FIG. 2 shows a plane layout of the lower electrode wirings M0 and other components are omitted therefrom. FIG. 3 is a diagram obtained by further adding (superposing) a plane layout of the voids VR and holes 10 to FIG. 2 and components other than the lower electrode wirings M0, the voids VR and the holes 10 are omitted therefrom. FIG. 4 is a diagram obtained by further adding (superposing) a plane layout of the upper electrode wirings M1 and the pads BP1, BP2 to FIG. 3 and components other than the lower electrode wirings M0, the voids VR, the holes 10, the upper electrode wirings M1, and the pads BP1, BP2 are omitted therefrom. And, FIG. 5 substantially corresponds to a cross-sectional view along an A-A line of FIG. 4, and FIG. 6 substantially corresponds to a cross-sectional view along a B-B line of FIG. 4. Note that, in FIGS. 2 to 4, as an example of the CMUT region CA, a plane diagram in which the lower electrode wirings M0 are 2ch, the upper electrode wirings M1 are 2ch and 12 pieces of the transducers 20 are arranged at respective intersection points of the lower electrode wiring M0 and the upper electrode wiring M1 is shown. However, the number of the transducers 20 arranged at respective intersection points is not restricted to the above.

A semiconductor substrate is configuring the semiconductor chip 1 is made of, for example, silicon (S1) single crystal, and comprises a first main surface (upper surface, front surface) 1Sa and a second main surface (lower surface, rear surface) 1Sb positioned so as to be opposite to each other along a thickness direction. As shown in FIGS. 2 to 6, the plurality of transducers (capacitive elements, CMUT cells, ultrasonic transducer cells) 20 is arranged (formed) over the first main surface 1Sa of the semiconductor substrate 1S via an insulator film (third insulator film) 2 made of, for example, silicon oxide.

As shown in FIG. 4, the plurality of transducers 20 is formed in a plane hexagonal shape respectively for example, and are arranged in a honeycomb manner for example. Thereby, the plurality of transducers 20 can be arranged with high density and sensor performance can be improved.

And, each of the transducers 20 comprises a lower electrode (lower electrode portion, first electrode) M0E, an upper electrode (upper electrode portion, second electrode) M1E provided so as to be opposite to the lower electrode M0E, and the voids VR interposed between these electrodes.

The lower electrode M0E is formed at a part of the lower electrode wirings M0 where the upper electrode wirings M1 are superposed in a plane manner. That is, the lower electrode M0E of each of the transducers 20 is composed of a part of the lower electrode wirings M0 and, and a part of the lower electrode wirings M0 superposed on the void VR in a plane manner (that is, a part under the void VR) becomes the lower electrode M0E. And, the lower electrode wirings M0 are conductor patterns for the lower electrodes of the transducers 20, and the entire lower electrode wirings M0 (patterns themselves of the lower electrode wirings M0) can be considered as an electrode (lower electrode, first electrode).

The electrode wirings M0 (lower electrodes M0E) are composed of a patterned conductive film 3 and composed of a stacked film of a titanium nitride (TiN) film, an aluminum (Al) film and a titanium nitride film sequentially stacked from below. In place of the titanium nitride film, a tungsten (W) film may be used.

Between adjacent lower electrode wirings M0 (lower electrodes M0E), an insulator film (buried insulating film) 4a is buried. That is, the insulator film 4a is formed so as to fill a gap between adjacent lower electrode wirings M0 (lower electrodes M0E) and a substantially flat surface is formed from the upper surface of the insulator film 4a and the upper surfaces between the lower electrode wirings M0 (between lower electrodes M0E). The insulator film 4a is made of silicon oxide, for example.

The lower electrode wirings M0 (lower electrodes M0E) are formed over the first main surface 1Sa of the semiconductor substrate 1 via the insulator film 2, and an insulator film (first insulator film) 5 is formed (deposited) over the insulator film 2 (the first main surface 1Sa of the semiconductor substrate 1) so as to cover the lower electrode wirings M0 (lower electrodes M0E). As described above, since the insulator film 4a is buried between the lower electrode wirings M0 (between lower electrodes M0E), the insulator film 5 is deposited (formed) over the lower electrode wirings M0 (lower electrodes M0E) and the insulator film 4a. In the present embodiment, the insulator film 5 is composed of a stacked film of a silicon oxide film 5a, a silicon nitride film 5b and a silicon oxide film 5c sequentially stacked from below (a side of the lower electrode wirings M0).

An insulator film (second insulator film) 7 formed (deposited) over the insulator film 5. In the present embodiment, the insulator film 7 is composed of a single layer film (single film or single layer) of a silicon oxide film 7a. Over the insulator film 7, the upper electrodes M1E are provided so as to face the lower electrodes M0E.

The upper electrodes M1E are formed at a part of the upper electrode wirings M1 where the lower electrode wirings M0 are superposed in a plane manner. That is, the upper electrodes M1E of respective transducers 20 are composed of a part of the upper electrode wirings M1 and, parts of the upper electrode wirings M1 superposed on the lower electrode wirings M0 in a plane manner (that is, a part positioned above the lower electrode wirings M0) become the upper electrodes M1E. A plane shape of the upper electrodes M1E are formed in a substantially hexagonal shape and is formed in a pattern wider than a connecting portion M1C connecting between the upper electrodes M1E in the upper electrode wirings M1. In this manner, the upper electrode wirings M1 comprise the plurality of upper electrodes M1E and the connecting portion M1C connecting between adjacent upper electrodes M1E in the first direction X. And, the upper electrode wirings M1 are conductor patterns for upper electrodes of the transducers 20, and the entire upper electrode wirings M1 (a combination of the upper electrodes M1E and the connecting portion M1C or the pattern itself of the upper electrode wirings M1) can be considered as electrodes (upper electrodes, second electrodes).

The upper electrode wirings M1 comprising the upper electrodes M1E and the connecting portion M1C are composed of a patterned conductive film 8 and are composed of a stacked film of, for example, a titanium nitride (TiN) film, an aluminum (Al) film and a titanium nitride film (TiN) sequentially stacked from below. In place of the titanium nitride film, a tungsten film may be used.

Between these lower electrodes M0E (lower electrode wirings M0) and upper electrodes M1E (upper electrode wirings M1) (between facing surfaces), the voids VR are formed. The void VR are formed between the insulator film 5 and the insulator film 7 to be surrounded by an upper surface of the insulator film 5 and a lower surface of the insulator film 7. A plane shape of the void VR is formed in a hexagonal shape, for example. Also a plane shape of the upper electrodes M1E is formed in a hexagonal shape, for example. And, a plane pattern of the upper electrode M1E can be formed so as to be included in the plane pattern of the void VR in a plane manner.

The insulator film 5 composed of a stacked film of the silicon oxide film 5a, the silicon nitride film 5b and the silicon oxide film 5a is arranged between the lower electrodes M0E and the voids VR and has a function of ensuring a breakdown voltage between the upper and lower electrodes (between the upper electrodes M1E and the lower electrodes M0E). And, the insulator film 7 is arranged between the voids VR and the upper electrode wirings M1 (upper electrodes M1E) and has a function of ensuring a breakdown voltage between the upper and lower electrodes together with the insulator film 5.

Over the insulator film 7, an insulator film 9 composed of a silicon nitride film, for example, is deposited (formed) so as to cover the upper electrode wirings M1 including the upper electrodes M1E and the connecting portion M1C. In insulator films 7 and 9, a hole (opening, via hole, through hole) 10 reaching the voids VR is formed near a hexagonal portion of the void VR. As described later, the hole 10 is a hole for forming the void VR by etching a sacrificial film pattern (sacrificial film pattern 6 described later) between the insulator film 5 and the insulator film 7 via the hole 10.

Over the insulator film 9, an insulator film 11 composed of, for example, a silicon nitride film, is formed (deposited). A part of this insulator film 11 penetrates into the hole 10, and thereby the hole 10 is blocked.

Over the insulator film 11, an insulator film 13 composed of a photosensitive polyimide film or the like is formed (deposited) as a protection film.

In insulator films 5, 7, 9, 11 and 13, an opening (not shown) reaching a part of the lower electrode wirings M0 is formed, and the part of the lower electrode wirings M0 exposed from this opening serves as the pad BP1. And, in insulator films 9, 11 and 13, an opening (not shown) reaching a part of the upper electrode wirings M1 is formed, and the part of the upper electrode wirings M1 exposed from this opening serves as the pad BP2. Note that, these pads BP1 and BP2 are input/output terminals of the semiconductor chip 1, and bonding wires are electrically connected to the pads BP1, BP2.

As described above, the insulator film 5 and the insulator film 7 are interposed between the lower electrode wirings M0 (lower electrodes M0E) and the upper electrode wirings M1 (upper electrodes M1E). In regions interposed between the lower electrodes M0E and the upper electrodes M1E, the voids VR are provided between the insulator film 5 and the insulator film 7. The insulator film 5 is interposed between the lower electrodes M0E and the voids VR, and the insulator film 7 is interposed between the voids VR and the upper electrodes M1E.

Each of the plurality of the CMUT cells (transducers 20) of the semiconductor chip 1 is the ultrasonic transducer (variable capacity sensor) composed of the lower electrode M0E (lower electrode wiring M0), the upper electrode M1E (upper electrode wiring M1), the insulator film 5 between the lower electrode M0E (lower electrode wiring M0) and the upper electrode M1E (upper electrode wiring M1), the void VR and the insulator film 7. That is, a capacitive element is formed from (configured of) the lower electrode M0E (lower electrode wiring M0), the upper electrode M1E (upper electrode wiring M1), the insulator film 5 between the lower electrode M0E (lower electrode wiring M0) and the upper electrode M1E (upper electrode wiring M1), the void VR and the insulator film 7, and more specifically, the ultrasonic transducer is formed (configured).

Next, a method of manufacturing the semiconductor device according to the present embodiment is described with reference to FIGS. 7 to 18. Note that, FIGS. 7 to 18 are main portion cross-sectional views of the semiconductor device during a manufacturing processing according to the present embodiment. Among FIGS. 7 to 18, FIGS. 7 to 13 are cross-sectional views of a region corresponding to FIG. 5 (cross-sectional views of a position corresponding to the A-A line in FIG. 4), and FIGS. 14 to 18 are cross-sectional views of a region corresponding to FIG. 6 (cross-sectional views of a portion corresponding to the B-B line in FIG. 4).

Figure 7:
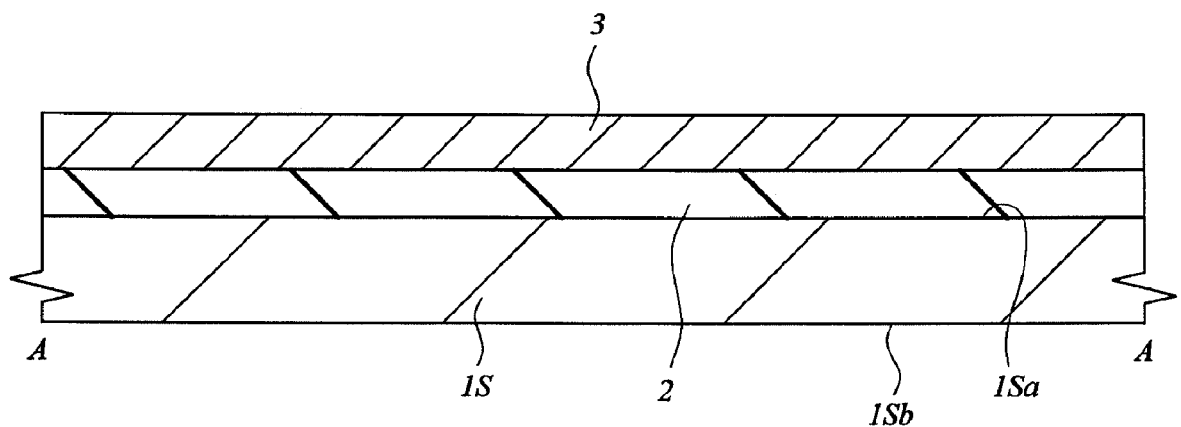
FIG. 7 is a cross-sectional view of a main portion of a semiconductor device during a manufacturing processing according to a first embodiment of the present invention.

To manufacture the semiconductor chip 1, as shown in FIG. 7, the semiconductor substrate (at this stage, a semiconductor thin plate of a plane and substantially circular shape called a semiconductor wafer) 1S is first prepared. The semiconductor substrate 1S is formed of, for example, silicon single crystal, and has the first main surface (upper surface, front surface) 1Sa and the second main surface (lower surface, rear surface) 1Sb positioned so as to be opposite to each other along the thickness direction.

Next, over the entire surface of the first main surface 1Sa of the semiconductor substrate 1S, an insulator film 2 formed of, for example, a silicon oxide film, is formed (deposited). A film thickness of the insulator film 2 can be set to approximately 800 nm, for example.

Next, over the insulator film 2, a conductive film (conductive layer) 3 for formation of a lower electrode wiring is formed (deposited). The conductive film 3 is formed over the entire surface of the first main surface 1Sa of the semiconductor substrate 1S. The conductive film 3 is composed of a metal film or a film having metallic conduction and composed of a stacked film of a titanium nitride (TiN) film, an aluminum (Al) film and a titanium nitride (TiN) film sequentially formed from below, for example. This aluminum film is composed of a conductive film containing aluminum as a main ingredient, such as an aluminum single film or an aluminum alloy film. The conductive film 3 can be formed using a sputtering method, for example. And, when the conductive film 3 is a stacked film of a titanium nitride film, an aluminum film and a titanium nitride film, the aluminum film becomes a main conductive film of the lower electrode wiring M0. Therefore, a film thickness of the aluminum film can be larger than a film thickness of the titanium nitride film. For example, the film thickness of the aluminum film can be approximately 600 nm, and the film thickness of each titanium nitride film above and below the aluminum film can be approximately 50 nm. And, in place of the titanium nitride film, a stacked film of a titanium (Ti) film and a titanium nitride film or a tungsten (W) film can be used.

Figure 8:
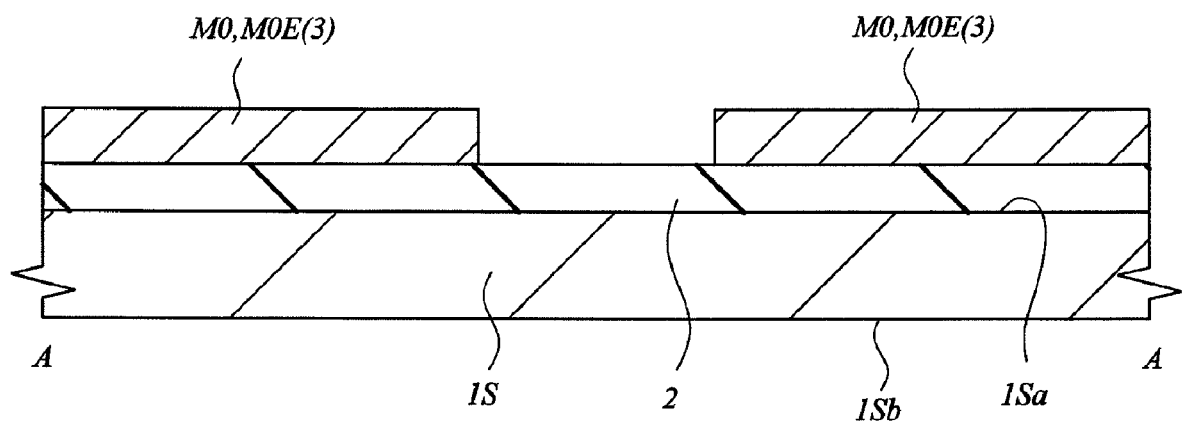
FIG. 8 is a cross-sectional view of the main portion the semiconductor device during the manufacturing processing continued from FIG. 7.

Next, as shown in FIG. 8, the conductive film 3 is patterned (processed) using a lithography method, a dry etching method or the like. By the patterned conductive film (conductive layer) 3, the lower electrode wiring M0 (lower electrode M0E) is formed.

In this manner, the lower electrode wiring M0 is formed over (the insulator film 2 over) the semiconductor substrate 1S. Note that, the lithography method is a method of patterning a resist film into a desired pattern through a series of processings of coating of the resist film (photoresist film), exposure and development.

Figure 9:
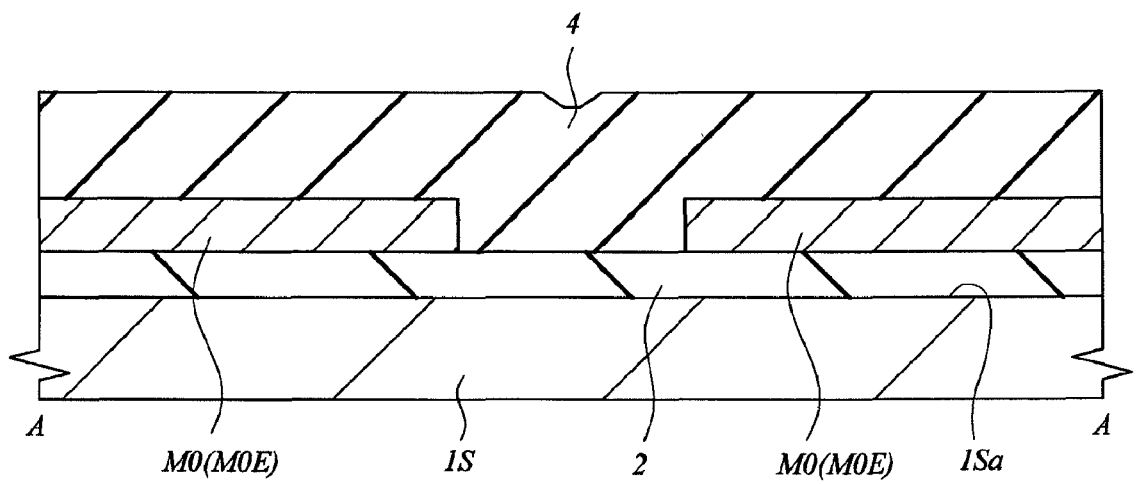
FIG. 9 is a cross-sectional view of the main portion of the semiconductor device during the manufacturing processing continued from FIG. 8.

Next, as shown in FIG. 9, over (the insulator film 2 over) the semiconductor substrate 1S, an insulator film 4, such as a silicon oxide film, is formed (deposited) using a plasma-enhanced CVD (Chemical Vapor Deposition) method so as to cover the lower electrode wirings M0. At this time, the insulator film 4 is deposited so as to have a thickness capable of sufficiently filling a space between adjacent lower electrode wirings M0.

Figure 10:
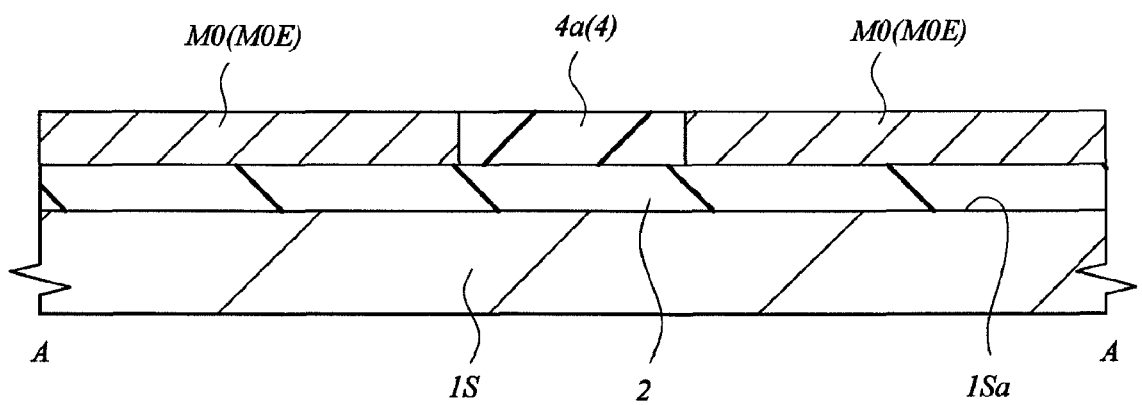
FIG. 10 is a cross-sectional view of the main portion of the semiconductor device during the manufacturing processing continued from FIG. 9.

Next, as shown in FIG. 10, the insulator film 4 over the upper surface of the lower electrode wirings M0 is removed by a CMP (Chemical Mechanical Polishing) method, an etch back method or the like to expose the upper surface of the lower electrode wirings M0 and the insulator film 4 is left between the adjacent lower electrode wirings M0. The insulator film 4 left between adjacent lower electrode wirings M0 serves as the insulator film (buried insulating film) 4a filling the space between the lower electrode wirings M0.

Figure 11:
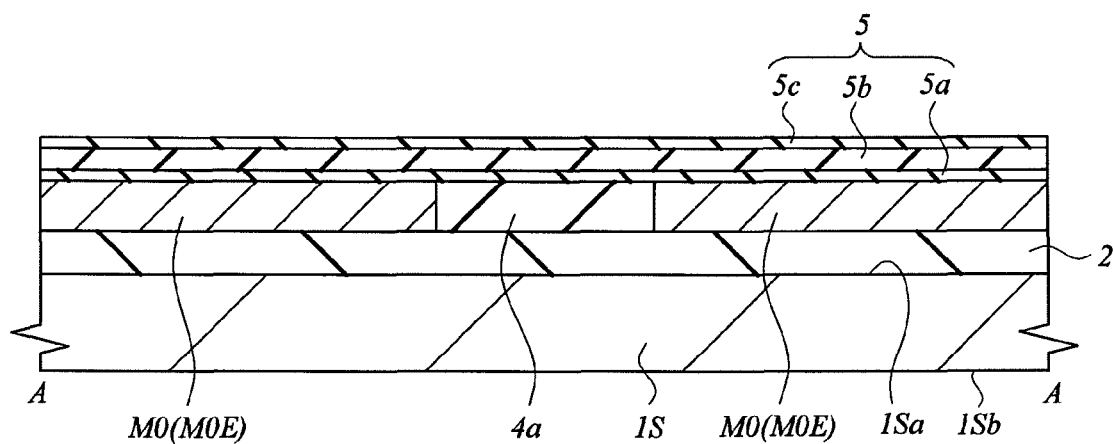
FIG. 11 is a cross-sectional view of the main portion of the semiconductor device during the manufacturing processing continued from FIG. 10.

Next, as shown in FIG. 11, over the entire surface of the first main surface of the semiconductor substrate 1S (that is, over the upper surfaces of the lower electrode wirings M0 and the upper surface of the insulator film 4a filling the space between the lower electrode wirings M0), the insulator film 5 is formed (deposited) so as to cover the lower electrode wirings M0 (lower electrodes M0E) and the insulator film 4a filling the space between the lower electrode wirings M0.

In the present embodiment, the insulator film 5 is composed of a stacked film of the silicon oxide film 5a, the silicon nitride film 5b and the silicon oxide film 5c sequentially from below. That is, over the entire surface of the first main surface of the semiconductor substrate 1S (that is, over the upper surfaces of the lower electrode wirings M0 and the upper surface of the insulator film 4a filling the space between the lower electrode wirings M0), the silicon oxide film 5a is formed (deposited) using the plasma-enhanced CVD method or the like, the silicon nitride film 5b is formed (deposited) over the silicon oxide film 5a using the plasma-enhanced CVD method or the like and the silicon oxide film 5c is formed (deposited) over the silicon nitride film 5b using the plasma-enhanced CVD method or the like. A film thickness (deposition thickness) of the silicon oxide film 5a can be approximately 50 nm, for example. A film thickness (deposition thickness) of the silicon nitride film 5b can be approximately 175 nm, for example. And a film thickness (deposition thickness) of the silicon oxide film 5c can be approximately 50 nm, for example.

Figure 12:
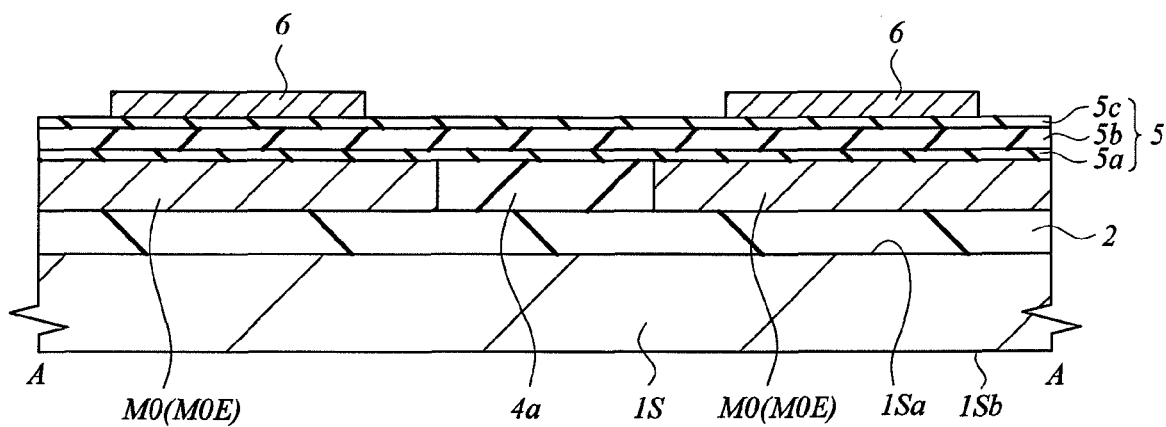
FIG. 12 is a cross-sectional view of the main portion of the semiconductor device during the manufacturing processing continued from FIG. 11.

Next, as shown in FIG. 12, over the entire surface over the insulator film 5 of the first main surface 1Sa of the semiconductor substrate 1S, a sacrificial film composed of, for example, an amorphous silicon film, is formed (deposited) using the plasma-enhanced CVD method, and then, by patterning this sacrificial film using the lithography method and the dry etching method, a sacrificial film pattern (sacrificial film pattern for formation of the voids) 6 is formed. The sacrificial film pattern 6 is formed over the insulator film 5 over the lower electrode wirings M0 (lower electrodes M0E). The sacrificial film pattern 6 is a pattern for forming the voids VR, and a plane pattern of the sacrificial film pattern 6 is formed in a plane shape same as that of the voids VR. Therefore, the sacrificial film pattern 6 is formed in a region where the voids VR are supposed to be formed.

Figure 13:
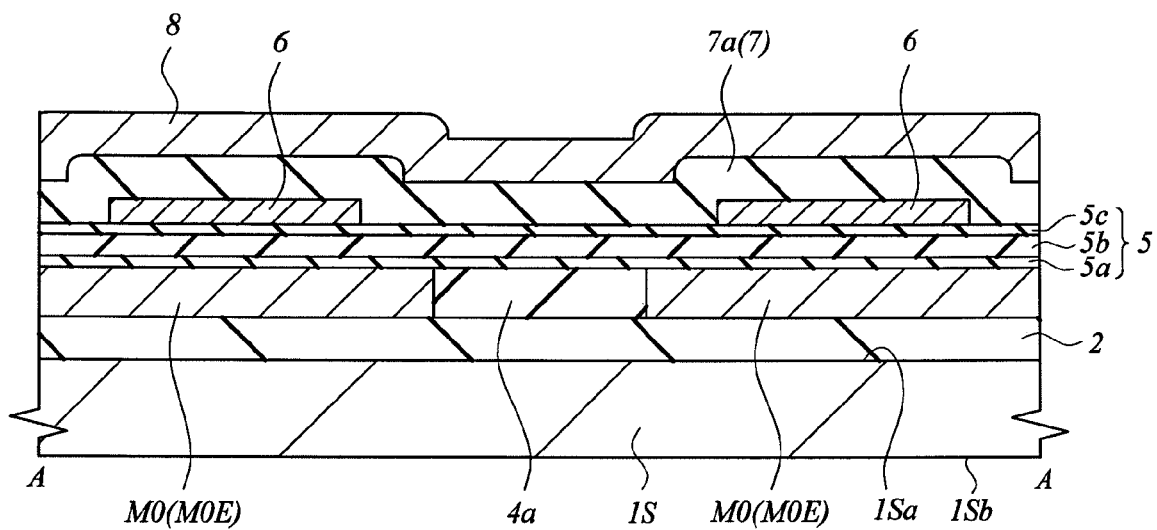
FIG. 13 is a cross-sectional view of the main portion of the semiconductor device during the manufacturing processing continued from FIG. 12.

Next, as shown in FIG. 13, over the entire surface over the first main surface 1Sa of the semiconductor substrate 1S (that is, over the insulator film 5), the insulator film 7 is formed (deposited) so as to cover the surface of the sacrificial film pattern 6. In the present embodiment, the insulator film 7 is composed of a single layer film (single film, single layer) of the silicon oxide film 7a, and can be formed using the plasma-enhanced CVD method or the like. A film thickness (deposition thickness) of the insulator film 7 can be set to approximately 200 nm, for example.

Next, over the insulator film 7, a conductive film (conductive layer) 8 for formation of the upper electrode wirings is formed (deposited). The conductive film 8 is formed over the entire surface of the first main surface 1Sa of the semiconductor substrate 1S. The conductive film 8 is formed of a metal film or a film having metallic conduction, such as a stacked film of a titanium nitride (TiN) film, an aluminum (Al) film, and a titanium nitride (TiN) film sequentially formed from below. This aluminum film is composed of a conductive film containing aluminum as a main ingredient, such as the aluminum single film or the aluminum alloy film. The conductive film 8 can be formed using the sputtering method or the like. A thickness of the conductive film 8 for the formation of the upper electrode wirings is smaller than the thickness of the conductive film 3 for the formation of the lower electrode wirings, and can be approximately 400 nm. And, in a case where the conductive film 8 is a stacked film of a titanium nitride film, an aluminum film and a titanium nitride film, the aluminum film serves as a main conductive film of the upper electrode wiring M1. Therefore, a film thickness of the aluminum film can be larger than a film thickness of the titanium nitride film. For example, the film thickness of the aluminum film can be approximately 300 nm, the film thickness of each of the titanium nitride films above and below the aluminum film can be approximately 50 nm. And, in place of the titanium nitride film, a stacked film of a titanium (Ti) film and a titanium nitride film or a tungsten (W) film can be used.

Figure 14:
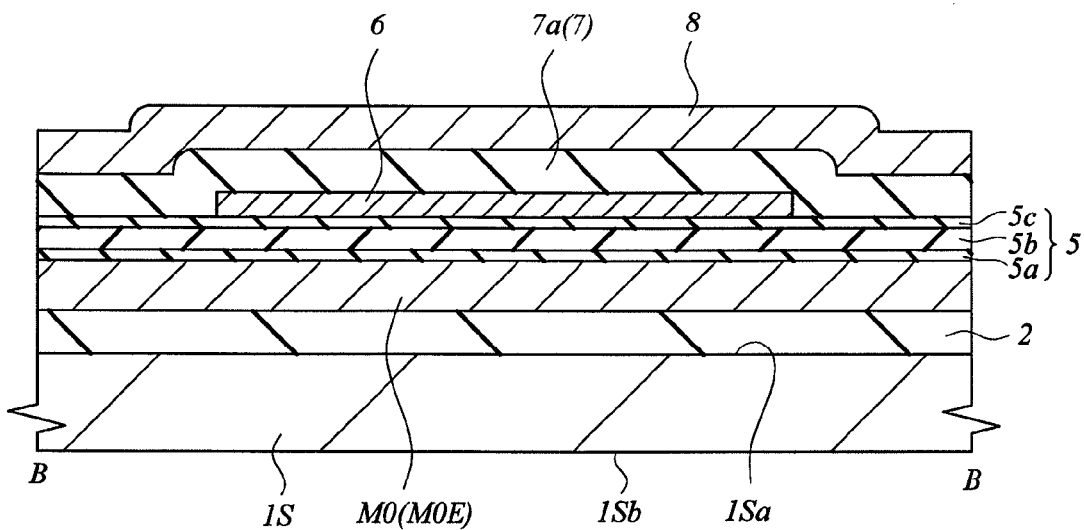
FIG. 14 is another cross-sectional view of the main portion during the same manufacturing processing as that of FIG. 13.

FIG. 14 is a main portion cross-sectional view showing a manufacturing processing stage same as that in FIG. 13 (a stage where the conductive film 8 is formed). As described above, while FIGS. 7 to 13 show a region corresponding to FIG. 5, FIG. 14 and FIGS. 15 to 18 thereafter show a region corresponding to FIG. 6.

Figure 15:
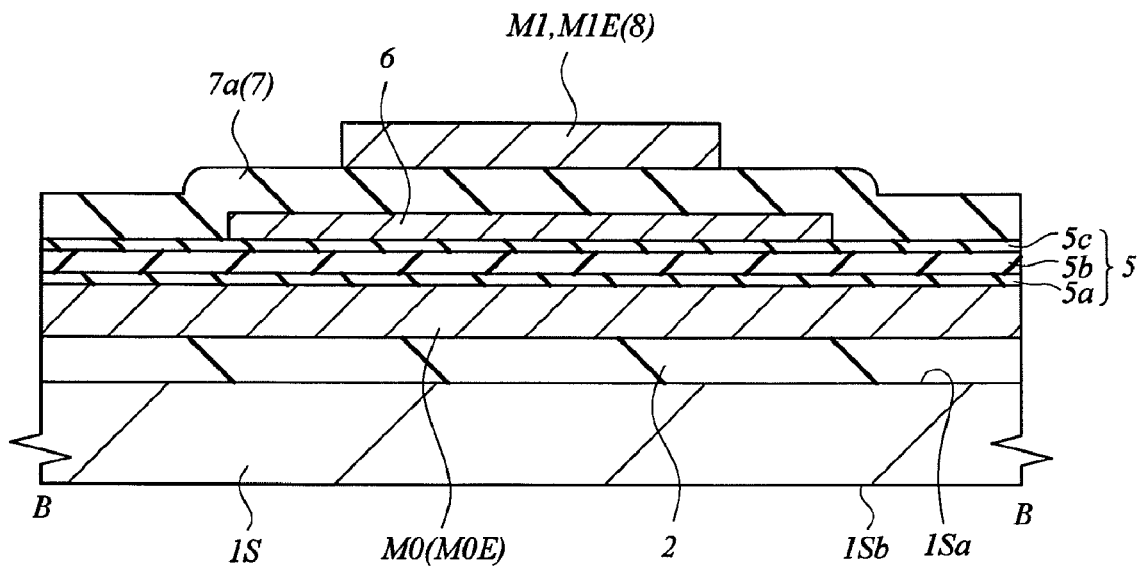
FIG. 15 is a cross-sectional view of the main portion of the semiconductor device during the manufacturing processing continued from FIG. 14.

After the conductive film 8 is formed as shown in FIGS. 13 and 14, the conductive film 8 is patterned (processed) using the lithography method, the dry etching method or the like as shown in FIG. 15. By the patterned conductive film 8, the upper electrode wirings M1 (upper electrodes M1E and connecting portion M1C) are formed. Thereby, the upper electrode wirings M1 are formed over the insulator film 7.

Figure 16:
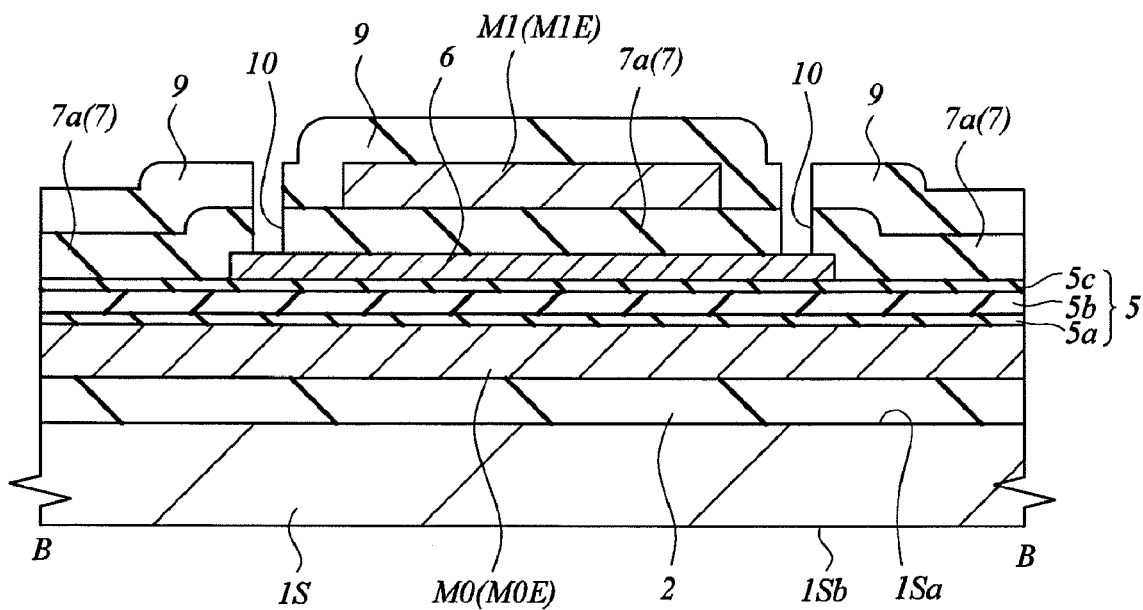
FIG. 16 is a cross-sectional view of the main portion of the semiconductor device during the manufacturing processing continued from FIG. 15.

Next, as shown in FIG. 16, over the entire surface over the first main surface 1Sa of the semiconductor substrate 1S (that is, over the insulator film 7), the insulator film 9 is formed (deposited) so as to cover the upper electrode wirings M1 (upper electrodes M1E). The insulator film 9 is composed of a silicon nitride film or the like, and can be formed using the plasma-enhanced CVD method or the like. And, a thickness of the insulator film 9 can be approximately 500 nm, for example.

Next, using the lithography method and the dry etching method, holes (openings, via holes) 10 are formed in the insulator films 9 and 7 so as to reach the sacrificial film pattern 6 to expose a part of the sacrificial film pattern 6. The holes 10 are formed at positions superposing on the sacrificial film pattern 6 in a plane manner, and the part of the sacrificial film pattern 6 is exposed in bottom portions of the holes 10.

Figure 17:
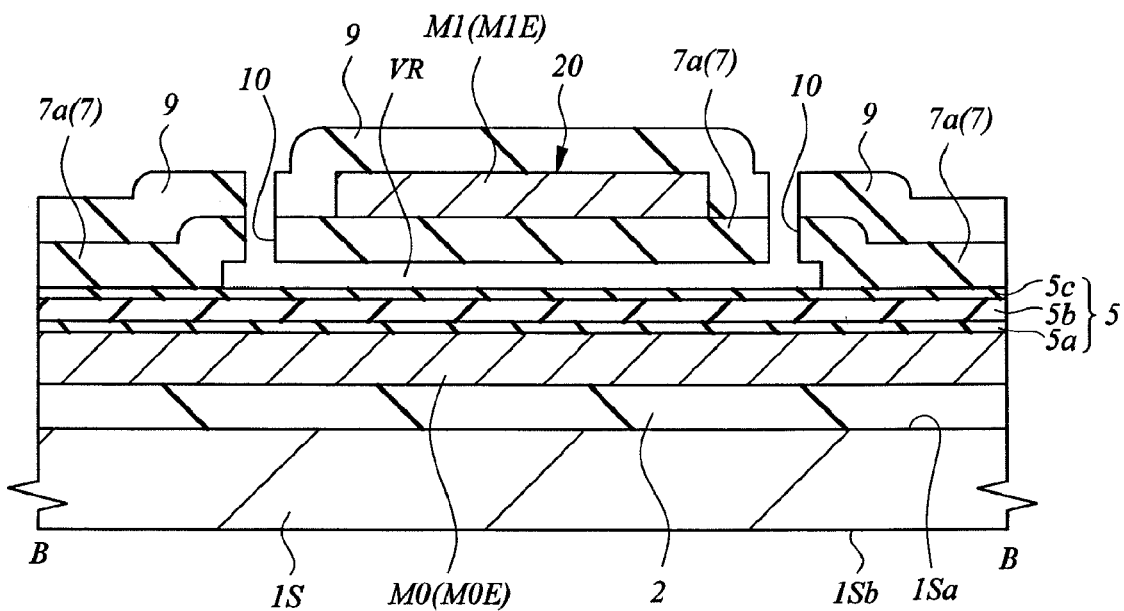
FIG. 17 is a cross-sectional view of the main portion of the semiconductor device during the manufacturing processing continued from FIG. 16.

Next, via the holes 10, the sacrificial film pattern 6 is selectively etched by the dry etching method using xenon fluoride ($XeF_2$), for example. Thereby, as shown in FIG. 17, the sacrificial film pattern 6 is selectively removed and regions where the sacrificial film pattern 6 existed before become the voids VR, and the voids VR are formed between the insulator film 5 and the insulator film 7. That is, in the CMUT region CA, the voids VR are formed in a space between facing surfaces of the lower electrode wirings M0 (lower electrodes M0E) and the upper electrode wirings M1 (upper electrodes M1E).

As described above, by selectively etching the sacrificial film pattern 6 between the insulator films 5 and 7 via the holes 10, the voids VR can be formed between the lower electrode wirings M0 and the upper electrode wirings M1. Other than the dry etching using xenon fluoride ($XeF_2$), a dry etching method using $ClF_3$ or the like can be used for etching the sacrificial film pattern 6 to form the voids VR.

Note that, in the lower electrode wirings M0, portions facing the upper electrode wirings M1 via the voids VR are the lower electrodes M0E. In the upper electrode wirings M1, portions facing the lower electrode wirings M0 via the voids VR are the upper electrodes M1E.

Figure 18:
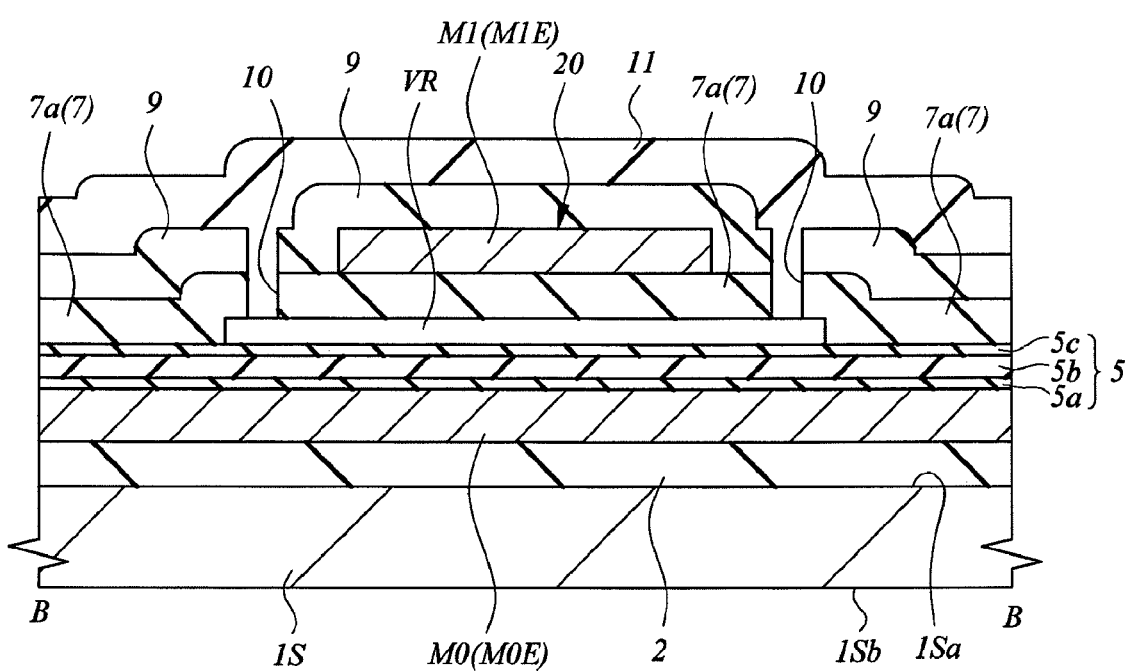
FIG. 18 is a cross-sectional view of the main portion of the semiconductor device during the manufacturing processing continued from FIG. 17.

Next, as shown in FIG. 18, over the entire surface over the first main surface 1Sa of the semiconductor substrate 1S (that is, over the insulator film 9), the insulator film 11 is formed (deposited). Thereby, parts of the insulator film 11 are buried in the holes 10 to block the holes 10. The insulator film 11 is composed of a silicon nitride film, for example, and can be formed using the plasma-enhanced CVD method or the like. And, a thickness of the insulator film 11 can be approximately 800 nm, for example. In this manner, the capacitance type transducer 20 is formed.

Thereafter, by the lithography method and the dry etching method, an opening for the pad BP1 (not shown) is formed in the insulator films 11, 9, 7 and 5 so as to expose a part of the lower electrode wirings M0, and an opening for the pad BP2 (not shown) is formed so as to expose a part of the upper electrode wirings M1. Then, as shown in FIGS. 5 and 6, over the entire surface over the first main surface 1Sa of the semiconductor substrate 1S (that is, over the insulator film 11), the insulator film 13 composed of a photosensitive polyimide film, for example is formed. Then, by exposure and development processing, openings for the pads BP1 and BP2 (not shown) are formed in the insulator film 13 so as to expose parts of the lower electrode wirings M0 and the upper electrode wirings M1. The parts of the lower electrode wirings M0 exposed from the openings in the insulator films 5, 7, 9, 11 and 13 become the pads BP1, and parts of the upper electrode wirings M1 exposed from the openings in the insulator films 9, 11 and 13 become the pads BP2. Then, respective chip regions are cut out from the semiconductor substrate 1S (semiconductor wafer) through a dicing processing, thereby manufacturing the semiconductor chip 1.

Next, effects of the present embodiment are described in more detail.

In the ultrasonic transducer having configurations shown in FIGS. 1 to 6, the insulator film 7, the upper electrode M1E and the insulator films 9, 11, and 13 thereabove configure the membrane, and this membrane vibrates. If a DC voltage and an AC voltage are applied in a superposed manner to the lower electrode wirings M0 (lower electrodes M0E) and the upper electrode wirings M1 (upper electrodes M1E), an electrostatic force works between the lower electrode wirings M0 (lower electrodes M0E) and the upper electrode wirings M1 (upper electrodes M1E). (The stacked layer of) the insulator film 7, the upper electrode wirings M1 (upper electrodes M1E) and the insulator films 9, 11, and 13 configuring the membrane over the void VR vibrate at a frequency of the applied AC voltage in a direction crossing the first main surface 1Sa of the semiconductor substrate 1S, thereby transmitting (sending) the ultrasonic wave. To the lower electrode wirings M0, voltages can be applied via the pads BP1. To the upper electrode wirings M1, voltages can be applied via the pads BP2.

Conversely, when the ultrasonic wave is to be received, the membrane over the void VR of each transducer 20 vibrates by a pressure of the ultrasonic wave having reached the surface of the CMUT region CA of the semiconductor chip 1. By this vibration, a distance (space) between the upper electrode M1E and the lower electrode M0E is changed, and the ultrasonic wave can be detected as change of electric capacity between the upper electrode M1E and the lower electrode M0E. That is, because of change of the distance (space) between the upper and lower electrodes (the upper electrode M1E and the lower electrode M0E), the electric capacity between the electrodes is changed, and a current is carried. By detecting this current, the ultrasonic wave can be detected.

In the CMUT region CA, transmission (sending) and reception of the ultrasonic wave are performed using the vibration of the membrane due to an electrostatic force caused by voltage application between the upper electrode M1E and the lower electrode M0E and the change of the electric capacity between the upper electrode M1E and the lower electrode M0E due to the vibration of the membrane. The voltage applied between the upper electrode M1E and the lower electrode M0E is as high as 100V or more, and therefore, improvement of the breakdown voltage between the upper electrode M1E (upper electrode wiring M1) and the lower electrode M0E (lower electrode wiring M0) is important.

Figure 19:
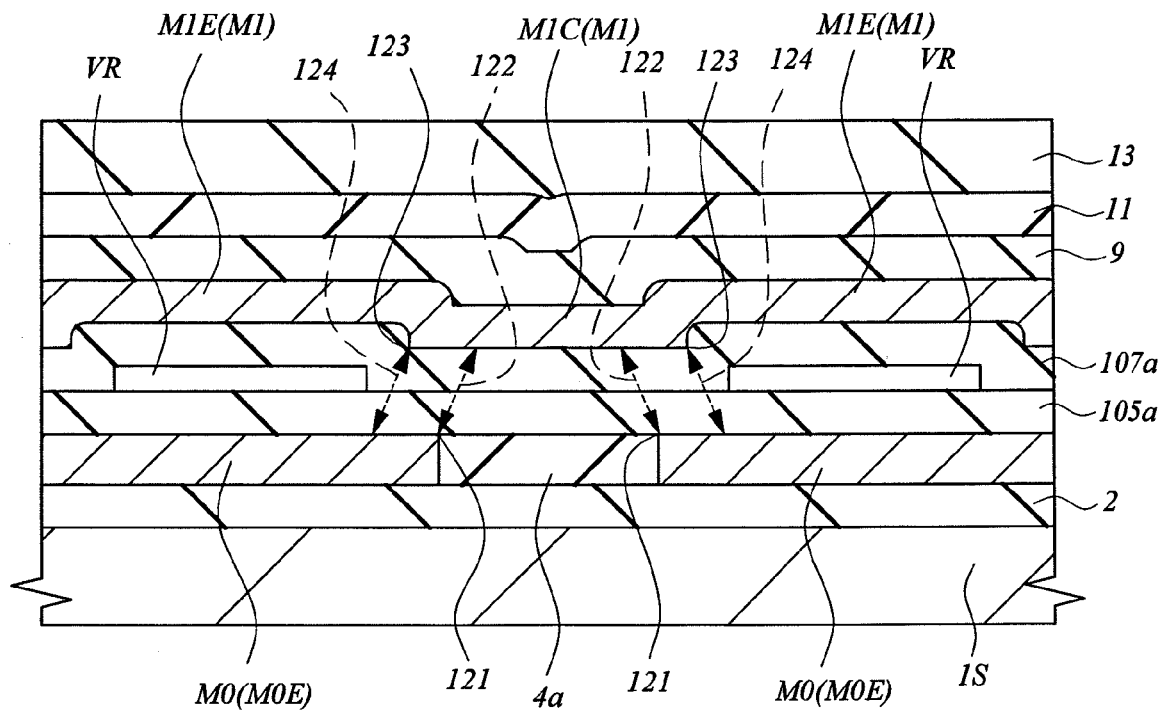
FIG. 19 is a cross-sectional view of a main portion of a semiconductor device of a first comparison example.
Figure 20:
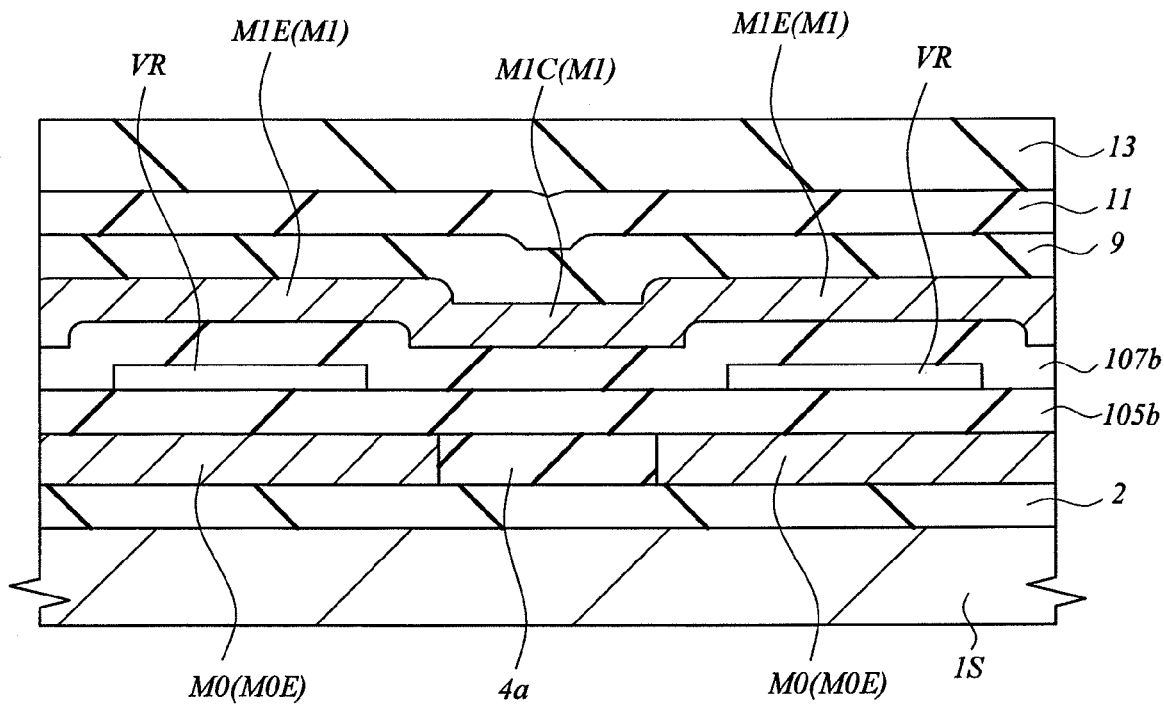
FIG. 20 is a cross-sectional view of a main portion of a semiconductor device of a second comparison example

FIG. 19 is a main portion cross-sectional view of a semiconductor device examined by the inventors as a first comparison example. FIG. 20 is a main portion cross-sectional view of a semiconductor device examined by the inventors as a second comparison example. Both correspond to FIG. 5 according to the present embodiment.

In the first comparison example of FIG. 19, unlike the present embodiment, one corresponding to the insulator film 5 in the present embodiment is a single layer film of the silicon oxide film 105a, and one corresponding to the insulator film 7 in the present embodiment is a single layer film of the silicon oxide film 107a. In the second comparison example of FIG. 20, unlike the present embodiment, one corresponding to the insulator film 5 in the present embodiment is a single layer film of the silicon nitride film 105b, and one corresponding to the insulator film 7 in the present embodiment is a single layer film of the silicon nitride film 107b. Configurations other than the insulator films 5 and 7 of the first comparison example in FIG. 19 and the second comparison example in FIG. 20 are approximately similar to those of the semiconductor device according to the present embodiment, and therefore, explanations thereof are omitted herein.

When a voltage is applied between the electrodes facing each other, an electric field tends to be enhanced at a sharp portion more than a flat surface of the electrodes. Therefore, in the lower electrode wiring M0 (lower electrode M0E), the electric field tends to be enhanced at an edge of upper surface 121 of the lower electrode wiring M0 (lower electrode M0E) shown in FIG. 19. For this reason, a leakage current or dielectric breakdown between the upper and lower electrodes tend to occur on a route having this edge of upper surface 121 as a starting point or an ending point, for example, a route 122 indicated by an arrow in FIG. 19. And, in the upper electrode wiring M1 (upper electrode M1E), the electric field tends to be enhanced at a step (corner, step corner) 123 over the lower surface formed due to the void VR. For this reason, the leakage current and the dielectric breakdown between the upper and lower electrodes tend to occur on a route having this step 123 as a starting point or an ending point, for example, a route 124 indicated by an arrow in FIG. 19.

If insulator films interposed between the upper electrode wiring M1 and the lower electrode wiring M0 (corresponding to the insulator films 5 and 7 in the present embodiment) are restricted to the silicon oxide films 105a and 107a as in the first comparison example of FIG. 19, due to influence of electric field enhancement at the edge of upper surface 121 of the lower electrode wiring M0 and the step 123 over the lower surface of the upper electrode wiring M1, the breakdown voltage between the lower electrode wiring M0 and the upper electrode wiring M1 is decreased, the leakage currents between the upper and lower electrodes on the route 122 and the route 123 in FIG. 19 are increased and the dielectric breakdown becomes easy to occur. This can be considered due to the Fowler-Nordheim tunneling conduction in which a conduction mechanism of the silicon oxide film strongly depends on the electric field.

On the other hand, if the insulator films interposed between the upper electrode wiring M1 and the lower electrode wiring M0 (corresponding to the insulator films 5 and 7 in the present embodiment) are restricted to the silicon nitride films 105b and 107b as in the second comparison example of FIG. 20, a configuration in which the upper electrode M1E and the lower electrode M0E make direct contact with the silicon nitride films 107a and 105a is obtained. Therefore, by the leakage current between the upper electrode M1E (upper electrode wiring M1) and the lower electrode M0E (lower electrode wiring M0), charges are trapped in the silicon nitride films 105b and 107b (one or both of the silicon nitride films 105b and 107b). It is found by the inventors that, if the charges are trapped in the silicon nitride films 105b and 107b, a capacitance-voltage characteristic of the transducer 20 composed of the upper electrode M1E and the lower electrode M0E is changed, and as a result, the transmitting/receiving gain of the CMUT region CA fluctuates.

On the other hand, in the present embodiment, as shown also in FIGS. 5 and 6, although the insulator films 5 and 7 are interposed between the upper electrode wiring M1 (upper electrode M1E) and the lower electrode wiring M0 (lower electrode M0E), the insulator film 5 is a stacked film of the silicon oxide film 5a, the silicon nitride film 5b and the silicon oxide film 5c and the insulator film 7 is the silicon oxide film 7a. Therefore, the present embodiment employs a configuration in which both of the silicon oxide film and the silicon nitride film are interposed between the upper electrode wiring M1 (upper electrode M1E) and the lower electrode wiring M0 (lower electrode M0E), the upper surface of the lower electrode M0E (lower electrode wiring M0) is in contact with the silicon oxide film (here, the silicon oxide film 5a) but is not in contact with the silicon nitride film (here, the silicon nitride film 5b), and the lower surface of the upper electrode M1E (upper electrode wiring M1) is in contact with the silicon oxide film (here, the silicon oxide film 7a) but is not in contact with the silicon oxide film (here, the silicon nitride film 5b).

Figure 21:
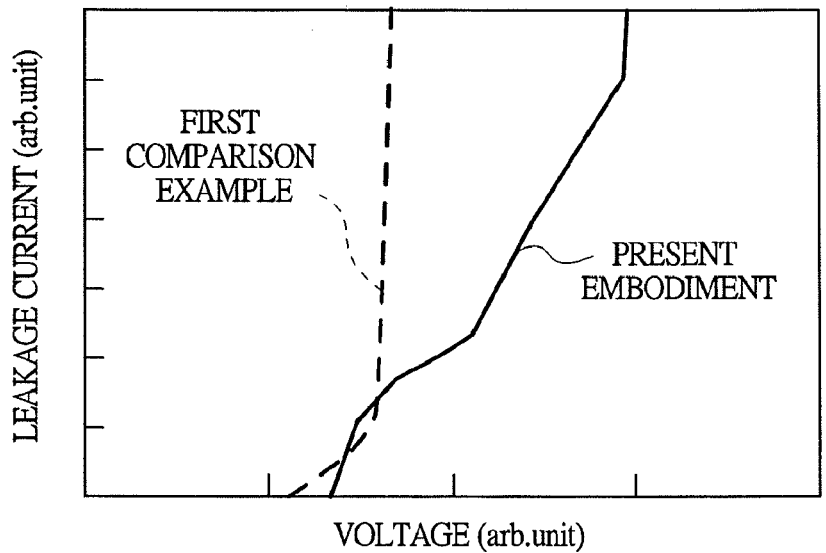
FIG. 21 is a graph showing a result of evaluation of a breakdown voltage of an insulator film between electrodes.

FIG. 21 is a graph showing a result of evaluation of a breakdown voltage of the insulator films between the upper electrode wiring M1 and the lower electrode wiring M0. A horizontal axis of the graph in FIG. 21 represents a voltage (in arbitrary unit) applied between the upper electrode M1E and the lower electrode M0E, and a vertical axis of the graph in FIG. 21 represents a leakage current (in arbitrary unit) between the upper electrode M1E (upper electrode wiring M1) and the lower electrode M0E (lower electrode wiring M0). Note that, the vertical axis in FIG. 21 is logarithmic. And, the graph of FIG. 21 shows a case of the present embodiment employing the configuration shown in FIGS. 5 and 6 (in the graph of FIG. 21, denoted in a solid line as "present embodiment") and a case of the first comparison example employing the configuration shown in FIG. 19 (in the graph of FIG. 21, denoted in a dotted line as "first comparison example"). Note that, a thickness of the silicon oxide film 7a for the insulator film 7 in the case of the "present embodiment" shown in the graph of FIG. 21 is made equal to a thickness of the silicon oxide film 107 in the case of the "first comparison example", and a total thickness of the stacked film of the silicon oxide film 5a, the silicon nitride film 5b and the silicon oxide film 5c for the insulator film 5 in the case of the "present embodiment" and the thickness of the silicon oxide film 105a in the case of the "first comparison example" are adjusted so that a capacitance value between the upper electrode M1E and the lower electrode M0E is the same between the case of the "present embodiment" and the case of the "first comparison example".

As evident from the graph of FIG. 21, in comparison with the first comparison example in which only the silicon oxide film is used as the insulator film between the upper electrode wiring M1 and the lower electrode wiring M0, the dielectric breakdown voltage between the upper and lower electrodes is significantly improved in the present embodiment in which the stacked film of the silicon oxide film 5a, the silicon nitride film 5b and the silicon oxide film 5c and the silicon oxide film 7a are used as the insulator films 5 and 7 between the upper electrode wiring M1 and the lower electrode wiring M0. A reason thereof can be considered to that the conduction mechanism of the insulator films between the upper electrode wiring M1 (upper electrode M1E) and the lower electrode wiring M0 (lower electrode M0E) is changed from a Fowler-Nordheim type composed of only the silicon oxide films 105a and 107a in the case of the first comparison example to a Poole-Frenkel type using trapping in the silicon nitride film 5b in the present embodiment. In conduction of the Poole-Frenkel type, electric-field dependence of the insular film is small, and therefore, the electric-field enhancement at the edge of upper surface 121 of the lower electrode wiring M0 and the step 123 over the lower surface of the upper electrode wiring M1 has little influence.

As described above, in the present embodiment, since the silicon nitride film 5b is interposed between the upper and lower electrodes, the conduction mechanism of the insulator films between the upper electrode wiring M1 (upper electrode M1E) and the lower electrode wiring M0 (lower electrode M0E) becomes the Poole-Frenkel type, no influence of the electric-field enhancement at portions corresponding to the edge of upper surface 121 and the step 123 works, and therefore, the leakage current or the dielectric breakdown on the routes 122 and 124 having these portions as a start point or an end point can be suppressed or prevented. Thereby, performance of the semiconductor chip 1 comprising the CMUT cell array can be improved and a manufacturing yield can be increased.

Figure 22:
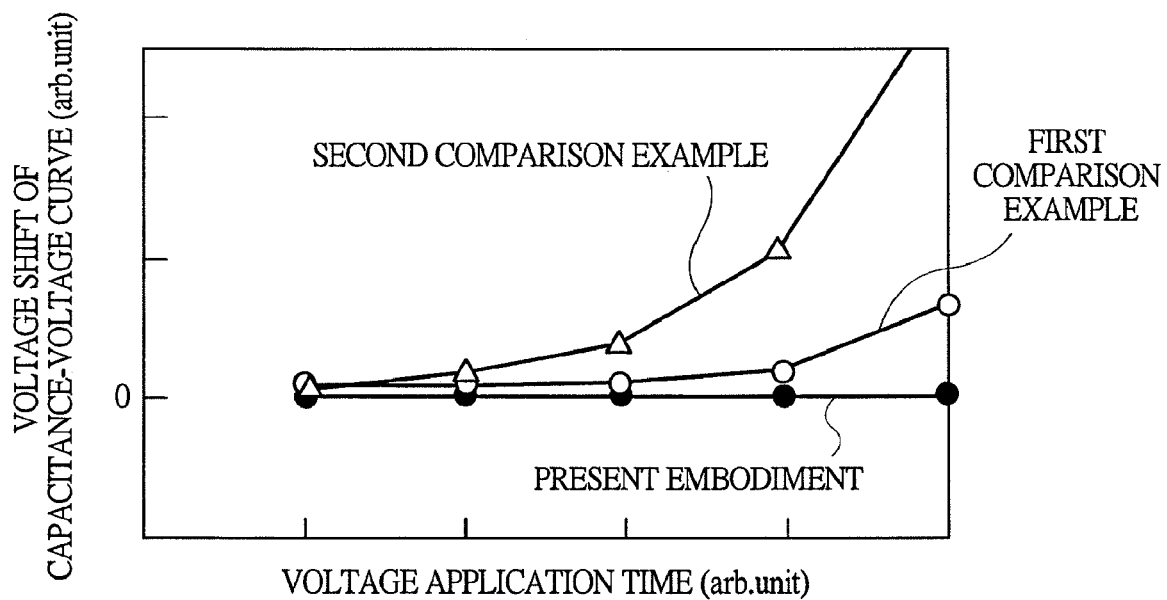
FIG. 22 is a graph showing a result of application of a voltage between electrodes for long time and measurement of an amount of shift of a capacitance-voltage curve.

FIG. 22 is a graph showing a result obtained by applying a drive voltage at actual operation between the upper electrode M1E and the lower electrode M0E of the CMUT cell and measuring an amount of shift of a capacitance-voltage curve. A horizontal axis of the graph in FIG. 22 corresponds a voltage application time (in arbitrary unit) between the upper electrode M1E and the lower electrode M0E, and a vertical axis of the graph in FIG. 22 corresponds a voltage shift (in arbitrary unit) of the capacitance-voltage curve (C-V curve) before and after voltage application. Note that, the horizontal axis in FIG. 22 is logarithmic. And, the graph of FIG. 22 shows a case of a configuration according to the present embodiment shown in FIGS. 5 and 6 (in the graph of FIG. 22, denoted as "present embodiment" with black circles), a case of a configuration according to the first comparison example shown in FIG. 19 (in the graph of FIG. 22, denoted as "first comparison example" with white circles), and a case of a configuration according to the second comparison example shown in FIG. 20 (in the graph of FIG. 22, denoted as "second comparison example" with white triangles). Note that, a thickness of each of the insulator films 5 and 7 in the case of the "present embodiment", a thickness of each of the silicon oxide films 105a and 107a in the case of the "first comparison example", and thickness of each of the silicon nitride films 105b and 107b in the case of the "second comparison example" shown in the graph of FIG. 22 are adjusted so that the capacitance value between the upper electrode M1E and the lower electrode M0E is the same among the case of the "present embodiment", the case of the "first comparison example" and the case of the "second comparison example".

Figure 23:
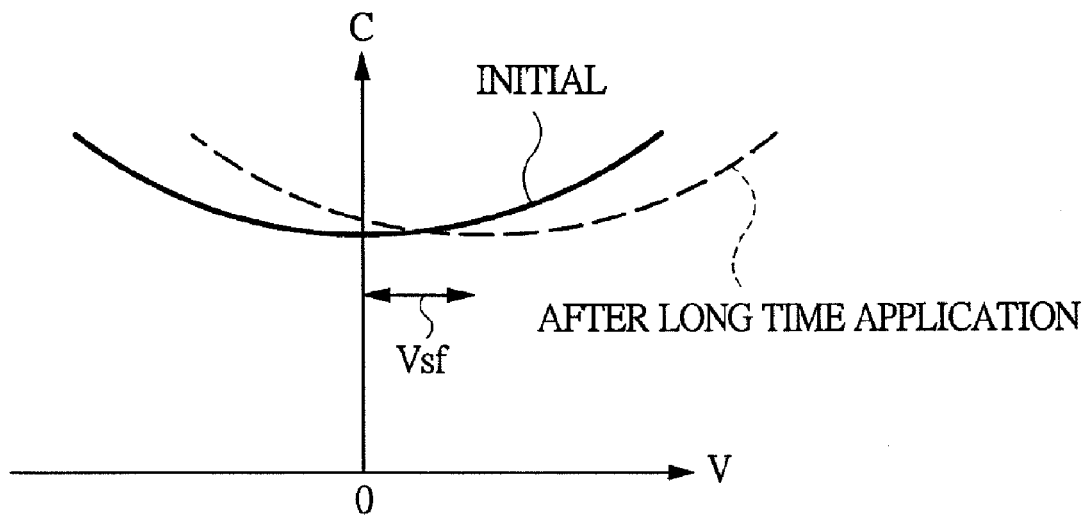
FIG. 23 is a graph schematically showing capacitance-voltage curves (C-V curves) before and after the application of the voltage between the electrodes for the long time.

And, FIG. 23 is a graph schematically showing a capacitance-voltage curve (C-V curve) before and after application of the drive voltage at the actual operation between the upper electrode M1E and the lower electrode M0E for a long time. In the graph of FIG. 23, an initial capacitance-voltage curve (C-V curve) is schematically represented as a solid line, and a capacitance-voltage curve (C-V curve) after the application of the drive voltage at the actual operation between the upper electrode M1E and the lower electrode M0E for a long time is schematically represented as a dotted line. An amount of shift from the initial capacitance-voltage curve (C-V curve) is represented as a voltage shift Vsf. The value of this voltage shift Vsf corresponds to the vertical axis of the graph in FIG. 22.

In the present embodiment in which the insulator film between the upper electrode wiring M1 (upper electrode M1E) and the lower electrode wiring M0 (lower electrode M0E) is composed of a stacked layer of the silicon oxide film 5a, the silicon nitride film 5b and the silicon oxide film 5c and the silicon oxide film 7a, as evident from the graph of FIG. 22, no shift in the capacitance-voltage curve is observed within an observation time (that is, an amount of voltage shift Vsf is approximately zero). On the other hand, as in the first comparison example, when only the silicon oxide films 105a and 107a are used as the insulator film between the upper electrode wiring M1 (upper electrode M1E) and the lower electrode wiring M0 (lower electrode M0E), as represented in the graph of FIG. 22, a slight shift was observed in the capacitance-voltage curve. On the other hand, as in the second comparison example, when only the silicon nitride films 105b and 107b are used as the insulator film between the upper electrode wiring M1 (upper electrode M1E) and the lower electrode wiring M0 (lower electrode M0E), as represented in the graph of FIG. 22, a large voltage shift is observed in the capacitance-voltage curve. Occurrence of the voltage shift in the capacitance-voltage curve means that, when the CMUT cell is repeatedly operated, the transmitting/receiving gain is deteriorated.

Since a large amount of charge traps exists in the silicon nitride film, when the CMUT employs a configuration in which the electrodes (here, the lower electrode M0E or the upper electrode M1E) and the silicon nitride films (here, the silicon nitride films 105b, 107b) directly make contact with each other as in the second comparison example, a hole current flows and the charges are trapped in the silicon nitride films. As a result, the capacitance-voltage curve is considered to shift. Consequently, as shown in the graph of FIG. 22, a large voltage shift occurs in the capacitance-voltage curve in the second comparison example.

On the other hand, as in the present embodiment, when the configuration in which the silicon nitride film 5b is interposed between the silicon oxide film 5a and the silicon oxide film 5c to form a stacked structure is employed, the silicon nitride film 5b contacts with neither the upper electrode M1E (upper electrode wiring M1) nor the lower electrode M0E (lower electrode wiring M0), and the hole current can be suppressed. Therefore, it can be considered that a capacitance shift caused by charge trapping in the insulator film due to the leakage current can be suppressed or prevented. Accordingly, in the present embodiment, even if a drive voltage at the actual operation is applied between the upper electrode M1E (upper electrode wiring M1) and the lower electrode M0E (lower electrode wiring M0) for a long time, occurrence of the voltage shift in the capacitance-voltage curve can be suppressed or prevented, and the fluctuation of the transmitting/receiving gain at repeated operation of the CMUT cell can be suppressed or prevented. Therefore, performance of the semiconductor chip 1 comprising the CMUT cell array can be improved.

Next, a case where the semiconductor device (semiconductor chip 1) according to the present embodiment is applied to, for example, an ultrasonic medical imaging system is explained.

Figure 24:
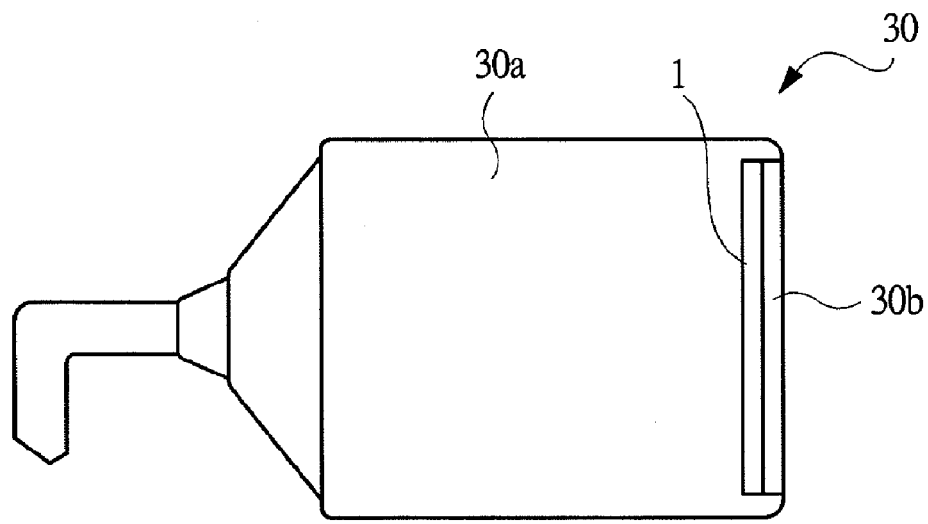
FIG. 24 is an explanation diagram of an ultrasonic medical imaging system having the semiconductor device according to an embodiment of the present invention applied.

The ultrasonic medical imaging system is a medical diagnostic system using permeableness of acoustic waves and making the inside of a body that cannot be viewed from outside visible on a real-time using the ultrasonic wave over an audible sound region. A probe of this ultrasonic medical image system is shown in FIG. 24.

A probe 30 is an ultrasonic-wave transmitting/receiving part. As shown in FIG. 24, on an end surface of a probe case 30a forming the probe 30, the semiconductor chip 1 is mounted with its first main surface (surface over which a plurality of transducers 20 is formed) directed to the outside. Furthermore, this semiconductor chip 1 has an acoustic lens 30b mounted on a first main surface side.

In ultrasonic diagnosis, an end of the probe 30 (on an acoustic lens 30b side) is applied onto a body surface (surface of the body), and is then gradually shifted by a subtle amount for scanning. At this time, an ultrasonic pulse of several MHz is transmitted from the probe 30 applying onto the body surface into the body, and a reflected wave (reflection or echoe) from tissue boundaries having different acoustic impedances is received. With this, a tomographic image of a body tissue is obtained, and information about an objective can be known. From a time interval between transmission of the ultrasonic wave and reception of the reflection, distance information of a reflector can be obtained. And, from a level or an outer shape of the reflected wave, information about existence or quality of the reflector can be obtained.

By applying the semiconductor chip 1 according to the present embodiment to the probe 30 of the ultrasonic medical imaging system, performance and reliability of the probe 30 can be improved.

The specific configuration of the semiconductor device according to the present embodiment has been described. Semiconductor devices according to the present embodiment and the following second to ninth embodiments are semiconductor devices having the lower electrodes M0E (lower electrode wirings M0) and the upper electrodes M1E (upper electrode wirings M1) arranged so as to face each other via the insulators film 5, the voids VR and the insulator film 7. The insulator films 5 are formed over the lower electrodes M0E (lower electrode wirings M0), the insulator films 7 are formed over the insulator film 5, the upper electrodes M1E (upper electrode wirings M1) are formed over the insulator film 7 and the voids VR are formed between the insulator films 5 and the insulator films 7. And, at least portions contacting with the lower electrodes M0E (lower electrode wirings M0) of the insulator films 5 are made of silicon oxide, and at least portions contacting with the upper electrodes M1E (upper electrode wirings M1) of the insulator film 7 are made of silicon oxide. At least one of the insulator films 5 and the insulator films 7 includes a silicon nitride layer portion that is positioned between the lower electrodes M0E (lower electrode wirings M0) and the upper electrodes M1E (upper electrode wirings M1) and is in contact with neither the lower electrodes M0E (lower electrode wirings M0) nor the upper electrodes M1E (upper electrode wirings M1). This silicon nitride layer portion corresponds to the silicon nitride film 5b in the present embodiment and silicon nitride films 5e, 7b and 7e in embodiments described later.

Since at least one of the insulator film 5 and the insulator film 7 includes the silicon nitride layer portion positioned between the lower electrode M0E (lower electrode wiring M0) and the upper electrode M1E (upper electrode wiring M1), this silicon nitride layer portion exists between the upper and lower electrodes, and a conduction mechanism of the insulator films 5 and 7 between the upper electrode M1E (upper electrode wiring M1) and the lower electrode M0E (lower electrode wiring M0) mainly forms a Poole-Frenkel type. Therefore, as described above, the conduction mechanism does not receive influence of the electric-field enhancement at a portion corresponding to the edge of upper surface 121 of the lower electrode wiring M0 and the step 123 of the upper electrode wiring M1, and occurrence of the leakage current or dielectric breakdown between upper and lower electrodes on the routes (routes corresponding to the routes 122 and 124) having the electric-field-enhanced portions (portions corresponding to the edge of upper surface 121 and the step 123) as the starting points or the ending points. With this, the breakdown voltage between the upper electrode M1E (upper electrode wiring M1) and the lower electrode M0E (lower electrode wiring M0) can be improved. Therefore, the performance of the semiconductor device can be improved and the manufacturing yield can be increased.

And, the portion of the insulator film 5 contacting with the lower electrode M0E (lower electrode wiring M0) and the portion of the insulator film 7 contacting with the upper electrode M1E (upper electrode wiring M1) are made of the silicon oxide, and the silicon nitride layer portions included in the insulator films 5, 7 contact with neither the lower electrode M0E nor upper electrode M1E (upper electrode wiring M1). With this, as described above, charge trapping to the silicon nitride layer portion can be suppressed or prevented. Therefore, even if a voltage is applied between the upper electrode M1E and the lower electrode M0E for a long time, charge trapping to the silicon nitride layer portions included in the insulator films 5, 7 can be suppressed or prevented, and fluctuation of a characteristic of the capacitive element (transducer) composed of the lower electrode M0E, the insulator film 5, the void VR, the insulator film 7 and the upper electrode M1E caused by charge trapping to the silicon nitride layer portion can be suppressed or prevented. Thus, the performance of the semiconductor device can be improved.

Therefore, both of improvement of the breakdown voltage between the electrodes of the ultrasonic transducer and suppression of fluctuation in the transmitting/receiving gain caused by the charge trapping of the insulator films can be achieved.

In order to easily and accurately achieve a structure in which the portion of the insulator film 5 contacting with the lower electrode M0E (lower electrode wiring M0) and the portion of the insulator film 7 contacting with the upper electrode M1E (upper electrode wiring M1) are made of silicon oxide, and at least one of the insulator film 5 and the insulator film 7 includes the silicon nitride layer portion contacting with neither the lower electrode M0E (lower electrode wiring M0) nor the upper electrode M1E (upper electrode wiring M1), film structures of the insulator films 5 and 7 are configured as follows.

That is, the insulator film 5 is composed of a stacked film of a first silicon oxide film (the silicon oxide films 5a and 5d correspond thereto) contacting with the lower electrode M0E (lower electrode wiring M0) and a silicon nitride film (the silicon nitride films 5b and 5e correspond thereto) formed over the first silicon oxide film, and the insulator film 7 is composed of a single layer film or a stacked film including a second silicon oxide film (the silicon oxide films 7a, 7c and 7f correspond thereto) contacting with the upper electrode M1E (upper electrode wiring M1). Alternatively, the insulator film 5 is composed of a single layer film or a stacked film including a first silicon oxide film (the silicon oxide films 5a, 5d and 5f correspond thereto) contacting with the lower electrode M0E (lower electrode wiring M0), and the insulator film 7 is composed of a stacked film including a second silicon oxide film (the silicon oxide films 7c and 7f correspond thereto) contacting with the upper electrode M1E (upper electrode wiring M1) and a silicon nitride film (the silicon nitride films 7b and 7e correspond thereto) formed under the second silicon oxide film.

In the present embodiment, the insulator film 5 is composed of a stacked film of the silicon oxide film 5a, the silicon nitride film 5b and the silicon oxide film 5c sequentially stacked from below (a side of the lower electrode M0E), and the insulator film 7 is composed of a single layer film (single layer) of the silicon oxide film 7a. Other embodiments of the film structures of the insulator films 5 and 7 are described in the following second to eighth embodiments. The semiconductor devices according to the following second to eighth embodiments have structures similar to those of the semiconductor device according to the present embodiment except the film structures of the insulator films 5 and 7.

Second Embodiment

Figure 25:
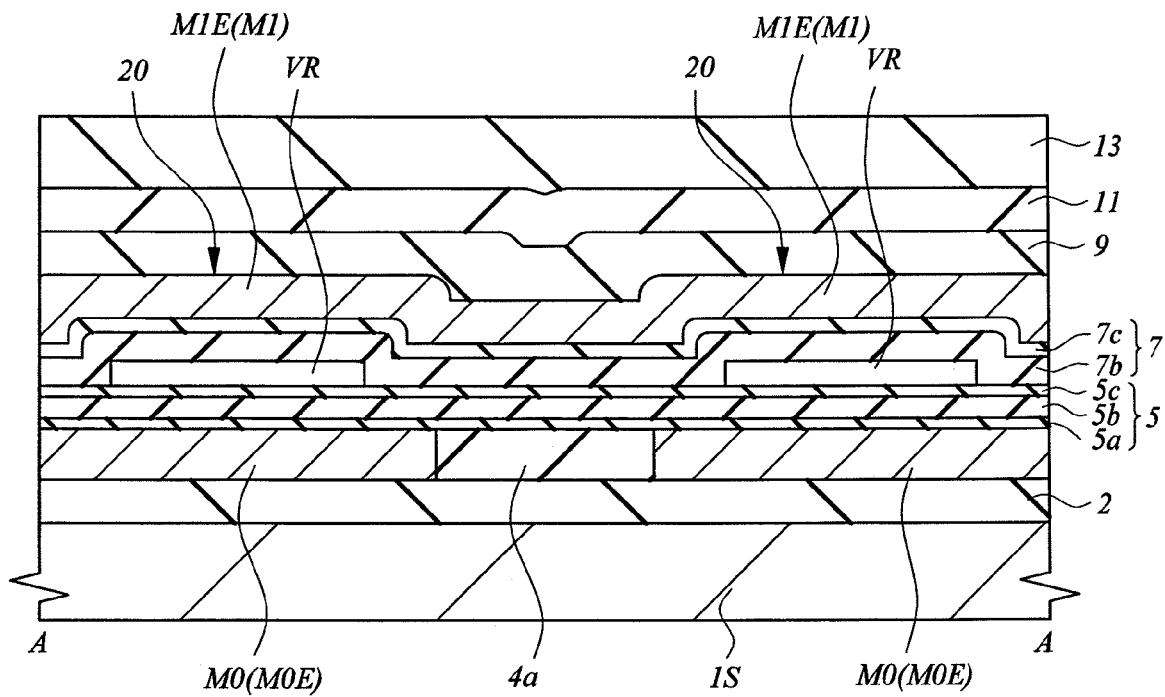
FIG. 25 is a cross-sectional view of a main portion of a semiconductor chip according to a second embodiment of the present invention.
Figure 26:
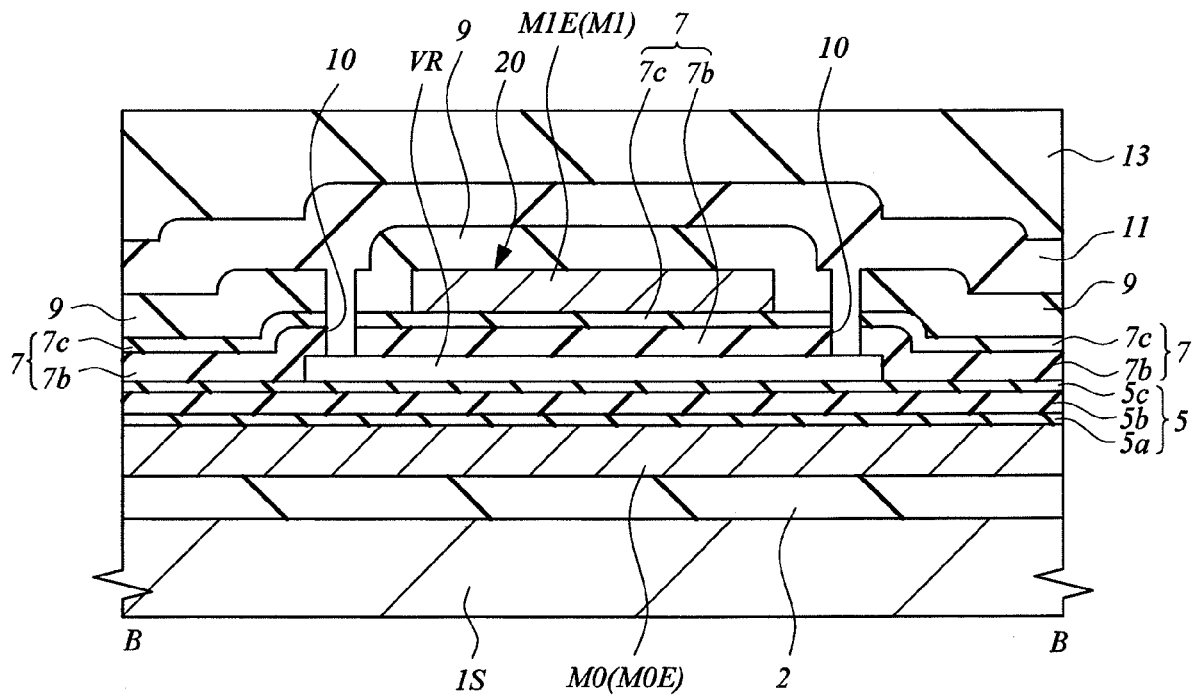
FIG. 26 is a cross-sectional view of the main portion of the semiconductor chip according to the second embodiment of the present invention.

FIGS. 25 and 26 are main portion cross-sectional views of a semiconductor device according to the present embodiment, and correspond to FIGS. 5 and 6 according to the first embodiment respectively.

In the first embodiment, as in FIGS. 5 and 6, the insulator film 5 is composed of a stacked film of the silicon oxide film 5a, the silicon nitride film 5b and the silicon oxide film 5c, and the insulator film 7 is composed of a single layer film (single layer) of the silicon oxide film 7a. On the other hand, in the present embodiment, as shown in FIGS. 25 and 26, although the insulator film 5 is composed of a stacked film of the silicon oxide film 5a, the silicon nitride film 5b and the silicon oxide film 5c in the same way as the first embodiment, the insulator film 7 is composed of, unlike the first embodiment, a stacked film of a silicon nitride film 7b and a silicon oxide film 7c sequentially stacked from below (a side of the insulator film 5). Other than that, a configuration of the semiconductor device according to the present embodiment is similar to that of the first embodiment, and therefore, an explanation thereof is omitted herein.

Figure 27:
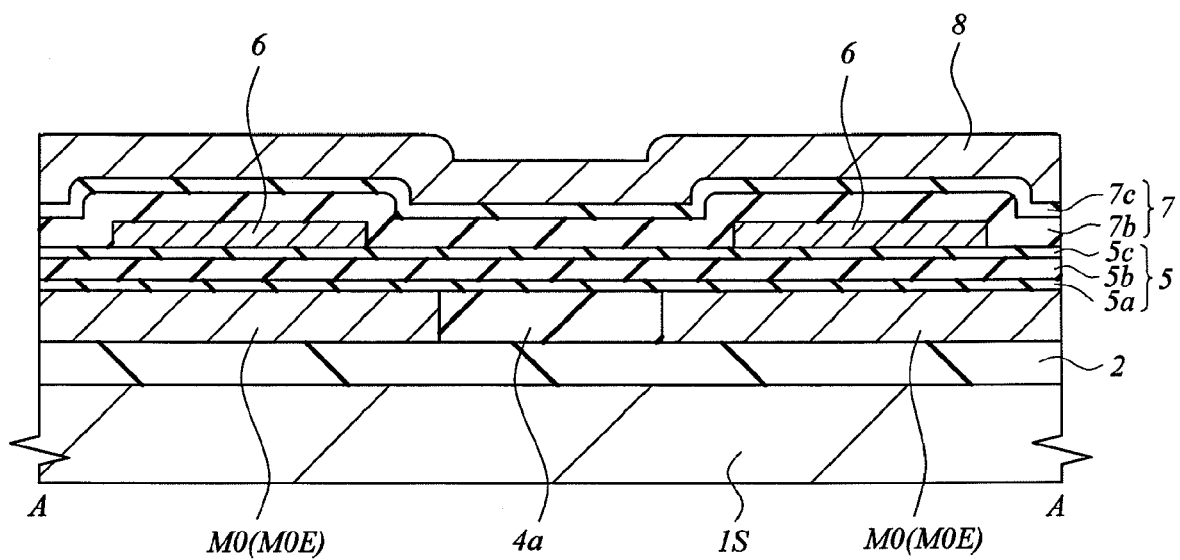
FIG. 27 is a cross-sectional view of the main portion of the semiconductor device during a manufacturing processing according to the second embodiment of the present invention.

FIG. 27 is a main portion cross-sectional view of the semiconductor device during a manufacturing processing according to the present embodiment and corresponds to FIG. 13 of the first embodiment.

In the present embodiment, after the configuration shown in FIG. 12 is obtained in the same way as that in the first embodiment, as shown in FIG. 27, the silicon nitride film 7b is formed (deposited) over the entire surface of the first main surface 1Sa of the semiconductor substrate 1S (that is, over the insulator film 5) using the plasma-enhanced CVD method or the like so as to cover the surface of the sacrificial film pattern 6 and the silicon oxide film 7c is formed (deposited) over the silicon nitride film 7b using the plasma-enhanced CVD method or the like. With this, the insulator film 7 composed of a stacked film of the silicon nitride film 7b and the silicon oxide film 7c is formed. A film thickness (deposition film thickness) of the silicon nitride film 7b can be approximately 265 nm, for example, and a film thickness (deposition film thickness) of the silicon oxide film 7c can be approximately 50 nm, for example.

Then, in the same way as the first embodiment, over the insulator film 7 composed of the stacked film of the silicon nitride film 7b and the silicon oxide film 7c, the conductive film 8 for formation of the upper electrode wiring M1 (upper electrode M1E) is formed. Since processings of formation of the conductive film 8 and thereafter are similar to those of the first embodiment, explanations thereof are omitted herein.

In this manner, as shown in FIGS. 25 and 26, the semiconductor device similar to that in the first embodiment except that the stacked film of the silicon nitride film 7b and the silicon oxide film 7c is used as the insulator film 7 can be obtained.

In the present embodiment, since the insulator films 5 and 7 include the silicon nitride films 5b and 7b positioned between the lower electrode M0E (lower electrode wiring M0) and the upper electrode M1E (upper electrode wiring M1), a conduction mechanisms of the insulator films 5 and 7 between the upper and lower electrodes becomes the Poole-Frenkel type. As described in the first embodiment, the breakdown voltage between the upper electrode M1E (upper electrode wiring M1) and the lower electrode M0E (lower electrode wiring M0) can be improved. Therefore, performance of the semiconductor device can be improved and the manufacturing yield can be increased.

Also, in the present embodiment, since the insulator film 7 is the stacked film of the silicon nitride film 7b and the silicon oxide film 7c, the breakdown voltage between the upper electrode M1E (upper electrode wiring M1) and the lower electrode M0E (lower electrode wiring M0) can be further improved and the manufacturing yield can be further increased in comparison with the case where the single layer of the silicon oxide film 7a is used as the insulator film 7 as described in the first embodiment. This is because the silicon nitride film 7b is introduced also to the insulator film 7 between the void VR and the upper electrode wiring M1, and therefore, the conduction mechanism of the insulator films 5 and 7 becomes more similar to the Poole-Frenkel type, and as a result, the influence of the electric-field enhancement at the edge of upper surface 121 of the lower electrode wiring M0 and the step over the lower surface of the upper electrode wiring M1 is further mitigated.

And, in the present embodiment, since the lowermost layer portion of the insulator film 5 is made of the silicon oxide film 5a and the uppermost layer portion of the insulator film 7 is made of the silicon oxide film 7c, a portion of the insulator film 5 contacting with the lower electrode M0E (lower electrode wiring M0) and a portion of the insulator film 7 contacting with the upper electrode M1E (upper electrode wiring M1) are the silicon oxide films 5a and 7c respectively, and therefore, the silicon nitride films 5b and 7b included in the insulator films 5 and 7 are prevented from contacting with both of the lower electrode M0E and the upper electrode M1E. With this, as described in the first embodiment, charge trapping to the silicon nitride films 5b and 7b included in the insulator films 5 and 7 can be suppressed or prevented, and fluctuation of the characteristic of the capacitive element (transducer) composed of the lower electrode M0E, the insulator film 5, the void VR, the insulator film 7 and the upper electrode M1E caused by charge trapping to the silicon nitride films 5b and 7b can be suppressed or prevented. Thus, the performance of the semiconductor device can be improved.

Therefore, both of improvement of the breakdown voltage between the electrodes of the ultrasonic transducer and suppression of the fluctuation of the transmitting/receiving gain caused by the charge trapping to the insulator films can be achieved.

And, in the present embodiment, the upper most layer portion of the insulator film 5 is composed of silicon oxide (here, the silicon oxide film 5c). The sacrificial film pattern 6 is formed by patterning the sacrificial film formed over the entire surface of the insulator film 5. However, in patterning of the sacrificial film, the uppermost layer portion of the underlying insulator film 5 may possibly be etched by over etching. But, if at least the uppermost layer portion of the insulator film 5 is composed of silicon oxide (in this case, a silicon nitride layer portion is provided to a region other than the uppermost layer portion of the insulator film 5 or the insulator film 7), even if silicon oxide of the uppermost layer portion of the insulator film 5 is more or less etched, the silicon nitride layer portion introduced to the insulator films 5 and 7 in order to improve the breakdown voltage can be prevented from being etched. Therefore, the silicon nitride layer portion (the silicon nitride films 5b, 5e, 7b and 7e in the present and other embodiments) having a film thickness as formed can be introduced to the insulator films 5 and 7, and the breakdown voltage between the upper electrode M1E (upper electrode wiring M1) and the lower electrode M0E (lower electrode wiring M0) can be improved more accurately. At least the uppermost layer portion of the insulator film 5 is composed of silicon oxide in the first and second embodiment described above and the third, fifth, and eighth embodiments described later, and the above-described effects can be achieved in these embodiments.

Third Embodiment

Figure 28:
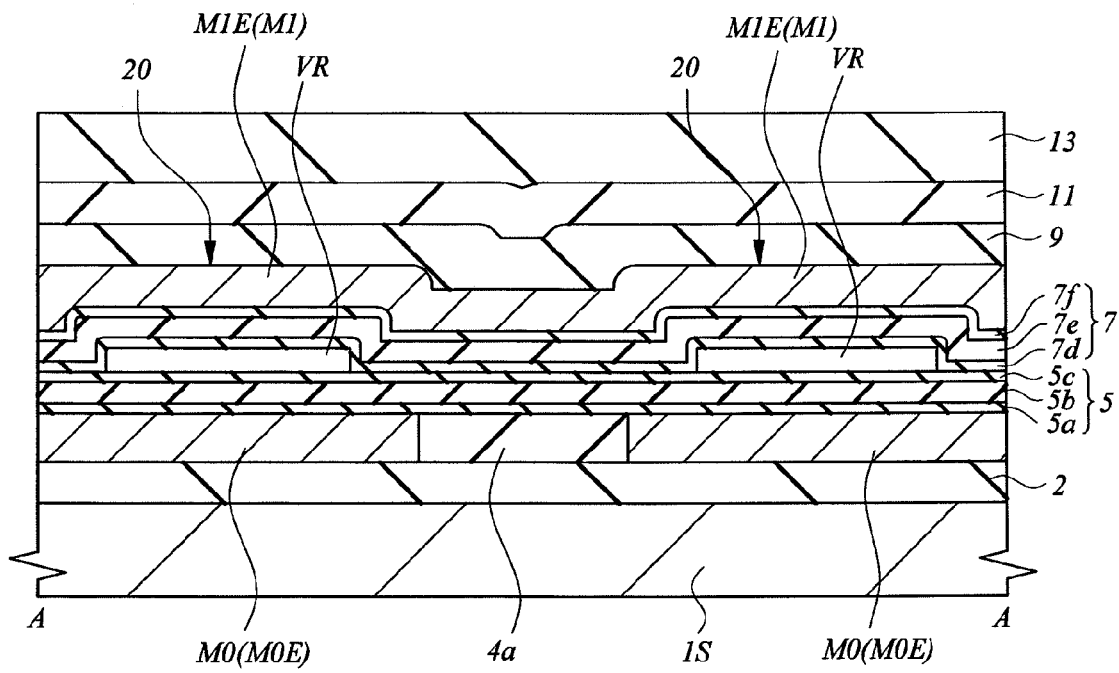
FIG. 28 is a cross-sectional view of a main portion of a semiconductor chip according to a third embodiment of the present invention.
Figure 29:
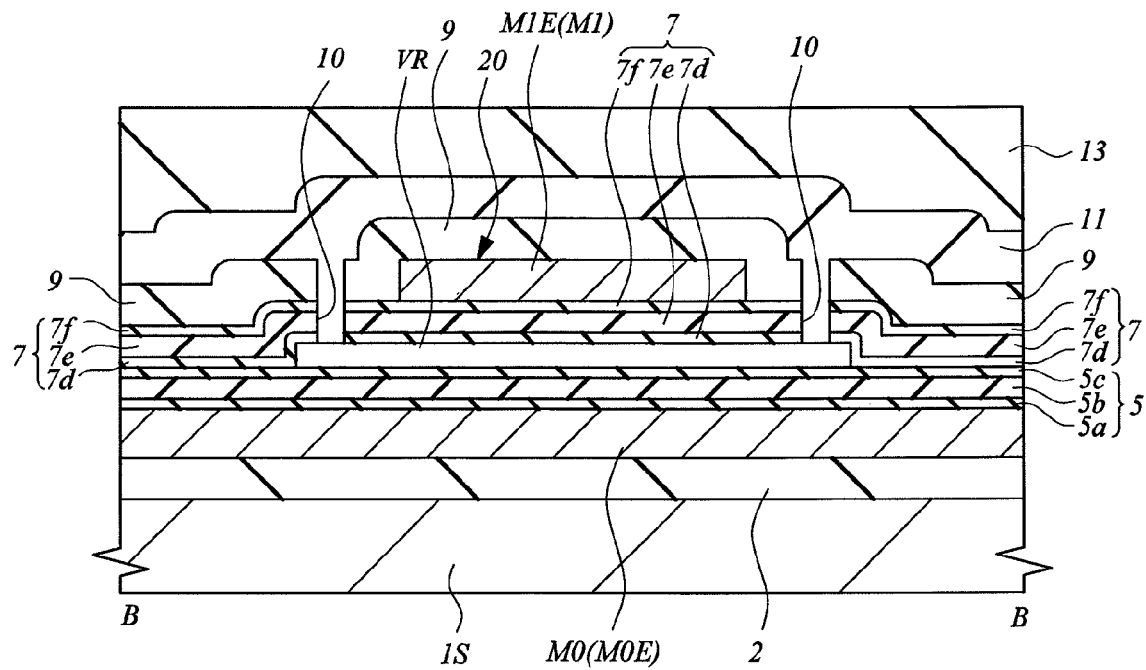
FIG. 29 is a cross-sectional view of the main portion of the semiconductor chip according to the third embodiment of the present invention.

FIGS. 28 and 29 are main portion cross-sectional views of a semiconductor device according to the present embodiment, and correspond to FIGS. 5 and 6 of the first embodiment, respectively.

In the first embodiment, as shown in FIGS. 5 and 6, the insulator film 5 is composed of a stacked film of the silicon oxide film 5a, the silicon nitride film 5b and the silicon oxide film 5c, and the insulator film 7 is composed of a single layer film (single layer) of the silicon oxide film 7a. On the other hand, in the present embodiment, as shown in FIGS. 28 and 29, although the insulator film 5 is composed of a stacked film of the silicon oxide film 5a, the silicon nitride film 5b and the silicon oxide film 5c in the same way as the first embodiment, the insulator film 7 is composed of, unlike the first embodiment, a stacked film of a silicon oxide film 7d, a silicon nitride film 7e and a silicon oxide film 7f sequentially stacked from below (a side of the insulator film 5). Other than that, a configuration of the semiconductor device according to the present embodiment is similar to that of the first embodiment, and therefore, an explanation thereof is omitted herein.

Figure 30:
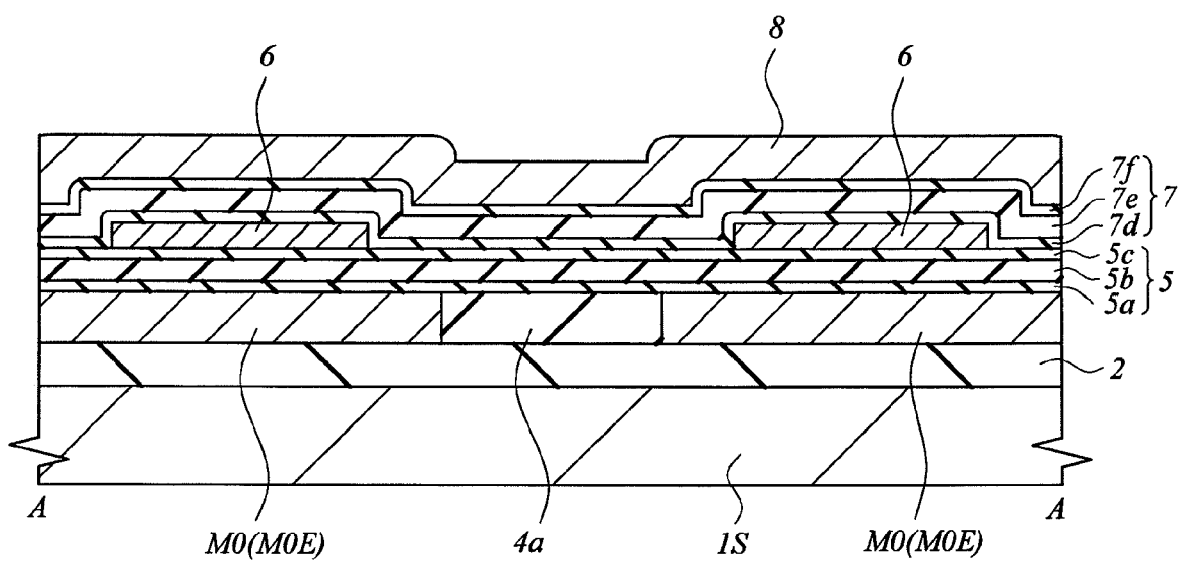
FIG. 30 is a cross-sectional view of the main portion of the semiconductor device during a manufacturing processing according to the third embodiment of the present invention.

FIG. 30 is a main portion cross-sectional view of the semiconductor device during a manufacturing processing according to the present embodiment, and corresponds to FIG. 13 of the first embodiment.

In the present embodiment, after the configuration shown in FIG. 12 is obtained in the same way as the first embodiment, a silicon oxide film 7d is formed (deposited) over the entire surface of the first main surface 1Sa of the semiconductor substrate 1S (that is, over the insulator film 5) using the plasma-enhanced CVD method or the like so as to cover the surface of the sacrificial film pattern 6 as shown in FIG. 30. Over the silicon oxide film 7d, the silicon nitride film 7e is formed (deposited) using the plasma-enhanced CVD method or the like and over the silicon nitride film 7e, the silicon oxide film 7f is formed (deposited) using the plasma-enhanced CVD method or the like. With this, the insulator film 7 composed of a stacked film of the silicon oxide film 7d, the silicon nitride film 7e and the silicon oxide film 7f is formed. A film thickness (deposition film thickness) of the silicon oxide film 7d can be approximately 50 nm, for example. A film thickness (deposition film thickness) of the silicon nitride film 7e can be approximately 175 nm, for example. A film thickness (deposition film thickness) of the silicon oxide film 7f can be approximately 50 nm, for example.

Then, in the same way as the first embodiment, the conductive film 8 for formation of the upper electrode wiring M1 (upper electrode M1E) is formed over the insulator film 7 composed of the stacked film of the silicon oxide film 7d, the silicon nitride film 7e and the silicon oxide film 7f. Since processings of formation of the conductive film 8 and thereafter are similar to those of the first embodiment, explanations thereof are omitted herein.

In this manner, as shown in FIGS. 28 and 29, the semiconductor device similar to that in the first embodiment except that the stacked film of the silicon oxide film 7d, the silicon nitride film 7e and the silicon oxide film 7f is used as the insulator film 7 can be obtained.

In the present embodiment, since the insulator films 5 and 7 include the silicon nitride films 5b and 7e positioned between the lower electrode M0E (lower electrode wiring M0) and the upper electrode M1E (upper electrode wiring M1), a conduction mechanism of the insulator films 5 and 7 between the upper and lower electrodes becomes the Poole-Frenkel type. As described in the first embodiment, the breakdown voltage between the upper electrode M1E (upper electrode wiring M1) and the lower electrode M0E (lower electrode wiring M0) can be improved. Therefore, performance of the semiconductor device can be improved and the manufacturing yield can be increased.

And, in the present embodiment, since the insulator film 7 is composed of the stacked film of the silicon oxide film 7d, the silicon nitride film 7e and the silicon oxide film 7f, the breakdown voltage between the upper electrode M1E (upper electrode wiring M1) and the lower electrode M0E (lower electrode wiring M0) can be further improved and the manufacturing yield can be further increased, in comparison with the case where the silicon oxide film 7a of a single layer is used as the insulator film 7 as described in the first embodiment and the case where the stacked film of the silicon nitride film 7b and the silicon oxide film 7c is used as the insulator film 7 as described in the second embodiment.

And, in the present embodiment, since the lowermost layer portion of the insulator film 5 is the silicon oxide film 5a and the uppermost layer portion of the insulator film 7 is the silicon oxide film 7f, a portion of the insulator film 5 contacting with the lower electrode M0E (lower electrode wiring M0) and a portion of the insulator film 7 contacting with the upper electrode M1E (upper electrode wiring M1) are the silicon oxide films 5a and 7f, respectively, thereby preventing the silicon nitride films 5b and 7e included in the insulator films 5 and 7 from contacting with both of the lower electrode M0E and the upper electrode M1E. With this, as described in the first embodiment, charge trapping to the silicon nitride films 5b and 7e included in the insulator films 5 and 7 can be suppressed or prevented, and the fluctuation of the characteristic of the capacitive element (transducer) composed of the lower electrode M0E, the insulator film 5, the void VR, the insulator film 7 and the upper electrode M1E caused by charge trapping to the silicon nitride films 5b and 7e can be prevented. Thus, the performance of the semiconductor device can be improved.

Therefore, both of improvement of the breakdown voltage between the electrodes of the ultrasonic transducer and suppression of the fluctuation of the transmitting/receiving gain caused by charge trapping of the insulator film can be achieved.

Furthermore, in the present embodiment, the sacrificial film pattern 6 for formation of the void VR is surrounded by a silicon oxide portion (here, silicon oxide films 5c and 7d), as shown in FIG. 30. When the sacrificial film pattern 6 is etched through the holes 10 to form the void VR as shown in FIG. 17, it is desirable to increase an etch rate ratio (the insulator film near the sacrificial film pattern 6 is made not to be etched as much as possible). In a case where the sacrificial film pattern 6 is formed of an amorphous silicon film, the etch rate ratio of the sacrificial film pattern 6 can be increased easily (the insulator film surrounding the sacrificial film pattern 6 is hard to be etched) in a case where a portion near the sacrificial film pattern 6 is formed of silicon oxide rather than a case where the portion is formed of silicon nitride, and a shape of the void VR is stabilized easily. Therefore, in the manufactured semiconductor device (semiconductor chip 1), if the void VR is surrounded by silicon oxide (silicon oxide portion), an amorphous silicon film or the like can be used as the sacrificial film pattern 6 for formation of the void VR and a range of selection of material of the sacrificial film pattern 6 for formation of the void VR can be widened. The void VR is surrounded by the silicon oxide (the silicon oxide portion) in the first and third embodiments described above and the eighth embodiment described later, and the above-described effects can be achieved in these embodiments.

Fourth Embodiment

Figure 31:
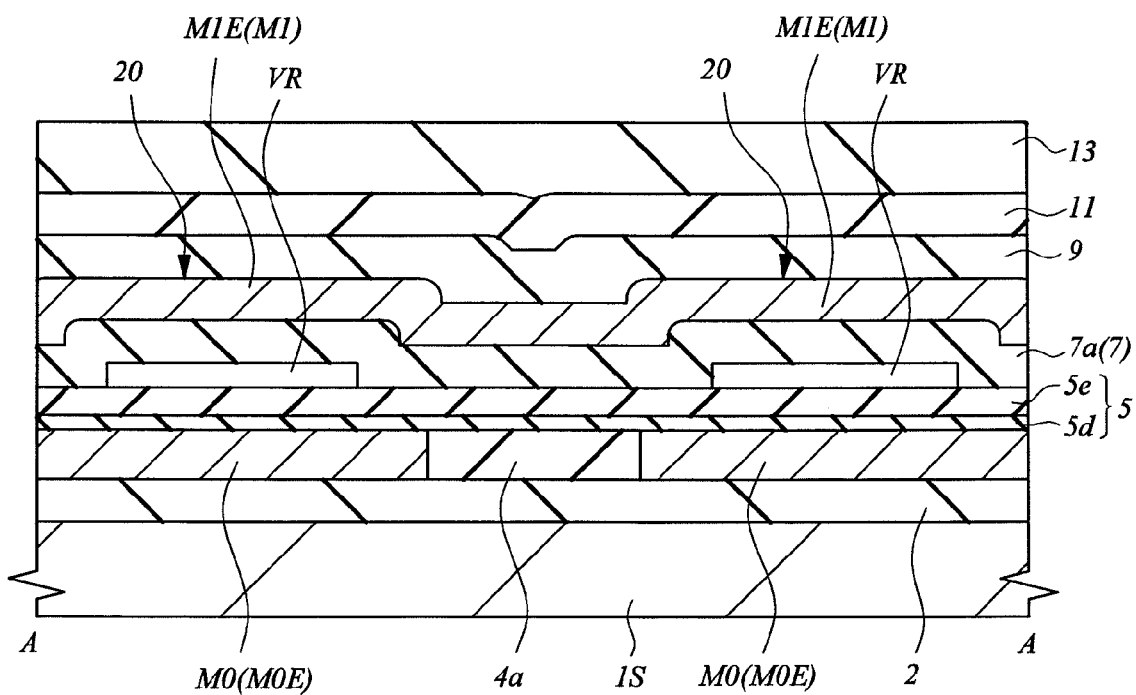
FIG. 31 is a cross-sectional view of a main portion of a semiconductor chip according to a fourth embodiment of the present invention.
Figure 32:
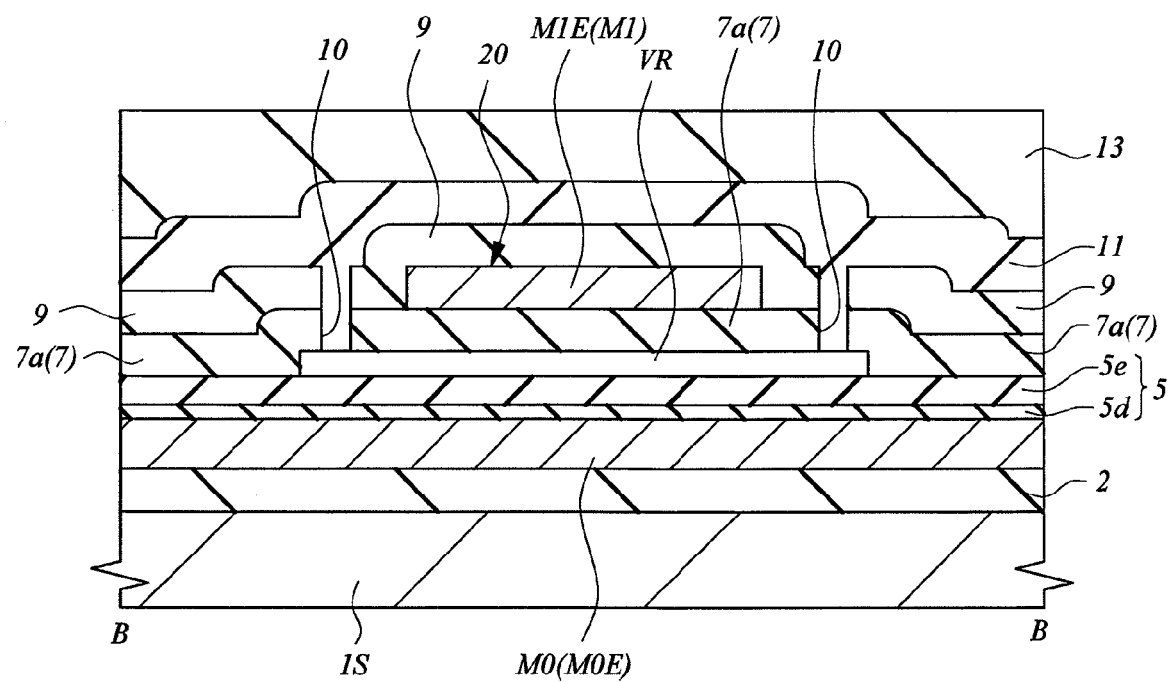
FIG. 32 is a cross-sectional view of the main portion of the semiconductor chip according to the fourth embodiment of the present invention.

FIGS. 31 and 32 are main portion cross-sectional views of a semiconductor device according to the present embodiment, and correspond to FIGS. 5 and 6 of the first embodiment, respectively.

In the first embodiment, as shown in FIGS. 5 and 6, the insulator film 5 is composed of a stacked film of the silicon oxide film 5a, the silicon nitride film 5b and the silicon oxide film 5c, and the insulator film 7 is composed of a single layer film (single layer) of the silicon oxide film 7a. On the other hand, in the present embodiment, as shown in FIGS. 31 and 32, although the insulator film 7 is composed of a single layer film (single layer) of the silicon oxide film 7a in the same manner as the first embodiment, the insulator film 5 is composed of, unlike the first embodiment, a stacked film of a silicon oxide film 5d and a silicon nitride film 5e sequentially stacked from below (a side of the lower electrode M0E). Other than that, a configuration of the semiconductor device according to the present embodiment is similar to that of the first embodiment, and therefore, an explanation thereof is omitted herein.

Figure 33:
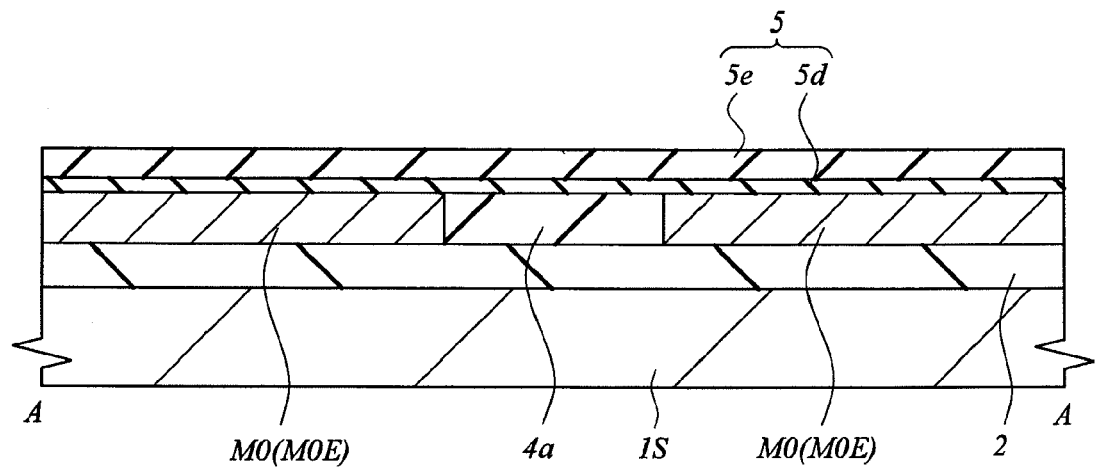
FIG. 33 is a cross-sectional view of the main portion of the semiconductor device during a manufacturing processing according to the fourth embodiment of the present invention.
Figure 34:
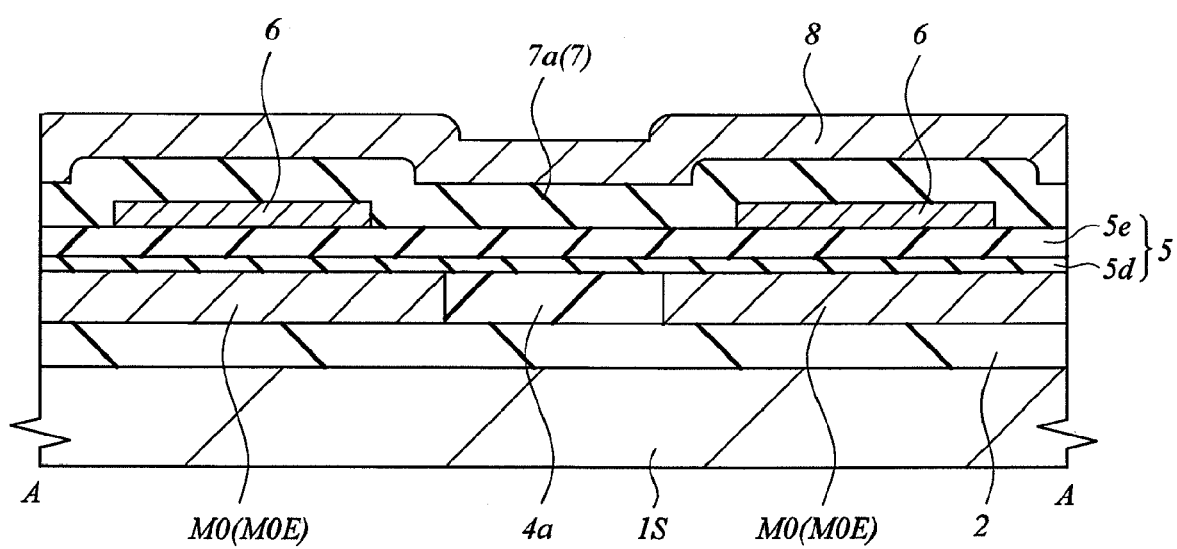
FIG. 34 is a cross-sectional view of the main portion of the semiconductor device during the manufacturing processing according to the fourth embodiment of the present invention.

FIGS. 33 and 34 are main portion cross-sectional views of the semiconductor device during a manufacturing processing according to the present embodiment, and correspond to FIGS. 11 and 13 of the first embodiment, respectively.

In the present embodiment, after the configuration shown in FIG. 10 is obtained in the same way as the first embodiment, the silicon oxide film 5d is formed (deposited) over the entire surface of the first main surface 1Sa of the semiconductor substrate 1S (that is, over an upper surfaces of the lower electrode wirings M0 and the insulator film 4a filling the lower electrode wirings M0) using the plasma-enhanced CVD method or the like, as shown in FIG. 33. The silicon nitride film 5e is formed (deposited) over the silicon oxide film 5d using the plasma-enhanced CVD method or the like. With this, the insulator film 5 composed of a stacked film of the silicon oxide film 5d and the silicon nitride film 5e is formed. A film thickness (deposition film thickness) of the silicon oxide film 5d can be approximately 50 nm, for example. The film thickness (deposition film thickness) of the silicon nitride film 5e can be approximately 265 nm, for example.

After formation of the insulator film 5, processings similar to those in the first embodiment are performed. That is, as shown in FIG. 34, over the insulator film 5 composed of the stacked film of the silicon oxide film 5d and the silicon nitride film 5e, the sacrificial film pattern 6 is formed in the same way as the first embodiment, and then the insulator film 7 composed of the silicon oxide film 7a is formed over the insulator film 5 so as to cover the sacrificial film pattern 6. Then, over the insulator film 7 composed of the silicon oxide film 7a, the conductive film 8 for formation of the upper electrode wiring M1 (upper electrode M1E) is formed. Since processings thereafter are similar to those in the first embodiment, explanations thereof are omitted herein.

In this manner, as shown in FIGS. 31 and 32, the semiconductor device similar to that of the first embodiment except that the stacked film of the silicon oxide film 5d and the silicon nitride film 5e is used as the insulator film 5 can be obtained.

In the present embodiment, since the insulator films 5 and 7 include the silicon nitride film 5e positioned between the lower electrode M0E (lower electrode wiring M0) and the upper electrode M1E (upper electrode wiring M1), the conduction mechanism of the insulator films 5 and 7 between the upper and lower electrodes becomes the Poole-Frenkel type. As described in the first embodiment, the breakdown voltage between the upper electrode M1E (upper electrode wiring M1) and the lower electrode M0E (lower electrode wiring M0) can be improved. Therefore, performance of the semiconductor device can be improved and the manufacturing yield can be increased.

And, in the present embodiment, since the lowermost layer portion of the insulator film 5 is composed of the silicon oxide film 5d and the insulator film 7 is composed of the silicon oxide film 7a, a portion of the insulator film 5 contacting with the lower electrode M0E (lower electrode wiring M0) and a portion of the insulator film 7 contacting with the upper electrode M1E (upper electrode wiring M1) are the silicon oxide films 5d and 7a, respectively, thereby preventing the silicon nitride film 5e included in the insulator films 5 and 7 from contacting with both of the lower electrode M0E and the upper electrode M1E. With this, as described in the first embodiment, charge trapping to the silicon nitride film 5e included in the insulator films 5 and 7 can be suppressed or prevented, and fluctuation of the characteristic of the capacitive element (transducer) composed of the lower electrode M0E, the insulator film 5, the void VR, the insulator film 7 and the upper electrode M1E caused by charge trapping to the silicon nitride film 5e can be suppressed or prevented. Thus, the performance of the semiconductor device can be improved.

Therefore, both of improvement of the breakdown voltage between the electrodes of the ultrasonic transducer and suppression of fluctuation of the transmitting/receiving gain caused by charge trapping of the insulator films can be achieved.

Fifth Embodiment

Figure 35:
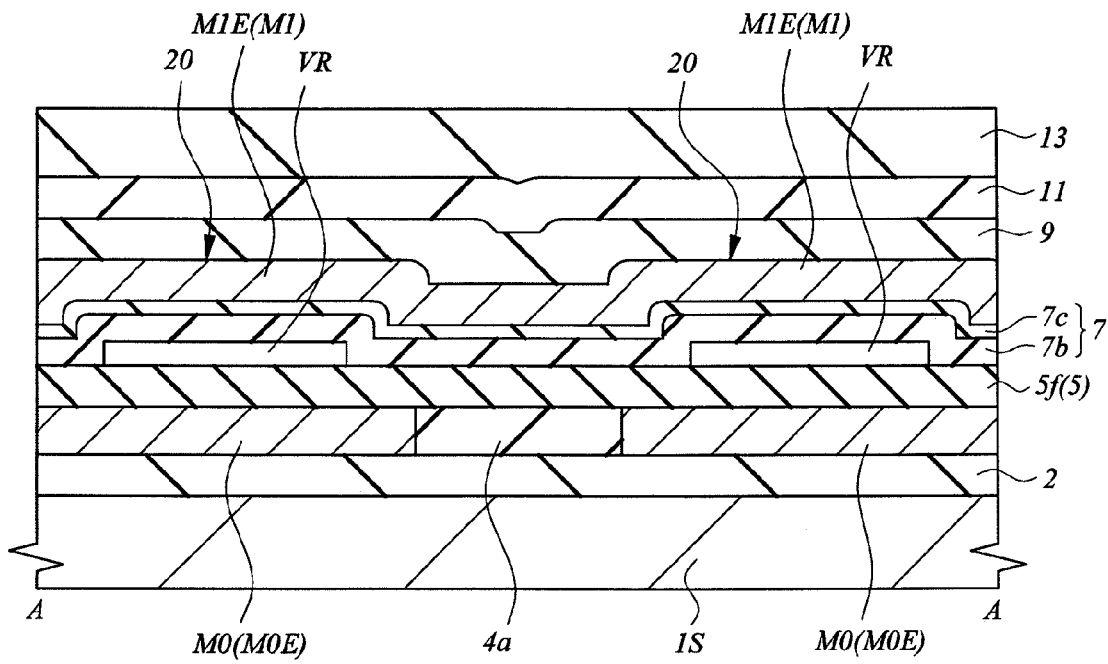
FIG. 35 is a cross-sectional view of a main portion of a semiconductor chip according to a fifth embodiment of the present invention.
Figure 36:
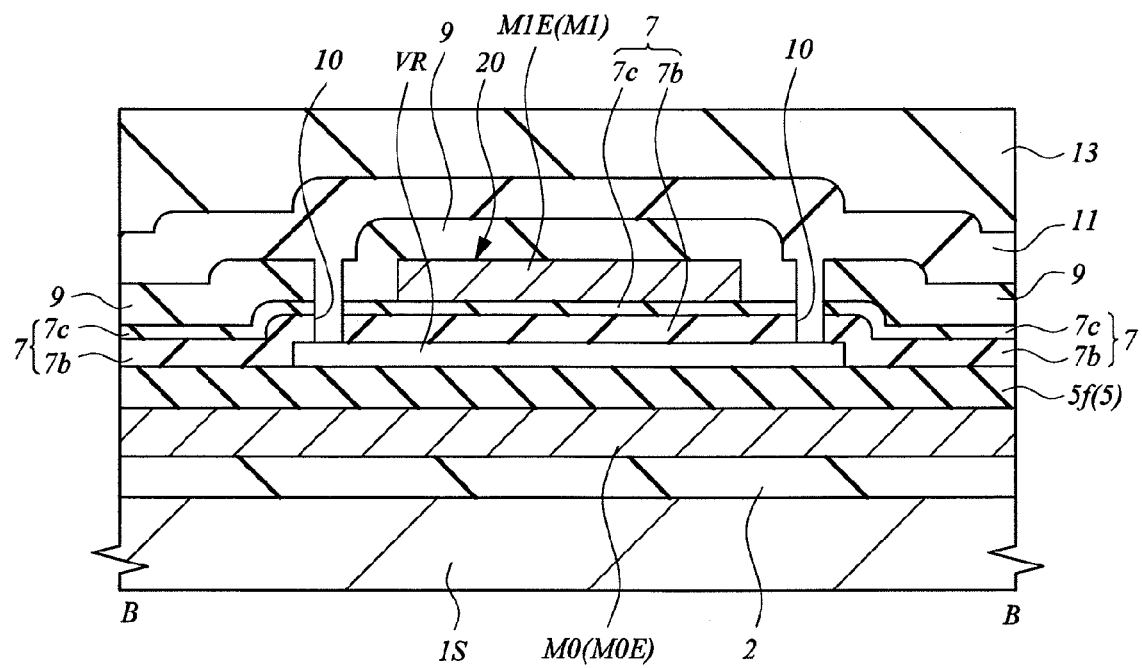
FIG. 36 is a cross-sectional view of the main portion of the semiconductor chip according to the fifth embodiment of the present invention.

FIGS. 35 and 36 are main portion cross-sectional views of a semiconductor device according to the present embodiment, and correspond to FIGS. 5 and 6 of the first embodiment, respectively.

In the first embodiment, as shown in FIGS. 5 and 6, the insulator film 5 is composed of a stacked film of the silicon oxide film 5a, the silicon nitride film 5b and the silicon oxide film 5c, and the insulator film 7 is composed of a single layer film (single layer) of the silicon oxide film 7a. On the other hand, in the present embodiment, as shown in FIGS. 35 and 36, the insulator film 5 is composed of, unlike the first embodiment, a single layer film (single layer) of the silicon oxide film 5f, and the insulator film 7 is composed of, unlike the first embodiment (but in the same way as the second embodiment), a stacked film of the silicon nitride film 7b and the silicon oxide film 7c sequentially stacked from below (a side of the insulator film 5). Other than that, a configuration of the semiconductor device according to the present embodiment is similar to that of the first embodiment, and therefore, an explanation thereof is omitted herein.

Figure 37:
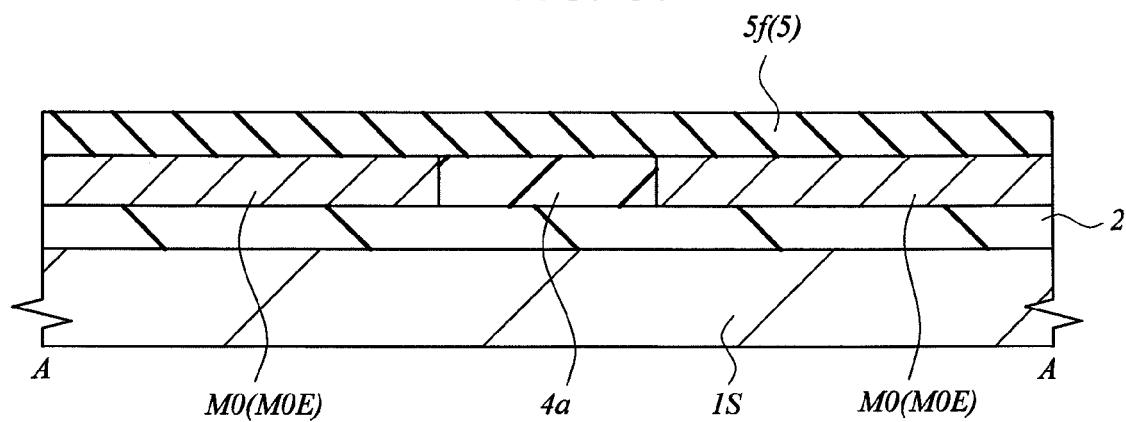
FIG. 37 is a cross-sectional view of the main portion of the semiconductor device during a manufacturing processing according to the fifth embodiment of the present invention.
Figure 38:
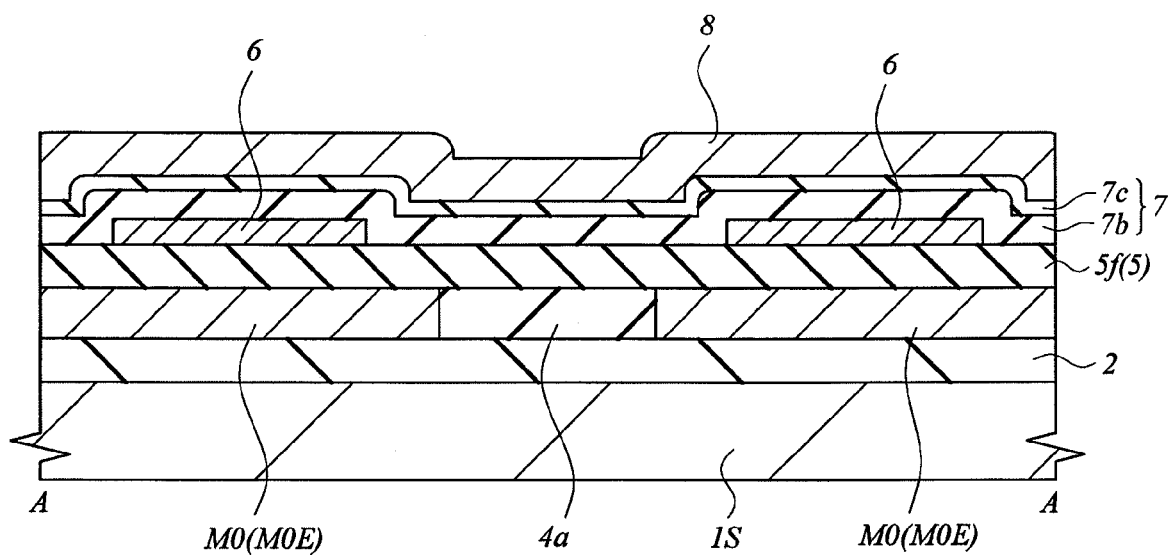
FIG. 38 is a cross-sectional view of the main portion of the semiconductor device during the manufacturing processing according to the fifth embodiment of the present invention.

FIGS. 37 and 38 are main portion cross-sectional views of the semiconductor device during a manufacturing processing according to the present embodiment, and correspond to FIGS. 11 and 13 of the first embodiment, respectively.

In the present embodiment, after a configuration shown in FIG. 10 is obtained in the same way as the first embodiment, as shown in FIG. 37, the silicon oxide film 5f is formed (deposited) using the plasma-enhanced CVD method or the like over the entire surface of the first main surface 1Sa of the semiconductor substrate 1S (that is, over the upper surfaces of the lower electrode wirings M0 and the insulator film 4a filling the lower electrode wirings M0). With this, the insulator film 5 composed of a single layer film (single layer) of the silicon oxide film 5f is formed. A film thickness (deposition film thickness) of the silicon oxide film 5f can be approximately 200 nm, for example.

After formation of the insulator film 5, processings similar to those in the first embodiment are performed until a processing immediately before formation of the insulator film 7. That is, as shown in FIG. 38, the sacrificial film pattern 6 is formed over the insulator film 5 composed of the silicon oxide film 5f, in the same way as the first embodiment.

Then, in the present embodiment, in the same way as the second embodiment, the silicon nitride film 7b is formed (deposited) over the entire surface of the first main surface 1Sa of the semiconductor substrate 1S (that is, over the insulator film 5) using the plasma-enhanced CVD method or the like so as to cover a surface of the sacrificial film pattern 6 and the silicon oxide film 7c is formed (deposited) over the silicon nitride film 7b using the plasma-enhanced CVD method or the like. With this, the insulator film 7 composed of a stacked film of the silicon nitride film 7b and the silicon oxide film 7c is formed. A film thickness (deposition film thickness) of the silicon nitride film 7b can be approximately 265 nm, for example, and a film thickness (deposition film thickness) of the silicon oxide film 7c can be approximately 50 nm, for example.

Then, in the same way as the first embodiment, the conductive film 8 for formation of the upper electrode wiring M1 (upper electrode M1E) is formed over the insulator film 7 composed of the stacked film of the silicon nitride film 7b and the silicon oxide film 7c. Since processings of formation of the conductive film 8 and thereafter are similar to those in the first embodiment, explanations thereof are omitted herein.

As described above, as shown in FIGS. 35 and 36, the semiconductor device similar to that of the first embodiment except that the single layer film (single layer) of the silicon oxide film 5f is used as the insulator film 5 and the stacked film of the silicon nitride film 7b and the silicon oxide film 7c is used as the insulator film 7 can be obtained.

In the present embodiment, since the insulator films 5 and 7 include the silicon nitride film 7b positioned between the lower electrode M0E (lower electrode wiring M0) and the upper electrode M1E (upper electrode wiring M1), a conduction mechanism of the insulator films 5 and 7 between the upper and lower electrodes becomes the Poole-Frenkel type. As described in the first embodiment, the breakdown voltage between the upper electrode M1E (upper electrode wiring M1) and the lower electrode M0E (lower electrode wiring M0) can be improved. Therefore, performance of the semiconductor device can be improved and the manufacturing yield can be increased.

And, in the present embodiment, since the insulator film 5 is the silicon oxide film 5f and the uppermost layer portion of the insulator film 7 is the silicon oxide film 7c, a portion of the insulator film 5 contacting with the lower electrode M0E (lower electrode wiring M0) and a portion of the insulator film 7 contacting with the upper electrode M1E (upper electrode wiring M1) are the silicon oxide films 5f and 7c, thereby preventing the silicon nitride film 7b included in the insulator films 5 and 7 from contacting with both of the lower electrode M0E and the upper electrode M1E. With this, as described in the first embodiment, charge trapping to the silicon nitride film 7b included in the insulator films 5 and 7 can be suppressed or prevented, and therefore fluctuation of the characteristic of the capacitive element (transducer) composed of the lower electrode M0E, the insulator film 5, the void VR, the insulator film 7 and the upper electrode M1E caused by charge trapping to the silicon nitride film 7b can be suppressed or prevented. Therefore, the performance of the semiconductor device can be improved.

Accordingly, both of improvement of the breakdown voltage between the electrodes of the ultrasonic transducer and suppression of fluctuation of the transmitting/receiving gain caused by charge trapping of the insulator films can be achieved.

Sixth Embodiment

Figure 39:
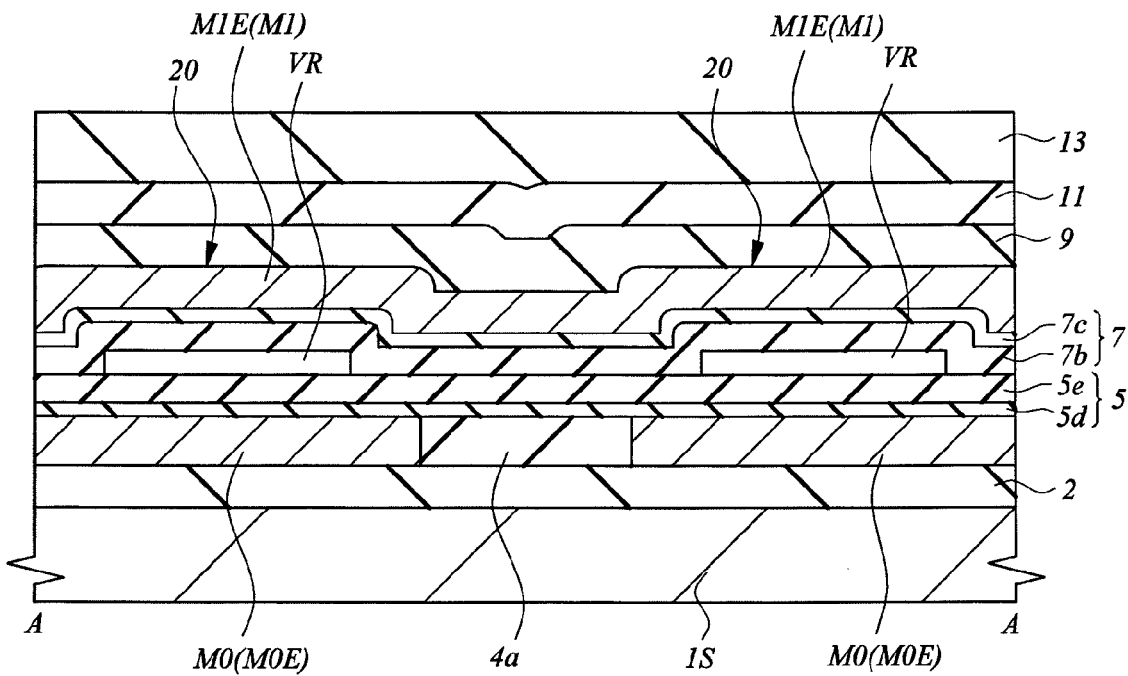
FIG. 39 is a cross-sectional view of a main portion of a semiconductor chip according to a sixth embodiment of the present invention.
Figure 40:
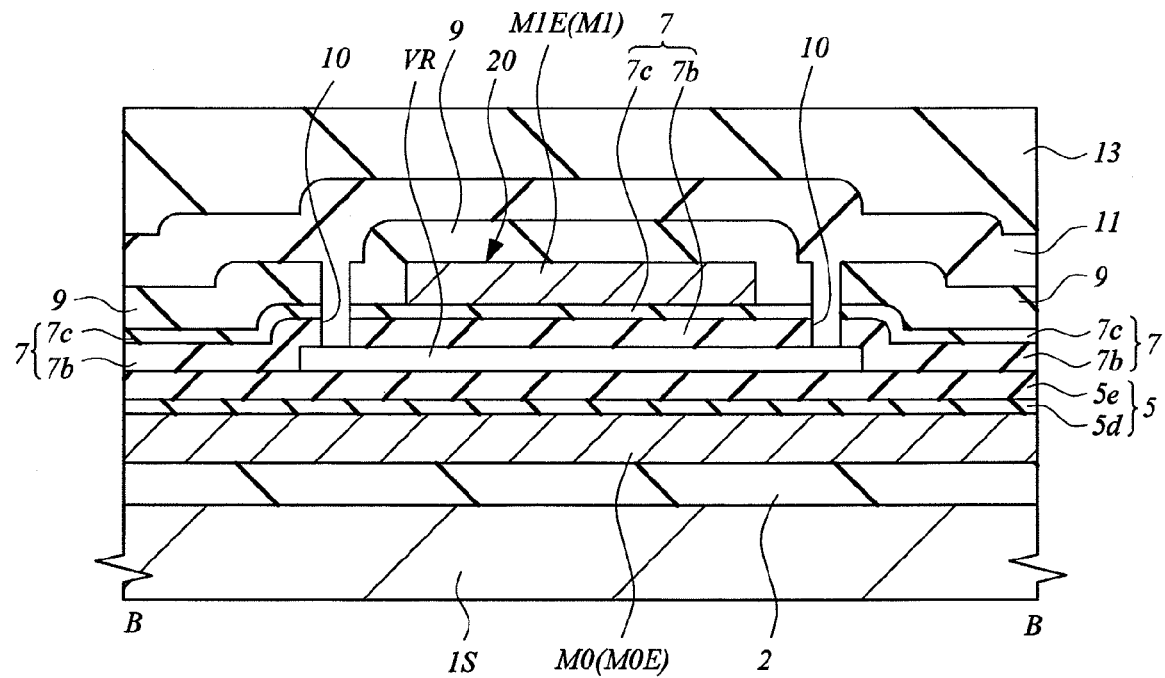
FIG. 40 is a cross-sectional view of the main portion of the semiconductor chip according to the sixth embodiment of the present invention.

FIGS. 39 and 40 are main portion cross-sectional views of a semiconductor device according to the present embodiment and correspond to FIGS. 5 and 6 of the first embodiment, respectively.

In the first embodiment, as shown in FIGS. 5 and 6, the insulator film 5 is composed of a stacked film of the silicon oxide film 5a, the silicon nitride film 5b and the silicon oxide film 5c, and the insulator film 7 is composed of a single layer film (single layer) of the silicon oxide film 7a. On the other hand, in the present embodiment, as shown in FIGS. 39 and 40, the insulator film 5 is composed of, unlike the first embodiment (but in the same way as the fourth embodiment), a stacked film of the silicon oxide film 5d and the silicon nitride film 5e sequentially stacked from below (a side of the lower electrode M0E), and the insulator film 7 is composed of, unlike the first embodiment (but in the same way as the second and fifth embodiments), a stacked layer of the silicon nitride film 7b and the silicon oxide film 7c sequentially stacked from below (a side of the insulator film 5). Other than that, a configuration of the semiconductor device according to the present embodiment is similar to that of the first embodiment, and therefore, an explanation thereof is omitted herein.

Figure 41:
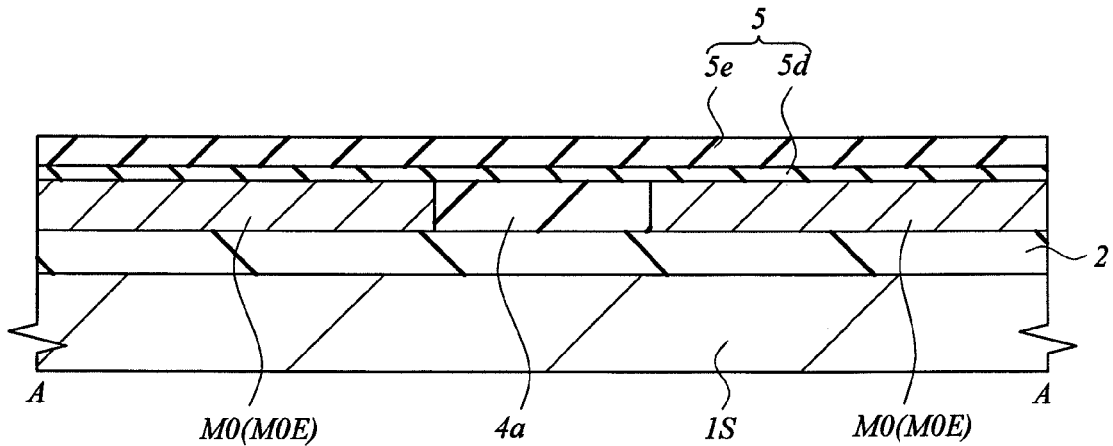
FIG. 41 is a cross-sectional view of the main portion of the semiconductor device during a manufacturing processing according to the sixth embodiment of the present invention.
Figure 42:
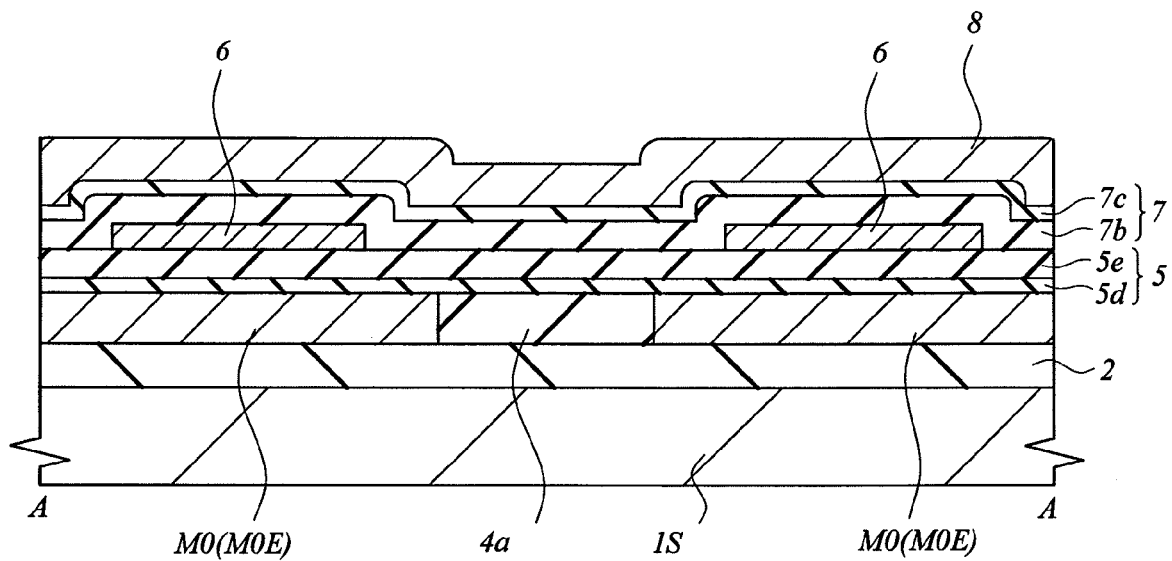
FIG. 42 is a cross-sectional view of the main portion of the semiconductor device during the manufacturing processing according to the sixth embodiment of the present invention.

FIGS. 41 and 42 are main portion cross-sectional views of the semiconductor device during a manufacturing processing according to the present embodiment, and correspond to FIGS. 11 and 13 of the first embodiment, respectively.

In the present embodiment, after the configuration shown in FIG. 10 is obtained in the same way as the first embodiment, the silicon oxide film 5d is formed (deposited) over the entire surface of the first main surface 1Sa of the semiconductor substrate 1S (that is, over the upper surfaces of the lower electrode wirings M0 and the insulator film 4a filling the lower electrode wirings M0) using the plasma-enhanced CVD method or the like and the silicon nitride film 5e is formed (deposited) over the silicon oxide film 5d using the plasma-enhanced CVD method or the like in the same way as the fourth embodiment, as shown in FIG. 41. With this, the insulator film 5 composed of a stacked film of the silicon oxide film 5d and the silicon nitride film 5e is formed. A film thickness (deposition film thickness) of the silicon oxide film 5d can be approximately 50 nm, for example, and a film thickness (deposition film thickness) of the silicon nitride film 5e can be approximately 265 nm, for example.

After formation of the insulator film 5, processings similar to those in the first embodiment are performed until a processing immediately before formation of the insulator film 7. That is, as shown in FIG. 38, the sacrificial film pattern 6 is formed over the insulator film 5 composed of a stacked film of the silicon oxide film 5d and the silicon nitride film 5e, in the same way as the first embodiment.

Then, in the present embodiment, in the same way as the second and fifth embodiments, the silicon nitride film 7b is formed (deposited) over the entire surface of the first main surface 1Sa of the semiconductor substrate 1S (that is, over the insulator film 5) using the plasma-enhanced CVD method or the like so as to cover a surface of the sacrificial film pattern 6 and the silicon oxide film 7c is formed (deposited) over the silicon nitride film 7b using the plasma-enhanced CVD method or the like. With this, the insulator film 7 composed of a stacked film of the silicon nitride film 7b and the silicon oxide film 7c is formed. A film thickness (deposition film thickness) of the silicon nitride film 7b can be approximately 265 nm, for example, and a film thickness (deposition film thickness) of the silicon oxide film 7c can be approximately 50 nm, for example.

Then, in the same way as the first embodiment, the conductive film 8 for formation of the upper electrode wiring M1 (upper electrode M1E) is formed over the insulator film 7 composed of the stacked film of the silicon nitride film 7b and the silicon oxide film 7c. Since processings of formation of the conductive film 8 and thereafter are similar to those in the first embodiment, explanations thereof are omitted herein.

As described above, as shown in FIGS. 39 and 40, the semiconductor device similar to that of the first embodiment except that the stacked film of the silicon oxide film 5d and the silicon nitride film 5e is used as the insulator film 5 and the stacked film of the silicon nitride film 7b and the silicon oxide film 7c is used as the insulator film 7 can be obtained.

In the present embodiment, since the insulator films 5 and 7 include the silicon nitride films 5e and 7b positioned between the lower electrode M0E (lower electrode wiring M0) and the upper electrode M1E (upper electrode wiring M1), a conduction mechanism of the insulator films 5 and 7 between the upper and lower electrodes becomes the Poole-Frenkel type. As described in the first embodiment, the breakdown voltage between the upper electrode M1E (upper electrode wiring M1) and the lower electrode M0E (lower electrode wiring M0) can be improved. Therefore, performance of the semiconductor device can be improved and the manufacturing yield can be increased.

And, in the present embodiment, since the insulator films 5 and 7 include the silicon nitride films 5e and 7b of two layers, the conduction mechanism of the insulator films 5 and 7 becomes closer to the Poole-Frenkel type in comparison with a case where one layer of the silicon nitride film is used, the breakdown voltage between the upper electrode M1E (upper electrode wiring M1) and the lower electrode M0E (lower electrode wiring M0) can be further improved and the manufacturing yield of the semiconductor device can be further increased.

Furthermore, in the present embodiment, since the silicon oxide film 5d is used as the lowermost layer portion of the insulator film 5 and the silicon oxide film 7c is used as the uppermost layer portion of the insulator film 7, a portion of the insulator film 5 contacting with the lower electrode M0E (lower electrode wiring M0) and a portion of the insulator film 7 contacting with the upper electrode M1E (upper electrode wiring M1) are the silicon oxide films 5d and 7c, thereby preventing the silicon nitride films 5e and 7b included in the insulator films 5 and 7 from contacting with both of the lower electrode M0E and the upper electrode M1E. With this, as described in the first embodiment, charge trapping to the silicon nitride films 5e and 7b included in the insulator films 5 and 7 can be suppressed or prevented, and fluctuation of the characteristic of the capacitive element (transducer) composed of the lower electrode M0E, the insulator film 5, the void VR, the insulator film 7 and the upper electrode M1E caused by charge trapping to the silicon nitride films 5e and 7b can be suppressed or prevented. Thus, the performance of the semiconductor device can be improved.

Accordingly, both of improvement of the breakdown voltage between the electrodes of the ultrasonic transducer and suppression of fluctuation of the transmitting/receiving gain caused by charge trapping of the insulator film can be achieved.

Seventh Embodiment

Figure 43:
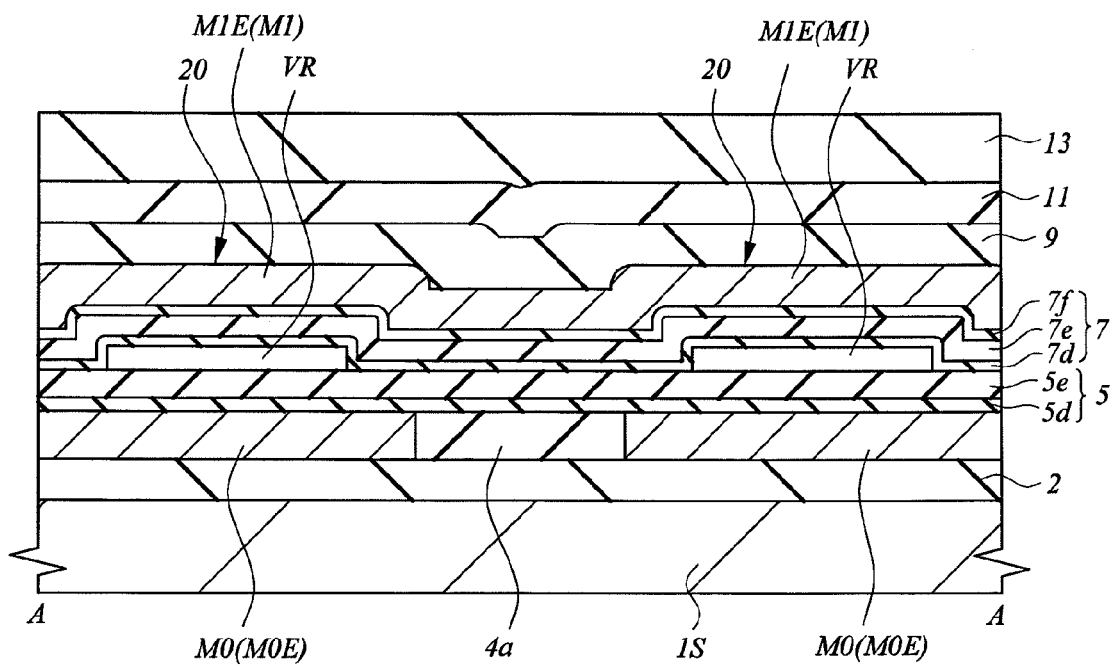
FIG. 43 is a cross-sectional view of a main portion of a semiconductor chip according to a seventh embodiment of the present invention.
Figure 44:
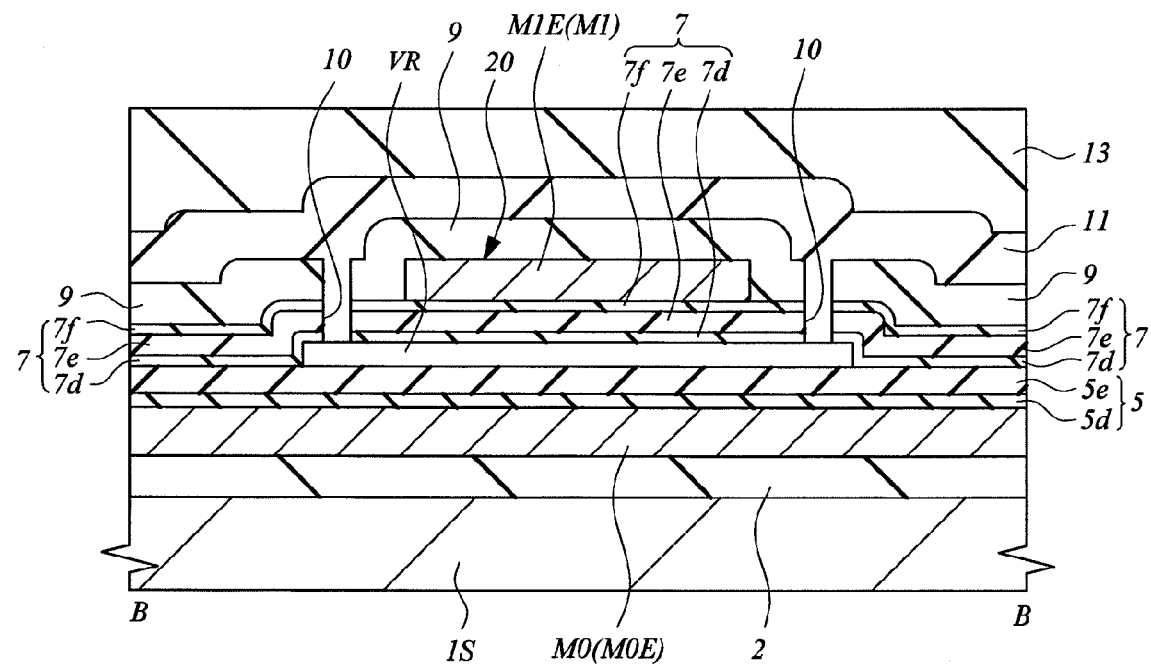
FIG. 44 is a cross-sectional view of the main portion of the semiconductor chip according to the seventh embodiment of the present invention.

FIGS. 43 and 44 are main portion cross-sectional views of a semiconductor device according to the present embodiment and correspond to FIGS. 5 and 6 of the first embodiment, respectively.

In the first embodiment, as shown in FIGS. 5 and 6, the insulator film 5 is composed of a stacked film of the silicon oxide film 5a, the silicon nitride film 5b and the silicon oxide film 5c, and the insulator film 7 is composed of a single layer film (single layer) of the silicon oxide film 7a. On the other hand, in the present embodiment, as shown in FIGS. 43 and 44, the insulator film 5 is composed of, unlike the first embodiment (but in the same way as the fourth and sixth embodiments), a stacked film of the silicon oxide film 5d and the silicon nitride film 5e sequentially stacked from below (a side of the lower electrode M0E), and the insulator film 7 is composed of, unlike the first embodiment (but in the same way as the third embodiment), a stacked film of the silicon oxide film 7d, the silicon nitride film 7e and the silicon oxide film 7f sequentially stacked from below (a side of the insulator film 5). Other than that, a configuration of the semiconductor device according to the present embodiment is similar to that of the first embodiment, and therefore, an explanation thereof is omitted herein.

Figure 45:
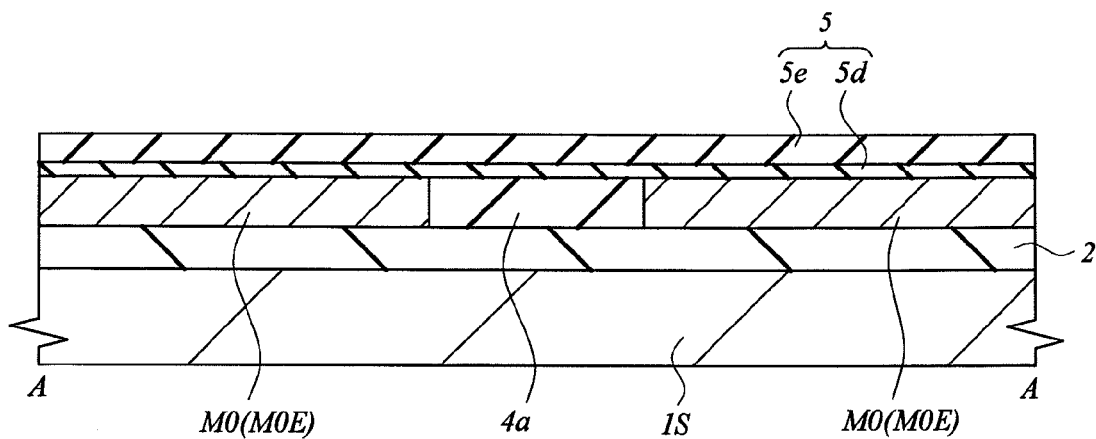
FIG. 45 is a cross-sectional view of the main portion of the semiconductor device during a manufacturing processing according to the seventh embodiment of the present invention.
Figure 46:
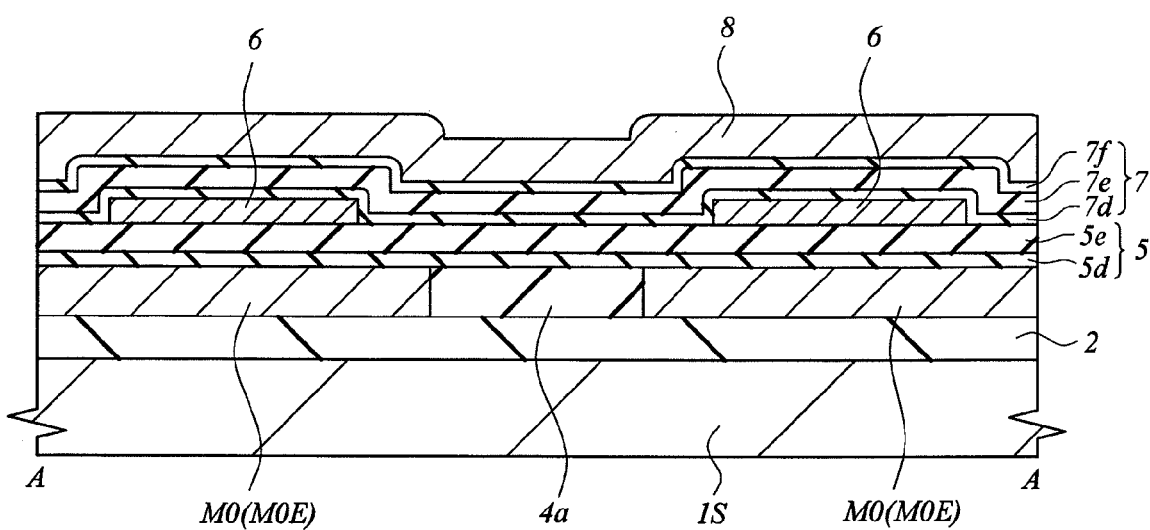
FIG. 46 is a cross-sectional view of the main portion of the semiconductor device during the manufacturing processing according to the seventh embodiment of the present invention.

FIGS. 45 and 46 are main portion cross-sectional views of the semiconductor device during a manufacturing processing according to the present embodiment, and correspond to FIGS. 11 and 13 of the first embodiment, respectively.

In the present embodiment, after the configuration shown in FIG. 10 is obtained in the same way as the first embodiment, the silicon oxide film 5d is formed (deposited) over the entire surface of the first main surface 1Sa of the semiconductor substrate 1S (that is, over the upper surfaces of the lower electrode wirings M0 and the insulator film 4a filling the lower electrode wirings M0) using the plasma-enhanced CVD method or the like and the silicon nitride film 5e is formed (deposited) over the silicon oxide film 5d using the plasma-enhanced CVD method or the like in the same way as the fourth and sixth embodiments, as shown in FIG. 45. With this, the insulator film 5 composed of a stacked film of the silicon oxide film 5d and the silicon nitride film 5e is formed. A film thickness (deposition film thickness) of the silicon oxide film 5d can be approximately 50 nm, for example, and a film thickness (deposition film thickness) of the silicon nitride film 5e can be approximately 265 nm, for example.

After formation of the insulator film 5, processings similar to those in the first embodiment are performed until a processing immediately before formation of the insulator film 7. That is, as shown in FIG. 46, the sacrificial film pattern 6 is formed over the insulator film 5 composed of a stacked film of the silicon oxide film 5d and the silicon nitride film 5e, in the same way as the first embodiment.

Then, in the present embodiment, in the same way as the third embodiment, the silicon oxide film 7d is formed (deposited) over the entire surface of the first main surface 1Sa of the semiconductor substrate 1S (that is, over the insulator film 5) using the plasma-enhanced CVD method or the like so as to cover a surface of the sacrificial film pattern 6 and the silicon nitride film 7e is formed (deposited) over the silicon oxide film 7d using the plasma-enhanced CVD method or the like. With this, the insulator film 7 composed of a stacked film of the silicon oxide film 7d, the silicon nitride film 7e and the silicon oxide film 7f is formed. A film thickness (deposition film thickness) of the silicon oxide film 7d can be approximately 50 nm, for example, a film thickness (deposition film thickness) of the nitride oxide film 7e can be approximately 175 nm, for example and a film thickness (deposition film thickness) of the silicon oxide film 7f can be approximately 50 nm, for example.

Then, in the same way as the first embodiment, the conductive film 8 for formation of the upper electrode wiring M1 (upper electrode M1E) is formed over the insulator film 7 composed of a stacked film of the silicon oxide film 7d, the silicon nitride film 7e and the silicon oxide film 7f. Since processings of formation of the conductive film 8 and thereafter are similar to those in the first embodiment, explanations thereof are omitted herein.

As described above, as shown in FIGS. 43 and 44, the semiconductor device similar to that of the first embodiment except that the stacked film of the silicon oxide film 5d and the silicon nitride film 5e is used as the insulator film 5 and the stacked film of the silicon oxide film 7d, the silicon nitride film 7e and the silicon oxide film 7f is used as the insulator film 7 can be obtained.

In the present embodiment, since the insulator films 5 and 7 include the silicon nitride films 5e and 7e positioned between the lower electrode M0E (lower electrode wiring M0) and the upper electrode M1E (upper electrode wiring M1), a conduction mechanism of the insulator films 5 and 7 between the upper and lower electrodes becomes the Poole-Frenkel type. As described in the first embodiment, the breakdown voltage between the upper electrode M1E (upper electrode wiring M1) and the lower electrode M0E (lower electrode wiring M0) can be improved. Therefore, performance of the semiconductor device can be improved and the manufacturing yield can be increased.

And, in the present embodiment, since the insulator films 5 and 7 include two layers of the silicon nitride films 5e and 7e, the conduction mechanism of the insulator films 5 and 7 becomes closer to the Poole-Frenkel type in comparison with a case where one layer of the silicon nitride film is used. Furthermore, the silicon oxide film 7d is interposed between the silicon nitride films 5e and 7e, and therefore, the breakdown voltage between the upper electrode M1E (upper electrode wiring M1) and the lower electrode M0E (lower electrode wiring M0) can be further improved and the manufacturing yield of the semiconductor device can be further increased.

Furthermore, in the present embodiment, since the silicon oxide film 5d is used as the lowermost layer portion of the insulator film 5 and the silicon oxide film 7f is used as the uppermost layer portion of the insulator film 7, a portion of the insulator film 5 contacting with the lower electrode M0E (lower electrode wiring M0) and a portion of the insulator film 7 contacting with the upper electrode M1E (upper electrode wiring M1) are the silicon oxide films 5d and 7f, thereby preventing the silicon nitride films 5e and 7e included in the insulator films 5 and 7 from contacting with both of the lower electrode M0E and the upper electrode M1E. With this, as described in the first embodiment, charge trapping to the silicon nitride films 5e and 7e included in the insulator films 5 and 7 can be suppressed or prevented, and fluctuation of the characteristic of the capacitive element (transducer) composed of the lower electrode M0E, the insulator film 5, the void VR, the insulator film 7 and the upper electrode M1E caused by charge trapping to the silicon nitride films 5e and 7e can be suppressed or prevented. Thus, the performance of the semiconductor device can be improved.

Accordingly, both of improvement of the breakdown voltage between the electrodes of the ultrasonic transducer and suppression of fluctuation of the transmitting/receiving gain caused by charge trapping of the insulator film can be achieved.

Eighth Embodiment

Figure 47:
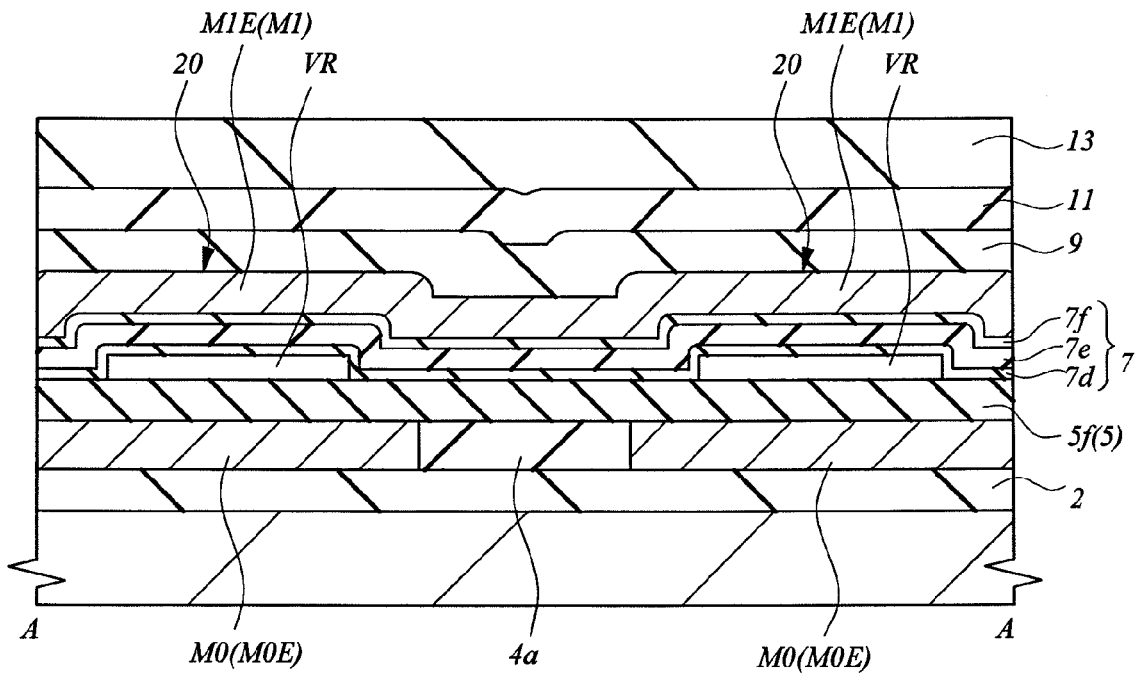
FIG. 47 is a cross-sectional view of a main portion of a semiconductor chip according to an eighth embodiment of the present invention.
Figure 48:
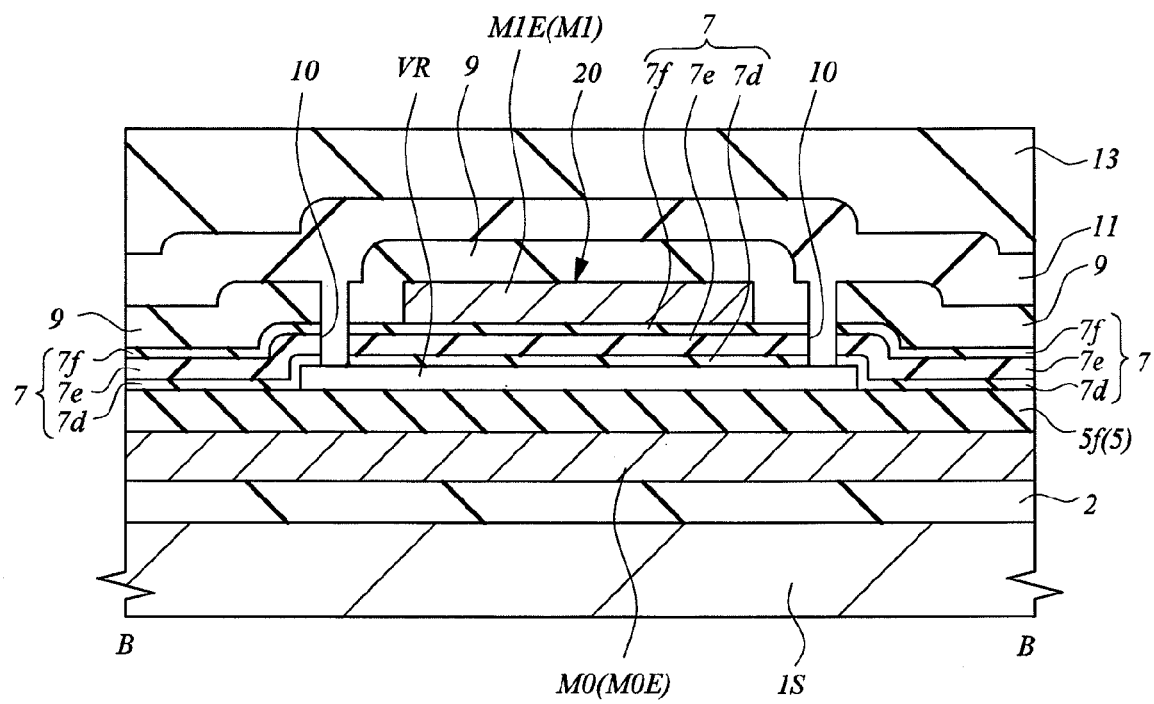
FIG. 48 is a cross-sectional view of the main portion of the semiconductor chip according to the eighth embodiment of the present invention.

FIGS. 47 and 48 are main portion cross-sectional views of a semiconductor device according to the present embodiment and correspond to FIGS. 5 and 6 of the first embodiment, respectively.

In the first embodiment, as shown in FIGS. 5 and 6, the insulator film 5 is composed of a stacked film of the silicon oxide film 5a, the silicon nitride film 5b and the silicon oxide film 5c, and the insulator film 7 is composed of a single layer film (single layer) of the silicon oxide film 7a. On the other hand, in the present embodiment, as shown in FIGS. 47 and 48, the insulator film 5 is composed of, unlike the first embodiment (but in the same way as the fifth embodiment), a single layer film (single layer) of the silicon oxide film 5f, and the insulator film 7 is composed of, unlike the first embodiment (but in the same way as the third and seventh embodiments), a stacked film of the silicon oxide film 7d, the silicon nitride film 7e and the silicon oxide film 7f sequentially stacked from below (a side of the insulator film 5). Other than that, a configuration of the semiconductor device according to the present embodiment is similar to that of the first embodiment, and therefore, an explanation thereof is omitted herein.

Figure 49:
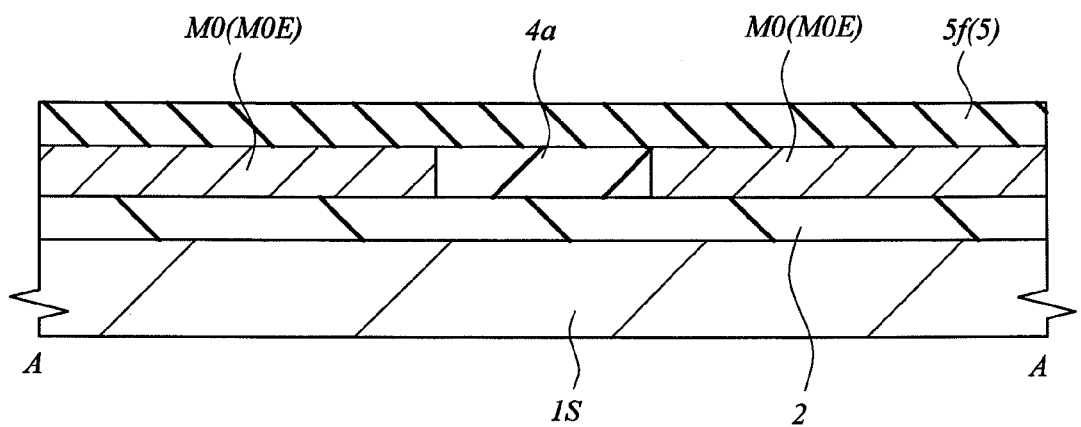
FIG. 49 is a cross-sectional view of the main portion of the semiconductor device during a manufacturing processing according to the eighth embodiment of the present invention.
Figure 50:
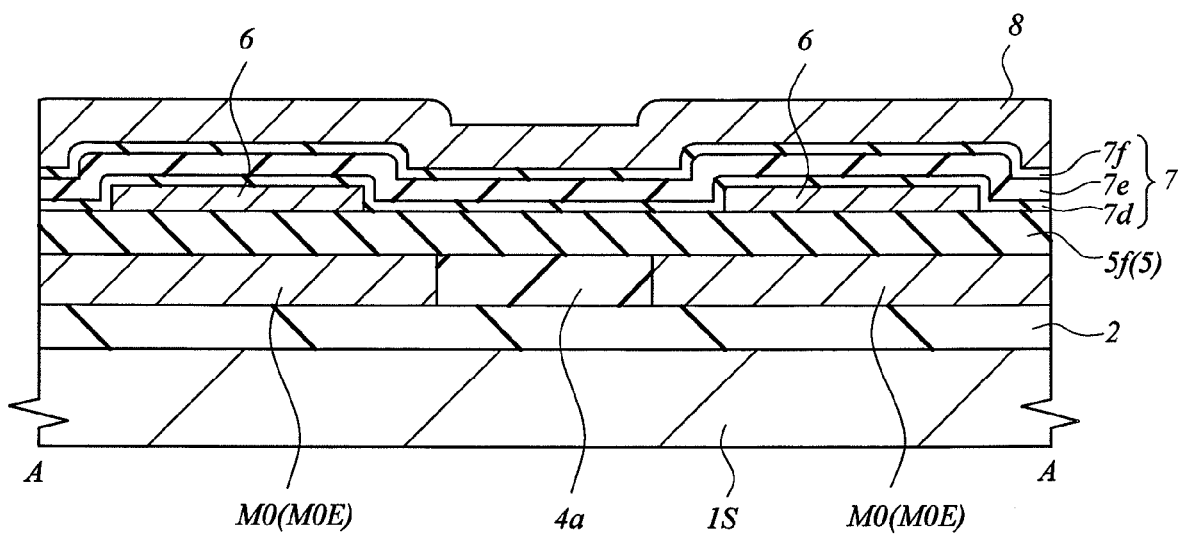
FIG. 50 is a cross-sectional view of the main portion of the semiconductor device during the manufacturing processing according to the eighth embodiment of the present invention.

FIGS. 49 and 50 are main portion cross-sectional views of the semiconductor device during a manufacturing processing according to the present embodiment, and correspond to FIGS. 11 and 13 of the first embodiment, respectively.

In the present embodiment, after the configuration shown in FIG. 10 is obtained in the same way as the first embodiment, the silicon oxide film 5f is formed (deposited) over the entire surface of the first main surface of the semiconductor substrate 1S (that is, over the upper surfaces of the lower electrode wirings M0 and the insulator film 4a filling the lower electrode wirings M0) using the plasma-enhanced CVD method or the like. With this, the insulator film 5 composed of a single layer film (single layer) of the silicon oxide film 5f is formed. A film thickness (deposition film thickness) of the silicon oxide film 5f can be approximately 200 nm, for example.

After formation of the insulator film 5, processings similar to those in the first embodiment are performed until a processing immediately before formation of the insulator film 7. That is, as shown in FIG. 50, the sacrificial film pattern 6 is formed over the insulator film 5 composed of the silicon oxide film 5f, in the same way as the first embodiment.

Then, in the present embodiment, in the same way as the third and seventh embodiments, the silicon oxide film 7d is formed (deposited) over the entire surface of the first main surface 1Sa of the semiconductor substrate 1S (that is, over the insulator film 5) using the plasma-enhanced CVD method or the like so as to cover a surface of the sacrificial film pattern 6, the silicon nitride film 7e is formed (deposited) over the silicon oxide film 7d using the plasma-enhanced CVD method or the like and the silicon oxide film 7f is formed (deposited) over the silicon nitride film 7e using the plasma-enhanced CVD method or the like. With this, the insulator film 7 composed of a stacked film of the silicon oxide film 7d, the silicon nitride film 7e and the silicon oxide film 7f is formed. A film thickness (deposition film thickness) of the silicon oxide film 7d can be approximately 50 nm, for example, a film thickness (deposition film thickness) of the nitride oxide film 7e can be approximately 175 nm, for example and a film thickness (deposition film thickness) of the silicon oxide film 7f can be approximately 50 nm, for example.

Then, in the same way as the first embodiment, the conductive film 8 for formation of the upper electrode wiring M1 (upper electrode M1E) is formed over the insulator film 7 composed of a stacked film of the silicon oxide film 7d, the silicon nitride film 7e and the silicon oxide film 7f. Since processings of formation of the conductive film 8 and thereafter are similar to those in the first embodiment, explanations thereof are omitted herein.

As described above, as shown in FIGS. 47 and 48, the semiconductor device similar to that of the first embodiment except that the single layer film (single layer) of the silicon oxide film 5f is used as the insulator film 5 and the stacked film of the silicon oxide film 7d, the silicon nitride film 7e and the silicon oxide film 7f is used as the insulator film 7 can be obtained.

In the present embodiment, since the insulator films 5 and 7 include the silicon nitride film 7e positioned between the lower electrode M0E (lower electrode wiring M0) and the upper electrode M1E (upper electrode wiring M1), a conduction mechanism of the insulator films 5 and 7 between the upper and lower electrodes becomes the Poole-Frenkel type. As described in the first embodiment, the breakdown voltage between the upper electrode M1E (upper electrode wiring M1) and the lower electrode M0E (lower electrode wiring M0) can be improved. Therefore, performance of the semiconductor device can be improved and the manufacturing yield can be increased.

Furthermore, in the present embodiment, since the silicon oxide film 5f is used as the insulator film 5 and the silicon oxide film 7f is used as the uppermost layer portion of the insulator film 7, a portion of the insulator film 5 contacting with the lower electrode M0E (lower electrode wiring M0) and a portion of the insulator film 7 contacting with the upper electrode M1E (upper electrode wiring M1) are the silicon oxide films 5f and 7f, thereby preventing the silicon nitride film 7e included in the insulator films 5 and 7 from contacting with both of the lower electrode M0E and the upper electrode M1E. With this, as described in the first embodiment, charge trapping to the silicon nitride film 7e included in the insulator films 5 and 7 can be suppressed or prevented, and fluctuation of the characteristic of the capacitive element (transducer) composed of the lower electrode M0E, the insulator film 5, the void VR, the insulator film 7 and the upper electrode M1E caused by charge trapping to the silicon nitride film 7e can be suppressed or prevented. Thus, the performance of the semiconductor device can be improved.

Accordingly, both of improvement of the breakdown voltage between the electrodes of the ultrasonic transducer and suppression of fluctuation of the transmitting/receiving gain caused by charge trapping of the insulator film can be achieved.

Ninth Embodiment

Figure 51:
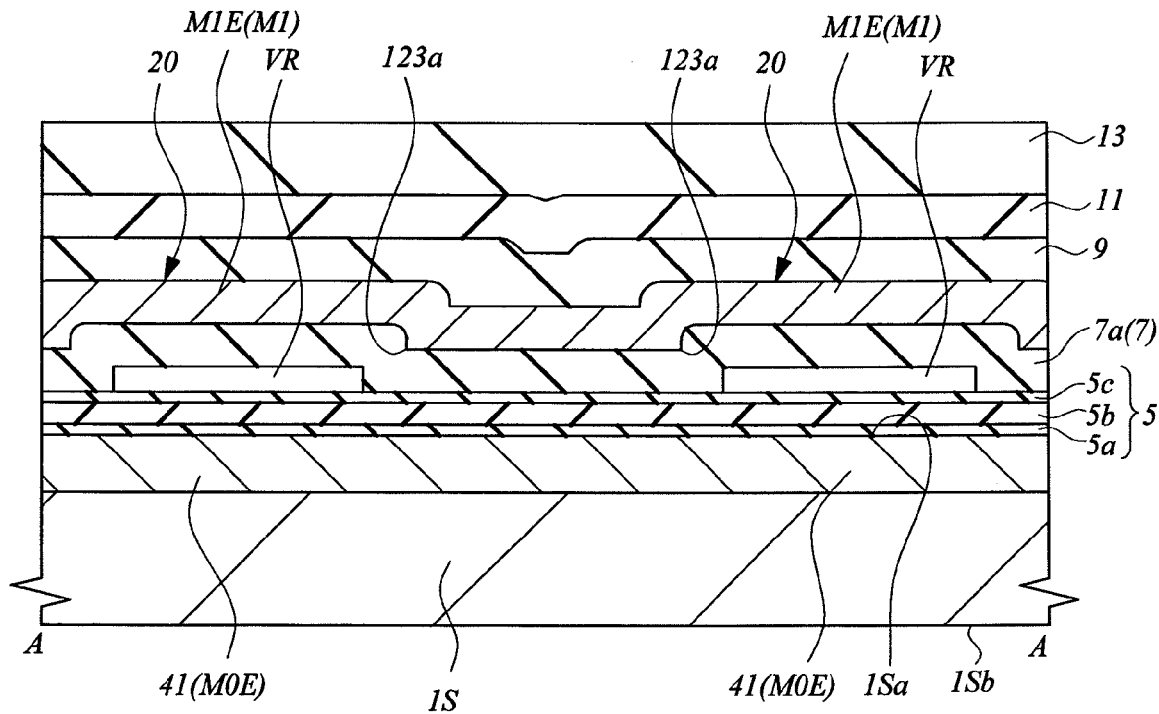
FIG. 51 is a cross-sectional view of a main portion of a semiconductor chip according to a ninth embodiment of the present invention.
Figure 52:
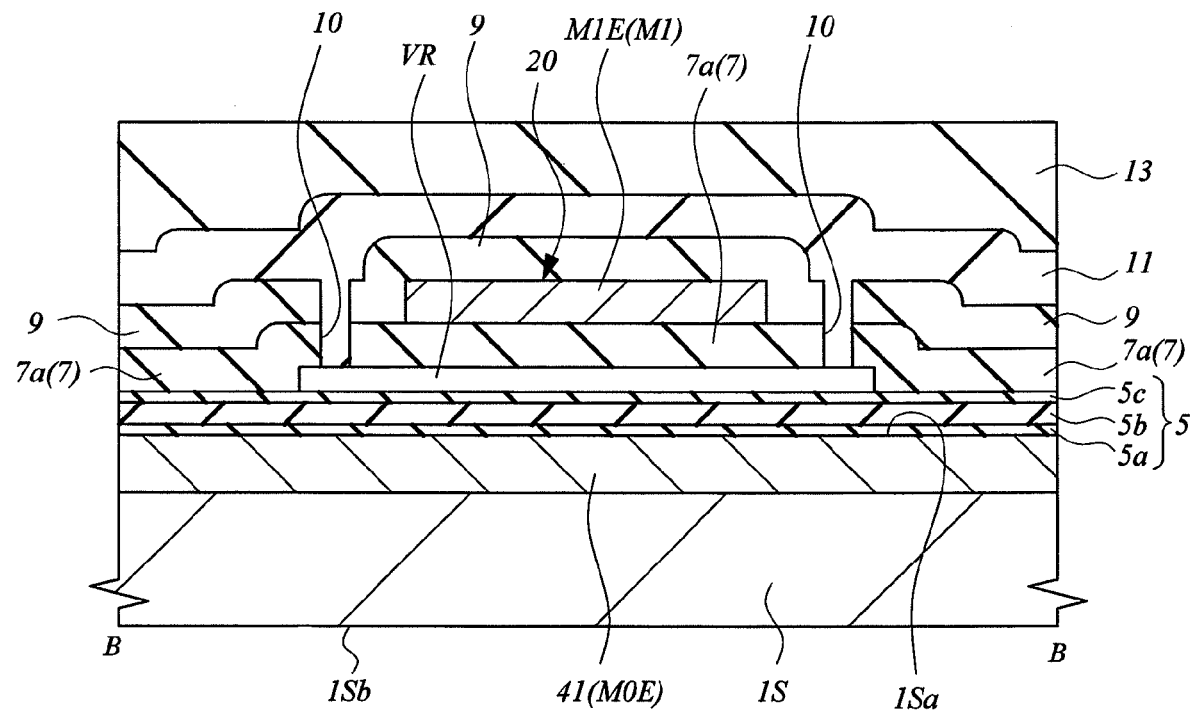
FIG. 52 is a cross-sectional view of the main portion of the semiconductor chip according to the ninth embodiment of the present invention.

FIGS. 51 and 52 are main portion cross-sectional views of a semiconductor device according to the present embodiment and correspond to FIGS. 5 and 6 of the first embodiment, respectively.

In the first embodiment, the stacked structure of the lower electrode M0E (lower electrode wiring M0), the insulator film 5, the void VR, the insulator film 7 and the upper electrode M1E (upper electrode wiring M1) is formed over (the main surface 1Sa of) the semiconductor substrate 1S. The lower electrode M0E (lower electrode wiring M0) is provided over the main surface 1Sa of the semiconductor substrate 1S via the insulator film 2, and is formed of the patterned conductive film 3. On the other hand, in the present embodiment, one corresponding to the lower electrode M0E (lower electrode wiring M0) is composed of an n-type semiconductor region 41 formed in the semiconductor substrate 1S.

That is, in the present embodiment, as shown in FIGS. 51 and 52, the n-type semiconductor region (dopant diffusion layer) 41 is formed in a surface layer portion in the semiconductor substrate 1S. This n-type semiconductor region 41 functions as the lower electrode M0E. Therefore, in the present embodiment, the lower electrode M0E is formed of a part of the semiconductor substrate 1S (in the present embodiment, the n-type semiconductor region 41). And, in the present embodiment, ones corresponding to the insulator film 2, the conductive film 3 and the insulator film 4 (4a) in the first embodiment are not formed. The insulator film 5 of the first embodiment and an upper structure thereof (the void VR, the insulator film 7, the upper electrode wiring M1 and the insulator films 9, 11 and 13) are formed over the main surface of the semiconductor substrate 1S (that is, over the n-type semiconductor region 41). Other than that, a configuration of the semiconductor device according to the present embodiment is similar to that of the first embodiment, and therefore, an explanation thereof is omitted herein.

Figure 53:
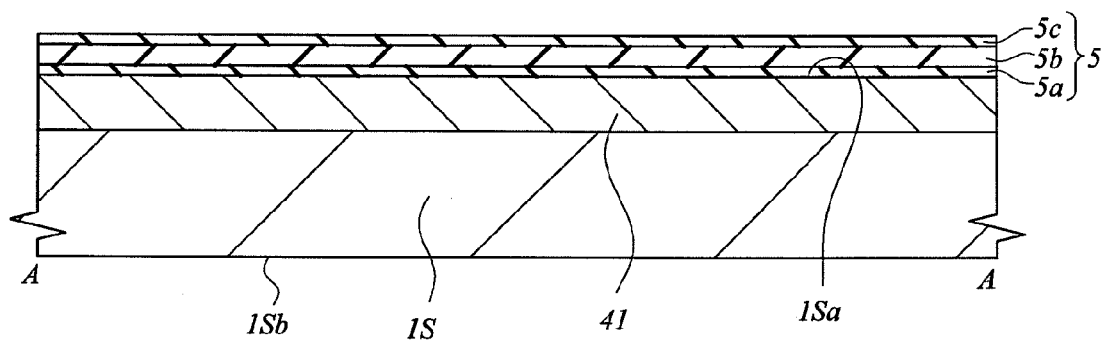
FIG. 53 is a cross-sectional view of the main portion of the semiconductor device during a manufacturing processing according to the ninth embodiment of the present invention.
Figure 54:
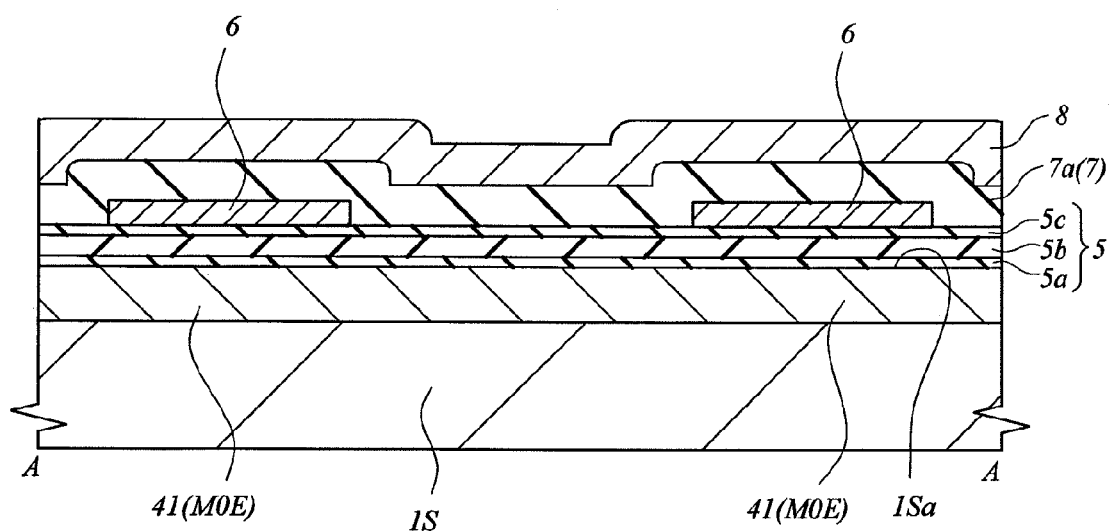
FIG. 54 is a cross-sectional view of the main portion of the semiconductor device during the manufacturing processing according to the ninth embodiment of the present invention.

FIGS. 53 and 54 are main portion cross-sectional views of the semiconductor device during a manufacturing processing according to the present embodiment, and correspond to FIGS. 11 and 13 of the first embodiment, respectively.

In the present embodiment, after the semiconductor substrate 1S is prepared, the n-type semiconductor region 41 is formed by ion implantation of an n-type dopant such as phosphorous (P) or arsenic (As) into the surface layer portion of the semiconductor substrate S1 or the like, as shown in FIG. 53.

Next, the insulator film 2, the conductive film 3 and the insulator film 4 (4a) are not formed, but the insulator film 5 is formed (deposited) over the entire surface of the main surface of the semiconductor substrate 1S, that is, over the semiconductor region 41. Also in the present embodiment, the insulator film 5 is composed of, in the same way as the first embodiment, a stacked film of the silicon oxide film 5a, the silicon nitride film 5b and the silicon oxide film 5c sequentially from below, and can be formed in the same way as the first embodiment.

After formation of the insulator film 5, processings similar to those in the first embodiment are performed. That is, as shown in FIG. 54, in the same way as the first embodiment, the sacrificial film pattern 6 is formed over the insulator film 5, the insulator film 7 composed of the silicon oxide film 7a is formed (deposited) over the entire surface of the first main surface 1Sa of the semiconductor substrate 1S (that is, over the insulator film 5) so as to cover a surface of the sacrificial film pattern 6, and the conductive film 8 for formation of the upper electrode wiring M1 (upper electrode M1E) is formed over the insulator film 7. Since processings of formation of the conductive film 8 and thereafter are similar to those in the first embodiment, explanations thereof are omitted herein.

In the present embodiment, the lower electrode M0E is composed of a part of the semiconductor substrate 1S (in the present embodiment, the n-type semiconductor region 41). Therefore, the upper surface of the lower electrode M0E (n-type semiconductor region 41) is flat, and corner (sharp portion) such as the edge of upper surface 121 shown in FIG. 19 is not formed over the upper surface of the lower electrode M0E (n-type semiconductor region 41). Therefore, in the present embodiment, an electric-field enhancement portion is hard to be generated in the lower electrode M0E (n-type semiconductor region 41) and a leakage current or dielectric breakdown never becomes easy to occur on a route corresponding to the route 122 in FIG. 19. However, also in the present embodiment, in the same way as the first embodiment, a step (corner or step corner) 123a (corresponding to the step 123) is generated over the lower surface of the upper electrode M1E (upper electrode wiring M1) due to the void VR. The electric field is enhanced at this step 123a and the leakage current or the dielectric breakdown becomes easy to occur on a route having this step 123a as a starting point or an ending point (route corresponding to the route 124 shown in FIG. 19). Therefore, even in a case where the lower electrode M0E is composed of a part of the semiconductor substrate 1S (in the present embodiment, n-type semiconductor region 41) as in the present embodiment, a problem similar to that in the first embodiment exists.

In the present embodiment, since the insulator films 5 and 7 include the silicon nitride film 5b positioned between the lower electrode M0E (n-type semiconductor region 41) and the upper electrode M1E (upper electrode wiring M1), a conduction mechanism of the insulator films 5 and 7 between the upper electrode M1E (upper electrode wiring M1) and the lower electrode M0E (n-type semiconductor region 41) becomes the Poole-Frenkel type. As described in the first embodiment, the breakdown voltage between the step 123a of the upper electrode M1E (upper electrode wiring M1) and the lower electrode M0E (n-type semiconductor region 41) can be improved. Therefore, the performance of the semiconductor device can be improved, and the manufacturing yield can be increased.

And, in the present embodiment, since the silicon oxide film 5a is used as the lowermost layer portion of the insulator film 5 and the silicon oxide film 7a is used as the insulator film 7, a portion of the insulator film 5 contacting with the lower electrode M0E (n-type semiconductor region 41) and a portion of the insulator film 7 contacting with the upper electrode M1E (upper electrode wiring M1) are the silicon oxide films 5a and 7a, respectively, thereby preventing the silicon nitride film 5b included in the insulator films 5 and 7 from contacting with both of the lower electrode M0E (n-type semiconductor region 41) and the upper electrode M1E. With this, as described in the first embodiment, charge trapping to the silicon nitride film 5b included in the insulator films 5 and 7 can be suppressed or prevented, and therefore fluctuation of the characteristic of the capacitive element (transducer) composed of the lower electrode M0E (n-type semiconductor region 41), the insulator film 5, the void VR, the insulator film 7 and the upper electrode M1E caused by charge trapping to the silicon nitride film 5b can be suppressed or prevented. Thus, the performance of the semiconductor device can be improved.

Therefore, both of improvement of the breakdown voltage between the electrodes of the ultrasonic transducer and suppression of fluctuation of the transmitting/receiving gain caused by charge trapping of the insulator films can be achieved.

And, in the present embodiment, the n-type semiconductor region 41 is formed over the entire CMUT region CA to serve as the common lower electrode M0E. On the other hand, in the first to eighth embodiments, the lower electrode wiring M0 (lower electrode M0E) is provided over the main surface of the semiconductor substrate 1S, and is formed of the patterned conductive film 3. Therefore, the lower electrode wiring M0 (lower electrode M0E) can be divided in an X direction in FIGS. 1 to 4 to be a plurality of channels, the transducer 20 can be controlled in a matrix manner, and therefore, the ultrasonic transducer with higher performance can be realized.

And, in a case where the lower electrode wiring M0 (lower electrode M0E) is formed of the patterned conductive film 3 as in the first to eighth embodiments, the edge of upper surface 121 shown in FIG. 19 is formed as a corner (sharp portion) in the lower electrode wiring M0 (lower electrode M0E). Since this corner (edge of upper surface 121) is sharper than the step 123a of the upper electrode wiring M1 due to the void VR, the electric-field enhancement is easy to occur therein. Therefore, the breakdown voltage between the upper electrode M1E (upper electrode wiring M1) and the lower electrode M0E (n-type semiconductor area 41) is decreased more significantly in the case where the lower electrode M0E is formed of the patterned conductive film 3 than the case where the lower electrode M0E is formed of a part of the semiconductor substrate (n-type semiconductor area 41). Thus, it is very important to add some twist to film structures of the insulator films 5 and 7 as in the first to eighth embodiments to improve the breakdown voltage between the upper and lower electrodes.

Furthermore, by combining the ninth embodiment with the second to eighth embodiments, the film structures of the insulator films 5 and 7 can be changed as that of the second to eighth embodiments in the configuration of the ninth embodiment.

Note that, in the ninth embodiment, the lower electrode M0E is formed of the n-type semiconductor region 41. Alternatively, as the lower electrode M0E, in place of the n-type semiconductor region 41, a p-type semiconductor region may be formed by ion implantation of boron (B) or $BF_2$, for example.

Materials forming the CMUT cell in the first to ninth embodiments described above are merely an example of combination. A case where low-resistance metal films are used for the upper and lower electrodes (upper electrode M1E and lower electrode M0E), and the intermetal insulating films (insulator films 5 and 7) and the sacrificial film (film for the sacrificial film pattern 6) are formed using the plasma-enhanced CVD method capable of depositing at a low temperature such as 400° C. at which metal films do not melt is explained. However, any conductive film can be used as the upper and lower electrodes (upper electrode M1E and lower electrode M0E), and a polycrystalline silicon film (doped polysilicon film) resistant to a high temperature process with 1000° C. or more can be used, for example. In this case, the silicon oxide film and the silicon nitride film forming the intermetal insulating films (insulator films 5 and 7) may be deposited using a Low Pressure Chemical Vapor Deposition (LPCVD) method, which is a process at a temperature higher than that of the plasma-enhanced CVD method.

And, after the silicon oxide film and the silicon nitride film for the insulator films 5 and 7 are deposited, annealing may be performed in any manufacturing processing thereafter in order to decrease trapping in these insulator films to improve film quality.

Furthermore, material of the sacrificial film (a film for the sacrificial film pattern 6) can be arbitrary as long as it can ensure etching selectivity with the material surrounding the sacrificial film pattern 6 (portions of the insulator films 5 and 7 contacting with the sacrificial film pattern 6), such as amorphous silicon or polycrystalline silicon, for example.

And, although the CMUT cell has a hexagonal shape in FIGS. 3 to 5, the shape is not restricted to this, and can be a circular shape or a rectangular shape, for example.

In the foregoing, the invention made by the inventors of the present invention has been concretely described based on the embodiments. However, it is needless to say that the present invention is not limited to the foregoing embodiments and various modifications and alterations can be made within the scope of the present invention.

The present invention is suitable for application to, for example, a semiconductor device comprising an ultrasonic transducer.

What is claimed is:

1. A semiconductor device comprising:
a first electrode and a second electrode arranged so as to face each other via a first insulator film, a void and a second insulator film,
wherein the first insulator film is formed over the first electrode,
wherein the second insulator film is formed over the first insulator film,
wherein the second electrode is formed over the second insulator film,
wherein the void is formed between the first insulator film and the second insulator film,
wherein at least a portion of the first insulator film contacting with the first electrode is made of silicon oxide,
wherein at least a portion of the second insulator film contacting with the second electrode is made of silicon oxide, and
wherein at least one of the first insulator film and the second insulator film comprises a silicon nitride layer portion, said silicon nitride layer portion being positioned between the first electrode and the second electrode without contacting either the first electrode or the second electrode.

2. The semiconductor device according to claim 1, wherein a stacked structure of the first electrode, the first insulator film, the void, the second insulator film and the second electrode is formed over a semiconductor substrate.

3. The semiconductor device according to claim 2, wherein the first electrode is formed over a main surface of the semiconductor substrate via a third insulator film.

4. The semiconductor device according to claim 3, wherein the first electrode is composed of a patterned conductive film.

5. The semiconductor device according to claim 1, wherein the first insulator film is composed of a stacked film of a first silicon oxide film contacting with the first electrode and a silicon nitride film formed over the first silicon oxide film, and
wherein the second insulator film is composed of one of a single layer film and a stacked film comprising a second silicon oxide film contacting with the second electrode.

6. The semiconductor device according to claim 1, wherein the first insulator film is composed of one of a single layer film and a stacked film comprising a first silicon oxide film contacting with the first electrode, and
wherein the second insulator film is composed of a stacked film comprising a second silicon oxide film contacting with the second electrode and a silicon nitride film formed under the second silicon oxide film.

7. The semiconductor device according to claim 1, wherein the first insulator film is composed of a stacked film of a silicon oxide film, a silicon nitride film and a silicon oxide film sequentially stacked from a side of the first electrode, and
wherein the second insulator film is composed of a single layer film of a silicon oxide film.

8. The semiconductor device according to claim 1, wherein the first insulator film is composed of a stacked film of a silicon oxide film, a silicon nitride film and a silicon oxide film sequentially stacked from a side of the first electrode, and
wherein the second insulator film is composed of a stacked film of a silicon nitride film and a silicon oxide film sequentially stacked from a side of the first insulator film.

9. The semiconductor device according to claim 1, wherein the first insulator film is composed of a stacked film of a silicon oxide film, a silicon nitride film and a silicon oxide film sequentially stacked from a side of the first electrode, and
wherein the second insulator film is composed of a stacked film of a silicon oxide film, a silicon nitride film and a silicon oxide film sequentially stacked from a side of the first insulator film.

10. The semiconductor device according to claim 1,
wherein the first insulator film is composed of a stacked film of a silicon oxide film and a silicon nitride film sequentially stacked from a side of the first electrode, and
wherein the second insulator film is composed of a single layer film of a silicon oxide film.

11. The semiconductor device according to claim 1,
wherein the first insulator film is composed of a single layer film of a silicon oxide film, and
wherein the second insulator film is composed of a stacked film of a silicon nitride film and a silicon oxide film sequentially stacked from a side of the first insulator film.

12. The semiconductor device according to claim 1,
wherein the first insulator film is composed of a stacked film of a silicon oxide film and a silicon nitride film sequentially stacked from a side of the first electrode, and
wherein the second insulator film is composed of a stacked film of a silicon nitride film and a silicon oxide film sequentially stacked from a side of the first insulator film.

13. The semiconductor device according to claim 1,
wherein the first insulator film is composed of a stacked film of a silicon oxide film and a silicon nitride film sequentially stacked from a side of the first electrode, and
wherein the second insulator film is composed of a stacked film of a silicon oxide film, a silicon nitride film and a silicon oxide film sequentially stacked from a side of the first insulator film.

14. The semiconductor device according to claim 1,
wherein the first insulator film is composed of a single layer film of a silicon oxide film, and
wherein the second insulator film is composed of a stacked film of a silicon oxide film, a silicon nitride film and a silicon oxide film sequentially stacked from a side of the first insulator film.

15. The semiconductor device according to claim 1,
wherein a capacitive element is composed of the first electrode, the second electrode, the first insulator film, the void and the second insulator film, the first insulator film, void and second insulator film being between the first electrode and the second electrode.

16. The semiconductor device according to claim 1,
wherein an ultrasonic transducer is composed of the first electrode, the second electrode, the first insulator film, the void and the second insulator film, the first insulator film, void and second insulator film being between the first electrode and the second electrode.

17. A semiconductor device comprising:
a first electrode formed over a main surface of a semiconductor substrate;
a first insulator film formed over the main surface of the semiconductor substrate so as to cover the first electrode;
a second insulator film formed over the first insulator film;
a second electrode formed over the second insulator film; and
a void formed between the first insulator film and the second insulator film,
wherein the first electrode and the second electrode are arranged so as to face each other via the first insulator film, the void and the second insulator film,
wherein at least a portion of the first insulator film contacting with the first electrode is made of silicon oxide,
wherein at least a portion of the second insulator film contacting with the second electrode is made of silicon oxide, and
wherein at least one of the first insulator film and the second insulator film comprises a silicon nitride layer portion, said silicon nitride layer portion being positioned between the first electrode and the second electrode and in without contacting either the first electrode or the second electrode.

18. The semiconductor device according to claim 17, further comprising:
a third insulator film formed over the main surface of the semiconductor substrate,
wherein the first electrode is formed over the third insulator film.

19. The semiconductor device according to claim 17,
wherein the first insulator film is composed of a stacked film comprising a first silicon oxide film contacting with the first electrode and a silicon nitride film formed over the first silicon oxide film, and
wherein the second insulator film is composed of one of a single layer film and a stacked film comprising a second silicon oxide film contacting with the second electrode.

20. The semiconductor device according to claim 17,
wherein the first insulator film is composed of one of a single layer film and a stacked film comprising a first silicon oxide film contacting with the first electrode, and
wherein the second insulator film is composed of a stacked film comprising a second silicon oxide film contacting with the second electrode and a silicon nitride film formed under the second silicon oxide film.

21. The semiconductor device according to claim 17,
wherein the first insulator film is composed of a stacked film of a silicon oxide film, a silicon nitride film and a silicon oxide film sequentially stacked from a side of the first electrode, and
wherein the second insulator film is composed of a single layer film of a silicon oxide film.

22. The semiconductor device according to claim 17,
wherein the first insulator film is composed of a stacked film of a silicon oxide film, a silicon nitride film and a silicon oxide film sequentially stacked from a side of the first electrode, and
wherein the second insulator film is composed of a stacked film of a silicon nitride film and a silicon oxide film sequentially stacked from a side of the first insulator film.

23. The semiconductor device according to claim 17,
wherein the first insulator film is composed of a stacked film of a silicon oxide film, a silicon nitride film and a silicon oxide film sequentially stacked from a side of the first electrode, and
wherein the second insulator film is composed of a stacked film of a silicon oxide film, a silicon nitride film and a silicon oxide film sequentially stacked from a side of the first insulator film.

24. The semiconductor device according to claim 17,
wherein the first insulator film is composed of a stacked film of a silicon oxide film and a silicon nitride film sequentially stacked from a side of the first electrode, and
wherein the second insulator film is composed of a single layer film of a silicon oxide film.

25. The semiconductor device according to claim 17,
wherein the first insulator film is composed of a single layer film of a silicon oxide film, and wherein the second insulator film is composed of a stacked film of a silicon nitride film and a silicon oxide film sequentially stacked from a side of the first insulator film.

26. The semiconductor device according to claim 17,
wherein the first insulator film is composed of a stacked film of a silicon oxide film and a silicon nitride film sequentially stacked from a side of the first electrode, and
wherein the second insulator film is composed of a stacked film of a silicon nitride film and a silicon oxide film sequentially stacked from a side of the first insulator film.

27. The semiconductor device according to claim 17,
wherein the first insulator film is composed of a stacked film of a silicon oxide film and a silicon nitride film sequentially stacked from a side of the first electrode, and
wherein the second insulator film is composed of a stacked film of a silicon oxide film, a silicon nitride film and a silicon oxide film sequentially stacked from a side of the first insulator film.

28. The semiconductor device according to claim 17,
wherein the first insulator film is composed of a single layer film of a silicon oxide film, and
wherein the second insulator film is composed of a stacked film of a silicon oxide film, a silicon nitride film and a silicon oxide film sequentially stacked from a side of the first insulator film.

29. The semiconductor device according to claim 17,
wherein a capacitive element is composed of the first electrode, the second electrode, the first insulator film, the void and the second insulator film, the first insulator film, void and second insulator film being between the first electrode and the second electrode.

30. The semiconductor device according to claim 17,
wherein an ultrasonic transducer is composed of the first electrode, the second electrode, the first insulator film, the void and the second insulator film, the first insulator film, void and second insulator film being between the first electrode and the second electrode.

* * * * *